US006838079B2

(12) United States Patent
Snodgrass et al.

(10) Patent No.: US 6,838,079 B2
(45) Date of Patent: Jan. 4, 2005

(54) METHODS FOR USING THE OBESE PRODUCT TO STIMULATE HEMATOPOIETIC DEVELOPMENT

(75) Inventors: H. Ralph Snodgrass, Powell, OH (US); Joseph Cioffi, New Albany, OH (US); Thomas Joel Zupancic, Worthington, OH (US); Alan Wayne Shafer, Lancaster, OH (US)

(73) Assignee: Indevus Pharmaceuticals, Inc., Lexington, MA (US)

( * ) Notice: Subject to any disclaimer, the term of this patent is extended or adjusted under 35 U.S.C. 154(b) by 0 days.

(21) Appl. No.: 10/095,929

(22) Filed: Mar. 12, 2002

(65) Prior Publication Data

US 2002/0197232 A1 Dec. 26, 2002

Related U.S. Application Data

(63) Continuation of application No. 08/618,957, filed on Mar. 20, 1996, now Pat. No. 6,355,237, which is a continuation-in-part of application No. 08/589,915, filed on Jan. 23, 1996, now abandoned, which is a continuation-in-part of application No. 08/355,888, filed on Dec. 14, 1994, now Pat. No. 5,763,211, which is a continuation-in-part of application No. 08/306,231, filed on Sep. 14, 1994, now Pat. No. 5,643,748.

(51) Int. Cl.$^7$ ........................ A61K 38/19; C07K 14/715
(52) U.S. Cl. ........................ 424/85.1; 530/351; 514/12; 514/814; 514/885
(58) Field of Search ............................. 530/350; 514/12

(56) References Cited

FOREIGN PATENT DOCUMENTS

| EP | 0 409 607 A2 | 1/1991 |
|---|---|---|
| EP | 0 521 156 A1 | 1/1993 |
| WO | WO 88/02757 | 4/1988 |
| WO | WO 93/10151 | 5/1993 |
| WO | WO 96/07737 | 3/1996 |
| WO | WO 01/18040 | * 3/2001 |

OTHER PUBLICATIONS

Margetic et al., Leptin: a review of its peripheral actions and interactions, International Journal of Obesity, vol. 26, pp. 1407–1433, May 27, 2002.*
Barinaga, 1996, "Obesity: Leptin Receptor Weigh In," *Science* 271:29.
Streamson et al., 1996, "Phenotypes of Mouse *diabetes* and Rat *fatty* Due to Mutations in the OB (Leptin) Receptor," *Science* 271:994–996.
Cioffi et al., 1996, "Novel B219/OB Receptor Isoforms: Possible Roles of Leptin in Hematopoiesis and Reproduction," *Nature Medicine* 2(5):585–589.
Tartaglia et al., 1995, "Identification and Expression Cloning of a Leptin Receptor, OB–R," *Cell* 83:1263–1271.
Pelleymounter et al., 1995, "Effects of the obese Gene Product on Body Weight Regulation in ob/ob Mice," *Science* 269:540–549.

Beckmann et al., 1994, "Molecular characterization of a family of ligands for eph–related tyrosine kinase receptors," *The EMBO Journal* 13(16):3757–3762.
Miyajima et al., 1993, "Receptors for Granulocyte–Macrophage Colony–Stimulating Factor, Interleukin–3, and Interleukin–5," *Blood* 82(7):1960–1974.
Saito et al., 1992, "Molecular Cloning of a Murine Il–6 Receptor–Associated Signal Transducer, gp130, and its Regulated Expression in Vivo," *J. Immunol.* 148(12):4066–4071.
Park et al., 1992, "Cloning of the low–affinity murine granulocyte–macrophage colony–stimulating factor receptor and reconstitution of a high–affinity receptor complex," *Proc. Natl. Acad. Sci. U.S.A.* 89:4295–4299.
Miyajima et al., 1992, "Cytokine Receptors and Signal Transduction," *Ann. Rev. Immunol.* 10:295–331.
Truett et al., 1991, "Rat obesity gene fatty (fa) maps to chromosome 5: Evidence for homology with the mouse gene diabetes (db)," Proc. Natl. Acad. Sci. U.S.A. 88:7806–7809.
Larsen et al., 1990, "Expression Cloning of a Human Granulocyte Colony–stimulating Factor Receptor: A Structural Mosaic of Hematopoietin Receptor, Immunoglobulin, and Fibronectin Domains," *J. Exp. Med.* 172:1559–1570.
Hibi et al., 1990, "Molecular Cloning and Expression of a Il–6 Signal Transducer, gp130," *Cell* 63:1149–1157.
Hayashida et al., 1990, "Molecular cloning of a second subunit of the receptor for human granulocyte–macrophage colony–stimulating factor (GM–CSF): Reconstitution of a high–affinity GM–CSF receptor," *Proc. Natl. Acad. Sci. U.S.A.* 87:9655–9659.
Harada et al., 1990, "Expression Cloning of a cDNA Encoding the Murine Interleukin 4 Receptor Based on Ligand Binding," *Proc. Natl. Acad. Sci. U.S.A.* 87:857–861.
Gorman et al., 1990, "Cloning and Expresion of a Gene Encoding an Interleukin 3 receptor–Like Protein: Identification of Another Member of the Cytokine Receptor Gene Family," *Proc. Natl. Acad. Sci. U.S.A.* 87:5459–5463.

(List continued on next page.)

*Primary Examiner*—Christine J. Saoud
*Assistant Examiner*—Eileen B. O'Hara
(74) *Attorney, Agent, or Firm*—Jones Day

(57) ABSTRACT

The present invention relates to methods for using various forms of a novel receptor expressed by hematopoietic and endothelial cells. An additional variant form of this receptor has been detected in brain cells and shown to bind to the obese gene product, leptin. Therefore, leptin may be used to stimulate the growth and development of receptor-positive hematopoietic and endothelial cells in vitro and in vivo. In addition, this receptor is selectively expressed in hematopoietic progenitor cells with long-term repopulating potential. Thus, agents that specifically bind to this receptor may be used to identify and isolate progenitor cells for a variety of clinical applications.

11 Claims, 19 Drawing Sheets

OTHER PUBLICATIONS

Figure 4:
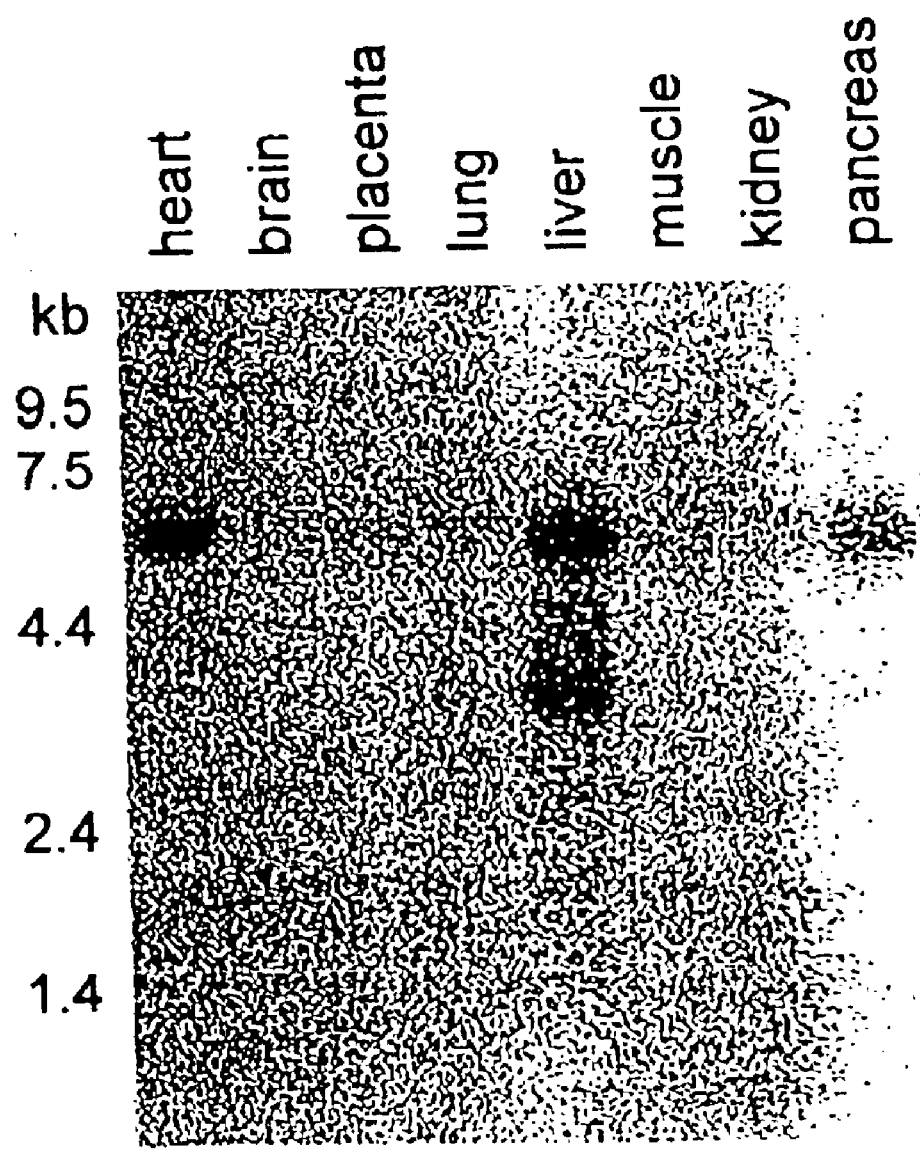

Fukunaga et al., 1990, "Expression Cloning of a Receptor for Murine Granulocyte Colony–Stimulating Factor," *Cell 61*:341–350.

Cosman et al., 1990, "A new Cytokine Receptor Superfamily," *TIBS 15*:265–269.

Bazan, 1990, "Structural Design and Molecuar Evolution of a Cytokine Receptor Superfamily," *Proc. Natl. Acad. Sci. U.S.A. 87*:6934–6938.

Bahary et al., 1990, "Molecular Mapping of the Mouse db Mutation," *Proc. Natl. Acad. Sci. U.S.A. 87*:8642–8646.

Mosley et al., 1989, "The Murine Interleukin–4 Receptor: Molecular Cloning and Characterization of Secreted and Membrane Bound Forms," *Cell 59*:335–348.

Gearing et al., 1989, "Expression cloning of a receptor for human granulocyte–macrophage colony–stimulating factor," *The EMBO Journal 8(12)*:3667–3676.

Yamasaki et al., 1988, "Cloning and Expression of the Human Interleukin–6 (BSF–2/IFNβ 2) Receptor," *Science 241*:825–828.

Gearing et al., 1987, "Molecular Cloning and Expression of cDNA Encoding a Murine Myeloid Leukaemia Inhibitory Factor (LIF)," *The EMBO Journal 6*:3995–4002.

Bennett et al., 1996, "A role for leptin and its cognate receptor in hematopoiesis," *Current Biology 6(9)*:1170–1180.

\* cited by examiner

```
              9          18          27          36          45          54
GCG CGC GCG ACG CAG GTG CCC GAG CCC CGG CCC GCG CCC ATC TCT GCC TTC GGT
--- --- --- --- --- --- --- --- --- --- --- --- --- --- --- --- --- ---
 A   R   A   T   Q   V   P   E   P   R   P   A   P   I   S   A   F   G 63          72          81          90          99         108
CGA GTT GGA CCC CCG GAT CAA GGT GTA CTT CTC TGA AGT AAG ATG ATT TGT CAA
--- --- --- --- --- --- --- --- --- --- --- --- --- --- --- --- --- ---
 R   V   G   P   P   D   Q   G   V   L   L   *   S   K   M   I   C   Q 117         126         135         144         153         162
AAA TTC TGT GTG GTT TTG TTA CAT TGG GAA TTT ATT TAT GTG ATA ACT GCG TTT
--- --- --- --- --- --- --- --- --- --- --- --- --- --- --- --- --- ---
 K   F   C   V   V   L   L   H   W   E   F   I   Y   V   I   T   A   F 171         180         189         198         207         216
AAC TTG TCA TAT CCA ATT ACT CCT TGG AGA TTT AAG TTG TCT TGC ATG CCA CCA
--- --- --- --- --- --- --- --- --- --- --- --- --- --- --- --- --- ---
 N   L   S   Y   P   I   T   P   W   R   F   K   L   S   C   M   P   P 225         234         243         252         261         270
AAT TCA ACC TAT GAC TAC TTC CTT TTG CCT GCT GGA CTC TCA AAG AAT ACT TCA
--- --- --- --- --- --- --- --- --- --- --- --- --- --- --- --- --- ---
 N   S   T   Y   D   Y   F   L   L   P   A   G   L   S   K   N   T   S 279         288         297         306         315         324
AAT TCG AAT GGA CAT TAT GAG ACA GCT GTT GAA CCT AAG TTT AAT TCA AGT GGT
--- --- --- --- --- --- --- --- --- --- --- --- --- --- --- --- --- ---
 N   S   N   G   H   Y   E   T   A   V   E   P   K   F   N   S   S   G 333         342         351         360         369         378
ACT CAC TTT TCT AAC TTA TCC AAA GCA ACT TTC CAC TGT TGC TTT CGG AGT GAG
--- --- --- --- --- --- --- --- --- --- --- --- --- --- --- --- --- ---
 T   H   F   S   N   L   S   K   A   T   F   H   C   C   F   R   S   E 387         396         405         414         423         432
CAA GAT AGA AAC TGC TCC TTA TGT GCA GAC AAC ATT GAA GGA AGG ACA TTT GTT
--- --- --- --- --- --- --- --- --- --- --- --- --- --- --- --- --- ---
 Q   D   R   N   C   S   L   C   A   D   N   I   E   G   R   T   F   V
```

FIG.1A

```
        441             450             459             468             477             486
TCA ACA GTA AAT TCT TTA GTT TTT CAA CAA ATA GAT GCA AAC TGG AAC ATA CAG
--- --- --- --- --- --- --- --- --- --- --- --- --- --- --- --- --- ---
 S   T   V   N   S   L   V   F   Q   Q   I   D   A   N   W   N   I   Q 495             504             513             522             531             540
TGC TGG CTA AAA GGA GAC TTA AAA TTA TTC ATC TGT TAT GTG GAG TCA TTA TTT
--- --- --- --- --- --- --- --- --- --- --- --- --- --- --- --- --- ---
 C   W   L   K   G   D   L   K   L   F   I   C   Y   V   E   S   L   F 549             558             567             576             585             594
AAG AAT CTA TTC AGG AAT TAT AAC TAT AAG GTC CAT CTT TTA TAT GTT CTG CCT
--- --- --- --- --- --- --- --- --- --- --- --- --- --- --- --- --- ---
 K   N   L   F   R   N   Y   N   Y   K   V   H   L   L   Y   V   L   P 603             612             621             630             639             648
GAA GTG TTA GAA GAT TCA CCT CTG GTT CCC CAA AAA GGC AGT TTT CAG ATG GTT
--- --- --- --- --- --- --- --- --- --- --- --- --- --- --- --- --- ---
 E   V   L   E   D   S   P   L   V   P   Q   K   G   S   F   Q   M   V 657             666             675             684             693             702
CAC TGC AAT TGC AGT GTT CAT GAA TGT TGT GAA TGT CTT GTG CCT GTG CCA ACA
--- --- --- --- --- --- --- --- --- --- --- --- --- --- --- --- --- ---
 H   C   N   C   S   V   H   E   C   C   E   C   L   V   P   V   P   T 711             720             729             738             747             756
GCC AAA CTC AAC GAC ACT CTC CTT ATG TGT TTG AAA ATC ACA TCT GGT GGA GTA
--- --- --- --- --- --- --- --- --- --- --- --- --- --- --- --- --- ---
 A   K   L   N   D   T   L   L   M   C   L   K   I   T   S   G   G   V 765             774             783             792             801             810
ATT TTC CGG TCA CCT CTA ATG TCA GTT CAG CCC ATA AAT ATG GTG AAG CCT GAT
--- --- --- --- --- --- --- --- --- --- --- --- --- --- --- --- --- ---
 I   F   R   S   P   L   M   S   V   Q   P   I   N   M   V   K   P   D 819             828             837             846             855             864
CCA CCA TTA GGT TTG CAT ATG GAA ATC ACA GAT GAT GGT AAT TTA AAG ATT TCT
--- --- --- --- --- --- --- --- --- --- --- --- --- --- --- --- --- ---
 P   P   L   G   L   H   M   E   I   T   D   D   G   N   L   K   I   S
```

FIG.1B

```
       873           882           891           900           909           918
TGG TCC AGC CCA CCA TTG GTA CCA TTT CCA CTT CAA TAT CAA GTG AAA TAT TCA
--- --- --- --- --- --- --- --- --- --- --- --- --- --- --- --- --- ---
 W   S   S   P   P   L   V   P   F   P   L   Q   Y   Q   V   K   Y   S 927           936           945           954           963           972
GAG AAT TCT ACA ACA GTT ATC AGA GAA GCT GAC AAG ATT GTC TCA GCT ACA TCC
--- --- --- --- --- --- --- --- --- --- --- --- --- --- --- --- --- ---
 E   N   S   T   T   V   I   R   E   A   D   K   I   V   S   A   T   S 981           990           999          1008          1017          1026
CTG CTA GTA GAC AGT ATA CTT CCT GGG TCT TCG TAT GAG GTT CAG GTG AGG GGC
--- --- --- --- --- --- --- --- --- --- --- --- --- --- --- --- --- ---
 L   L   V   D   S   I   L   P   G   S   S   Y   E   V   Q   V   R   G 1035          1044          1053          1062          1071          1080
AAG AGA CTG GAT GGC CCA GGA ATC TGG AGT GAC TGG AGT ACT CCT CGT GTC TTT
--- --- --- --- --- --- --- --- --- --- --- --- --- --- --- --- --- ---
 K   R   L   D   G   P   G   I   W   S   D   W   S   T   P   R   V   F 1089          1098          1107          1116          1125          1134
ACC ACA CAA GAT GTC ATA TAC TTT CCA CCT AAA ATT CTG ACA AGT GTT GGG TCT
--- --- --- --- --- --- --- --- --- --- --- --- --- --- --- --- --- ---
 T   T   Q   D   V   I   Y   F   P   P   K   I   L   T   S   V   G   S 1143          1152          1161          1170          1179          1188
AAT GTT TCT TTT CAC TGC ATC TAT AAG AAG GAA AAC AAG ATT GTT CCC TCA AAA
--- --- --- --- --- --- --- --- --- --- --- --- --- --- --- --- --- ---
 N   V   S   F   H   C   I   Y   K   K   E   N   K   I   V   P   S   K 1197          1206          1215          1224          1233          1242
GAG ATT GTT TGG TGG ATG AAT TTA GCT GAG AAA ATT CCT CAA AGC CAG TAT GAT
--- --- --- --- --- --- --- --- --- --- --- --- --- --- --- --- --- ---
 E   I   V   W   W   M   N   L   A   E   K   I   P   Q   S   Q   Y   D 1251          1260          1269          1278          1287          1296
GTT GTG AGT GAT CAT GTT AGC AAA GTT ACT TTT TTC AAT CTG AAT GAA ACC AAA
--- --- --- --- --- --- --- --- --- --- --- --- --- --- --- --- --- ---
 V   V   S   D   H   V   S   K   V   T   F   F   N   L   N   E   T   K
```

FIG. 1C

```
      1305        1314        1323        1332        1341        1350
CCT CGA GGA AAG TTT ACC TAT GAT GCA GTG TAC TGC TGC AAT GAA CAT GAA TGC
--- --- --- --- --- --- --- --- --- --- --- --- --- --- --- --- --- ---
 P   R   G   K   F   T   Y   D   A   V   Y   C   C   N   E   H   E   C 1359        1368        1377        1386        1395        1404
CAT CAT CGC TAT GCT GAA TTA TAT GTG ATT GAT GTC AAT ATC AAT ATC TCA TGT
--- --- --- --- --- --- --- --- --- --- --- --- --- --- --- --- --- ---
 H   H   R   Y   A   E   L   Y   V   I   D   V   N   I   N   I   S   C 1413        1422        1431        1440        1449        1458
GAA ACT GAT GGG TAC TTA ACT AAA ATG ACT TGC AGA TGG TCA ACC AGT ACA ATC
--- --- --- --- --- --- --- --- --- --- --- --- --- --- --- --- --- ---
 E   T   D   G   Y   L   T   K   M   T   C   R   W   S   T   S   T   I 1467        1476        1485        1494        1503        1512
CAG TCA CTT GCG GAA AGC ACT TTG CAA TTG AGG TAT CAT AGG AGC AGC CTT TAC
--- --- --- --- --- --- --- --- --- --- --- --- --- --- --- --- --- ---
 Q   S   L   A   E   S   T   L   Q   L   R   Y   H   R   S   S   L   Y 1521        1530        1539        1548        1157        1566
TGT TCT GAT ATT CCA TCT ATT CAT CCC ATA TCT GAG CCC AAA GAT TGC TAT TTG
--- --- --- --- --- --- --- --- --- --- --- --- --- --- --- --- --- ---
 C   S   D   I   P   S   I   H   P   I   S   E   P   K   D   C   Y   L 1575        1584        1593        1602        1611        1620
CAG AGT GAT GGT TTT TAT GAA TGC ATT TTC CAG CCA ATC TTC CTA TTA TCT GGC
--- --- --- --- --- --- --- --- --- --- --- --- --- --- --- --- --- ---
 Q   S   D   G   F   Y   E   C   I   F   Q   P   I   F   L   L   S   G 1629        1638        1647        1656        1665        1674
TAC ACA ATG TGG ATT AGG ATC AAT CAC TCT CTA GGT TCA CTT GAC TCT CCA CCA
--- --- --- --- --- --- --- --- --- --- --- --- --- --- --- --- --- ---
 Y   T   M   W   I   R   I   N   H   S   L   G   S   L   D   S   P   P 1683        1692        1701        1710        1719        1728
ACA TGT GTC CTT CCT GAT TCT GTG GTG AAG CCA CTG CCT CCA TCC AGT GTG AAA
--- --- --- --- --- --- --- --- --- --- --- --- --- --- --- --- --- ---
 T   C   V   L   P   D   S   V   V   K   P   L   P   P   S   S   V   K
```

FIG. 1D

```
             1737        1746        1755        1764        1773        1782
      GCA GAA ATT ACT ATA AAC ATT GGA TTA TTG AAA ATA TCT TGG GAA AAG CCA GTC
      ... ... ... ... ... ... ... ... ... ... ... ... ... ... ... ... ... ...
       A   E   I   T   I   N   I   G   L   L   K   I   S   W   E   K   P   V 1791        1800        1809        1818        1827        1836
      TTT CCA GAG AAT AAC CTT CAA TTC CAG ATT CGC TAT GGT TTA AGT GGA AAA GAA
      ... ... ... ... ... ... ... ... ... ... ... ... ... ... ... ... ... ...
       F   P   E   N   N   L   Q   F   Q   I   R   Y   G   L   S   G   K   E 1845        1854        1863        1872        1881        1890
      GTA CAA TGG AAG ATG TAT GAG GTT TAT GAT GCA AAA TCA AAA TCT GTC AGT CTC
      ... ... ... ... ... ... ... ... ... ... ... ... ... ... ... ... ... ...
       V   Q   W   K   M   Y   E   V   Y   D   A   K   S   K   S   V   S   L 1899        1908        1917        1926        1935        1944
      CCA GTT CCA GAC TTG TGT GCA GTC TAT GCT GTT CAG GTG CGC TGT AAG AGG CTA
      ... ... ... ... ... ... ... ... ... ... ... ... ... ... ... ... ... ...
       P   V   P   D   L   C   A   V   Y   A   V   Q   V   R   C   K   R   L 1953        1962        1971        1980        1989        1998
      GAT GGA CTG GGA TAT TGG AGT AAT TGG AGC AAT CCA GCC TAC ACA GTT GTC ATG
      ... ... ... ... ... ... ... ... ... ... ... ... ... ... ... ... ... ...
       D   G   L   G   Y   W   S   N   W   S   N   P   A   Y   T   V   V   M 2007        2016        2025        2034        2043        2052
      GAT ATA AAA GTT CCT ATG AGA GGA CCT GAA TTT TGG AGA ATA ATT AAT GGA GAT
      ... ... ... ... ... ... ... ... ... ... ... ... ... ... ... ... ... ...
       D   I   K   V   P   M   R   G   P   E   F   W   R   I   I   N   G   D 2061        2070        2079        2088        2097        2106
      ACT ATG AAA AAG GAG AAA AAT GTC ACT TTA CTT TGG AAG CCC CTG ATG AAA AAT
      ... ... ... ... ... ... ... ... ... ... ... ... ... ... ... ... ... ...
       T   M   K   K   E   K   N   V   T   L   L   W   K   P   L   M   K   N 2115        2124        2133        2142        2151        2160
      GAC TCA TTG TGC AGT GTT CAG AGA TAT GTG ATA AAC CAT CAT ACT TCC TGC AAT
      ... ... ... ... ... ... ... ... ... ... ... ... ... ... ... ... ... ...
       D   S   L   C   S   V   Q   R   Y   V   I   N   H   H   T   S   C   N
```

FIG.1E

```
      2169          2178          2187          2196          2205          2214
GGA ACA TGG TCA GAA GAT GTG GGA AAT CAC ACG AAA TTC ACT TTC CTG TGG ACA
--- --- --- --- --- --- --- --- --- --- --- --- --- --- --- --- --- ---
 G   T   W   S   E   D   V   G   N   H   T   K   F   T   F   L   W   T 2223          2232          2241          2250          2259          2268
GAG CAA GCA CAT ACT GTT ACG GTT CTG GCC ATC AAT TCA ATT GGT GCT TCT GTT
--- --- --- --- --- --- --- --- --- --- --- --- --- --- --- --- --- ---
 E   Q   A   H   T   V   T   V   L   A   I   N   S   I   G   A   S   V 2277          2286          2295          2304          2313          2322
GCA AAT TTT AAT TTA ACC TTT TCA TGG CCT ATG AGC AAA GTA AAT ATC GTG CAG
--- --- --- --- --- --- --- --- --- --- --- --- --- --- --- --- --- ---
 A   N   F   N   L   T   F   S   W   P   M   S   K   V   N   I   V   Q 2331          2340          2349          2358          2367          2376
TCA CTC AGT GCT TAT CCT TTA AAC AGC AGT TGT GTG ATT GTT TCC TGG ATA CTA
--- --- --- --- --- --- --- --- --- --- --- --- --- --- --- --- --- ---
 S   L   S   A   Y   P   L   N   S   S   C   V   I   V   S   W   I   L 2385          2394          2403          2412          2421          2430
TCA CCC AGT GAT TAC AAG CTA ATG TAT TTT ATT ATT GAG TGG AAA AAT CTT AAT
--- --- --- --- --- --- --- --- --- --- --- --- --- --- --- --- --- ---
 S   P   S   D   Y   K   L   M   Y   F   I   I   E   W   K   N   L   N 2439          2448          2457          2466          2475          2484
GAA GAT GGT GAA ATA AAA TGG CTT AGA ATC TCT TCA TCT GTT AAG AAG TAT TAT
--- --- --- --- --- --- --- --- --- --- --- --- --- --- --- --- --- ---
 E   D   G   E   I   K   W   L   R   I   S   S   S   V   K   K   Y   Y 2493          2502          2511          2520          2529          2538
ATC CAT GAT CAT TTT ATC CCC ATT GAG AAG TAC CAG TTC AGT CTT TAC CCA ATA
--- --- --- --- --- --- --- --- --- --- --- --- --- --- --- --- --- ---
 I   H   D   H   F   I   P   I   E   K   Y   Q   F   S   L   Y   P   I 2547          2556          2565          2574          2583          2592
TTT ATG GAA GGA GTG GGA AAA CCA AAG ATA ATT AAT AGT TTC ACT CAA GAT GAT
--- --- --- --- --- --- --- --- --- --- --- --- --- --- --- --- --- ---
 F   M   E   G   V   G   K   P   K   I   I   N   S   F   T   Q   D   D
```

FIG.1F

```
         2601           2610           2619           2628           2637           2646
ATT GAA AAA CAC CAG AGT GAT GCA GGT TTA TAT GTA ATT GTG CCA GTA ATT ATT
--- --- --- --- --- --- --- --- --- --- --- --- --- --- --- --- --- ---
 I   E   K   H   Q   S   D   A   G   L   Y   V   I   V   P   V   I   I 2655           2664           2673           2682           2691           2700
TCC TCT TCC ATC TTA TTG CTT GGA ACA TTA TTA ATA TCA CAC CAA AGA ATG AAA
--- --- --- --- --- --- --- --- --- --- --- --- --- --- --- --- --- ---
 S   S   S   I   L   L   L   G   T   L   L   I   S   H   Q   R   M   K 2709           2718           2727           2736           2745           2754
AAG CTA TTT TGG GAA GAT GTT CCG AAC CCC AAG AAT TGT TCC TGG GCA CAA GGA
--- --- --- --- --- --- --- --- --- --- --- --- --- --- --- --- --- ---
 K   L   F   W   E   D   V   P   N   P   K   N   C   S   W   A   Q   G 2763           2772           2781           2790           2799           2808
CTT AAT TTT CAG AAG ATG CTT GAA GGC AGC ATG TTC GTT AAG AGT CAT CAC CAC
--- --- --- --- --- --- --- --- --- --- --- --- --- --- --- --- --- ---
 L   N   F   Q   K   M   L   E   G   S   M   F   V   K   S   H   H   H 2817           2826           2835           2844           2853           2862
TCC CTA ATC TCA AGT ACC CAG GGA CAC AAA CAC TGC GGA AGG CCA CAG GGT CCT
--- --- --- --- --- --- --- --- --- --- --- --- --- --- --- --- --- ---
 S   L   I   S   S   T   Q   G   H   K   H   C   G   R   P   Q   G   P 2871           2880           2889           2898           2907           2916
CTG CAT AGG AAA ACC AGA GAC CTT TGT TCA CTT GTT TAT CTG CTG ACC CTC CCT
--- --- --- --- --- --- --- --- --- --- --- --- --- --- --- --- --- ---
 L   H   R   K   T   R   D   L   C   S   L   V   Y   L   L   T   L   P 2925           2934           2943           2952           2961           2970
CCA CTA TTG TCC TAT GAC CCT GCC AAA TCC CCC TCT GTG AGA AAC ACC CAA GAA
--- --- --- --- --- --- --- --- --- --- --- --- --- --- --- --- --- ---
 P   L   L   S   Y   D   P   A   K   S   P   S   V   R   N   T   Q   E 2979           2988
TGA TCA ATA AAA AAA AAA AAA 3'
--- --- --- --- --- --- ---
 *   S   I   K   K   K   K
```

FIG.1G

| | | | 2760 | 2770 | 2780 | 2790 | 2800 | |
|---|---|---|---|---|---|---|---|---|
| HuB1.219 | FORM | 1 | 2751 | AGGACTTAAT | TTTCAGAAGA | TGCTTGAAGG | CAGCATGTTC | GTTAAGAGTC | 2800 |
| HuB1.219 | | 2 | 2751 | AGGACTTAAT | TTTCAGAAGA | AAATGCCTGG | CACAAAGGAA | CTACTGGGTG | 2800 |
| HuB1.219 | | 3 | 2751 | AGGACTTAAT | TTTCAGAAGA | GAACGGACAT | TCTTTGAAGT | CTAATCATGA | 2800 |

| | | | | 2810 | 2820 | 2830 | 2840 | 2850 | |
|---|---|---|---|---|---|---|---|---|---|
| HuB1.219 | FORM | 1 | 2801 | ATCACCACTC | CCTAATCTCA | AGTACCCAGG | GACACAAACA | CTGCGGAAGG | 2850 |
| HuB1.219 | | 2 | 2801 | GAGGTTGGTT | GACTTAGGAA | ATGCTTGTGA | AGCTACGTCC | TACCTCGTGC | 2850 |
| HuB1.219 | | 3 | 2801 | TCACTACAGA | TGAACCCAAT | GTGCCAACTT | CCCAACAGTC | TATAGAGTAT | 2850 |

| | | | | 2860 | 2870 | 2880 | 2890 | 2900 | |
|---|---|---|---|---|---|---|---|---|---|
| HuB1.219 | FORM | 1 | 2851 | CCACAGGGTC | CTCTGCATAG | GAAAACCAGA | GACCTTTGTT | CACTTGTTTA | 2900 |
| HuB1.219 | | 2 | 2851 | GCACCTGCTC | TCCCTGAGGT | GTGCACAATG | .......... | .......... | 2900 |
| HuB1.219 | | 3 | 2851 | TAGAAGATTT | TTACATTCTG | AAGAAGG... | .......... | .......... | 2900 |

| | | | | 2910 | 2920 | 2930 | 2940 | 2950 | |
|---|---|---|---|---|---|---|---|---|---|
| HuB1.219 | FORM | 1 | 2901 | TCTGCTGACC | CTCCCTCCAC | TATTGTCCTA | TGACCCTGCC | AAATCCCCCT | 2950 |
| HuB1.219 | | 2 | 2901 | .......... | .......... | .......... | .......... | .......... | 2950 |
| HuB1.219 | | 3 | 2901 | .......... | .......... | .......... | .......... | .......... | 2950 |

| | | | | 2960 | 2970 | 2980 | 2990 | 3000 | |
|---|---|---|---|---|---|---|---|---|---|
| HuB1.219 | FORM | 1 | 2951 | CTGTGAGAAA | CACCCAAGAA | TGATCAATAA | AAAAAAAAA | A......... | 3000 |
| HuB1.219 | | 2 | 2951 | .......... | .......... | .......... | .......... | .......... | 3000 |
| HuB1.219 | | 3 | 2951 | .......... | .......... | .......... | .......... | .......... | 3000 |

FIG.2

```
              10          20          30          40          50
HuB1.219_1   1  MICQKFCVVL  LHWEFIYVIT  AFNLSYPITP  WRFKLSCMPP  NSTYDYFLLP   50
HuB1.219_2   1  MICQKFCVVL  LHWEFIYVIT  AFNLSYPITP  WRFKLSCMPP  NSTYDYFLLP   50
HuB1.219_3   1  MICQKFCVVL  LHWEFIYVIT  AFNLSYPITP  WRFKLSCMPP  NSTYDYFLLP   50
HuOBR        1  MICQKFCVVL  LHWEFIYVIT  AFNLSYPITP  WRFKLSCMPP  NSTYDYFLLP   50
MuOBR        1  MVCQKFTVVL  LHWEFLYVIA  ADNLAYPISP  WRFKLFCGPP  NTDDSELSP    50

60          70          80          90         100
HuB1.219_1  51  AGLSKNTSNS  NGHYETAVEP  KFNSSGTHFS  NLSKATFHCC  FRSEQDRNCS  100
HuB1.219_2  51  AGLSKNTSNS  NGHYETAVEP  KFNSSGTHFS  NLSKATFHCC  FRSEQDRNCS  100
HuB1.219_3  51  AGLSKNTSNS  NGHYETAVEP  KFNSSGTHFS  NLSKATFHCC  FRSEQDRNCS  100
HuOBR       51  AGLSKNTSNS  NGHYETAVEP  KFNSSGTHFS  NLSKTTFHCC  FRSEQDRNCS  100
MuOBR       51  AGAPNVASAL  RQASEATVEA  KFNSSGITYP  ELSKITVFHCC EGNEQCQNCS  100

110         120         130         140         150
HuB1.219_1 101  LCADNIEGRT  FVSTVNSLVF  QQIDANWNIQ  CWLKGDLKLF  ICYVESLFKN  150
HuB1.219_2 101  LCADNIEGRT  FVSTVNSLVF  QQIDANWNIQ  CWLKGDLKLF  ICYVESLFKN  150
HuB1.219_3 101  LCADNIEGRT  FVSTVNSLVF  QQIDANWNIQ  CWLKGDLKLF  ICYVESLFKN  150
HuOBR      101  LCADNIEGKT  FVSTVNSLVF  QQIDANWNIQ  CWLKGDLKLF  ICYVESLFKN  150
MuOBR      101  ALTDNTEGKT  LASVVKASVF  RQLGVNMDIE  CMWKGDLTLF  ICFMEPLPKN  150

160         170         180         190         200
HuB1.219_1 151  LFRNYNYKVH  LLYVLPEVLE  DSPLVPQKGS  FQMVHCNCSV  HECCECLVPV  200
HuB1.219_2 151  LFRNYNYKVH  LLYVLPEVLE  DSPLVPQKGS  FQMVHCNCSV  HECCECLVPV  200
HuB1.219_3 151  LFRNYNYKVH  LLYVLPEVLE  DSPLVPQKGS  FQMVHCNCSV  HECCECLVPV  200
HuOBR      151  LFRNYNYKVH  LLYVLPEVLE  DSPLVPQKGS  FQMVHCNCSV  HECCECLVPV  200
MuOBR      151  PFKNYDSKVH  LLYDLPEVID  DSPLPPDLDS  FQTMQCNCSI  RGCEGFVPV   200
```

FIG.3A

```
                     210        220        230        240        250
HuB1.219_1  201  PTAKLNDTLL MCLKITSGGV IFRSPLMSVQ PINMVKPDPP LGLHMEITDD  250
HuB1.219_2  201  PTAKLNDTLL MCLKITSGGV IFRSPLMSVQ PINMVKPDPP LGLHMEITDD  250
HuB1.219_3  201  PTAKLNDTLL MCLKITSGGV IFRSPLMSVQ PINMVKPDPP LGLHMEITDD  250
HuOBR       201  PTAKLNDTLL MCLKITSGGV IFQSPLMSVQ PINMVKPDPP LGLHMEITDD  250
MuOBR       201  PRAKLNYALL MYLEITSAGV SFQSPLMSLQ PMLVVKPDPP LGLHMEVTDD  250

260        270        280        290        300
HuB1.219_1  251  GNLKISWSSP PLVPFPLQYQ VKYSENSTTV IREADKIVSA TSLLVDSILP  300
HuB1.219_2  251  GNLKISWSSP PLVPFPLQYQ VKYSENSTTV IREADKIVSA TSLLVDSILP  300
HuB1.219_3  251  GNLKISWSSP PLVPFPLQYQ VKYSENSTTV IREADKIVSA TSLLVDSILP  300
HuOBR       251  GNLKISWSSP PLVPFPLQYQ VKYSENSTTV IREADKIVSA TSLLVDSILP  300
MuOBR       251  GNLKISWDSQ TMAPFPLQYQ VKYIENSTIV REAAFEIVSA TSLLVDSMLP  300

310        320        330        340        350
HuB1.219_1  301  GSSYEVQVRG KRLDGPGIWS DWSTPRVFTT QDVIYFPPKI LTSVGSNVSF  350
HuB1.219_2  301  GSSYEVQVRG KRLDGPGIWS DWSTPRVFTT QDVIYFPPKI TSVGSNVSF   350
HuB1.219_3  301  GSSYEVQVRG KRLDGPGIWS DWSTPRVFTT QDVIYFPPKI TSVGSNVSF   350
HuOBR       301  GSSYEVQVRG KRLDGPGIWS DWSTPRVFTT QDVIYFPPKI TSVGSNVSF   350
MuOBR       301  GSSYEVQVRS KRLDGSGWMS DWSSPQVFTI QDVWYFPPKI LTSVGSNASF  350

360        370        380        390        400
HuB1.219_1  351  HCIYKKENKI VPSKEIVWWM NLAEKIPQSQ YDVVSDHVSK VTFFNLNETK  400
HuB1.219_2  351  HCIYKKENKI VPSKEIVWWM NLAEKIPQSQ YDVVSDHVSK VTFFNLNETK  400
HuB1.219_3  351  HCIYKKENKI VPSKEIVWWM NLAEKIPQSQ YDVVSDHVSK VTFFNLNETK  400
HuOBR       351  HCIYKKENKI VPSKEIVWWM NLAEKIPQSQ YDVVSDHVSK VTFFNLNETK  400
MuOBR       351  HCIYKNENQI TSSKQIVWWR NLAEKIPETQ YSTVSDRVSK VTFSNLKATR  400
```

FIG.3B

```
                   410         420         430         440         450
HuB1.219_1  401  PRGKFTYDAV  YCCNEHECHH  RYAELYVIDV  NINISCETDG  YLTKMTCRWS  450
HuB1.219_2  401  PRGKFTYDAV  YCCNEHECHH  RYAELYVIDV  NINISCETDG  YLTKMTCRWS  450
HuB1.219_3  401  PRGKFTYDAV  YCCNEHECHH  RYAELYVIDV  NINISCETDG  YLTKMTCRWS  450
HuOBR       401  PRGKFTYDAV  YCCNEHECHH  RYAELYVIDV  NINISCETDG  YLTKMTCRWS  450
MuOBR       401  PRGKFTYDAV  YCCNEQACHH  RYAELYVIDV  NINISCETDG  YLTKMTCRWS  450

460         470         480         490         500
HuB1.219_1  451  TSTIQSLAES  TLQLRYHRSS  LYCSDIPSIH  PISEPKDCYL  QSDGFYECIF  500
HuB1.219_2  451  TSTIQSLAES  TLQLRYHRSS  LYCSDIPSIH  PISEPKDCYL  QSDGFYECIF  500
HuB1.219_3  451  TSTIQSLAES  TLQLRYHRSS  LYCSDIPSIH  PISEPKDCYL  QSDGFYECIF  500
HuOBR       451  TSTIQSLAES  TLQLRYHRSS  LYCSDIPSIH  PISEPKDCYL  QSDGFYECIF  500
MuOBR       451  PSTIQSLVGS  TQLRYHRS    LYCPDSPSIH  PTSEPKNQVL  QRDGFYECVE  500

510         520         530         540         550
HuB1.219_1  501  QPIFLLSGYT  MWIRINHSLG  SLDSPPTCVL  PDSVVKPLPP  SSVKAEITIN  550
HuB1.219_2  501  QPIFLLSGYT  MWIRINHSLG  SLDSPPTCVL  PDSVVKPLPP  SSVKAEITIN  550
HuB1.219_3  501  QPIFLLSGYT  MWIRINHSLG  SLDSPPTCVL  PDSVVKPLPP  SSVKAEITIN  550
HuOBR       501  QPIFLLSGYT  MWIRINHSLG  SLDSPPTCVL  PDSVVKPLPP  SSVKAEITIN  550
MuOBR       501  QPIFLLSGYT  MWIRINHSLG  SLDSPPTCVL  PDSVVKPLPP  SVKAEITTVN  550

560         570         580         590         600
HuB1.219_1  551  IGLLKISWEK  PVFPENNLQF  QIRYGLSGKE  VQWKMYEVYD  AKSKSVSLPV  600
HuB1.219_2  551  IGLLKISWEK  PVFPENNLQF  QIRYGLSGKE  VQWKMYEVYD  AKSKSVSLPV  600
HuB1.219_3  551  IGLLKISWEK  PVFPENNLQF  QIRYGLSGKE  VQWKMYEVYD  AKSKSVSLPV  600
HuOBR       551  IGLLKISWEK  PVFPENNLQF  QIRYGLSGKE  VQWKMYEVYD  AKSKSVSLPV  600
MuOBR       551  TGLLKVSWEK  PVFPENNLQF  QIRYGLSGKE  TQWKTHEVFD  AKSKSASLIV  600
```

FIG.3C

| | | 610 | 620 | 630 | 640 | 650 | |
|---|---|---|---|---|---|---|---|
| HuB1.219_1 | 601 | PDLCAVYAVQ | VRCKRLDGLG | YWSNWSNPAY | TVVMDIKVPM | RGPEFWRIIN | 650 |
| HuB1.219_2 | 601 | PDLCAVYAVQ | VRCKRLDGLG | YWSNWSNPAY | TVVMDIKVPM | RGPEFWRIIN | 650 |
| HuB1.219_3 | 601 | PDLCAVYAVQ | VRCKRLDGLG | YWSNWSNPAY | TVVMDIKVPM | RGPEFWRIIN | 650 |
| HuOBR | 601 | PDLCAVYAVQ | VRCKRLDGLG | YWSNWSNPAY | TVVMDIKVPM | RGPEFWRIIN | 650 |
| MuOBR | 601 | SDLCAVYMVQ | VRCRLDGLG | YWSNWSSPAY | TLVMDVKVPM | RGPEFWRKMD | 650 |

| | | 660 | 670 | 680 | 690 | 700 | |
|---|---|---|---|---|---|---|---|
| HuB1.219_1 | 651 | GDTMKKEKNV | TLLWKPLMKN | DSLCSVQRYV | INHHTSCNGT | WSEDVGNHTK | 700 |
| HuB1.219_2 | 651 | GDTMKKEKNV | TLLWKPLMKN | DSLCSVQRYV | INHHTSCNGT | WSEDVGNHTK | 700 |
| HuB1.219_3 | 651 | GDTMKKEKNV | TLLWKPLMKN | DSLCSVQRYV | INHHTSCNGT | WSEDVGNHTK | 700 |
| HuOBR | 651 | GDTMKKEKNV | TLLWKPLMKN | DSLCSVQRYV | INHHTSCNGT | WSEDVGNHTK | 700 |
| MuOBR | 651 | GDVTKKERNV | ILLWKPLTKN | VKQRTAHNGT | | WSEDVGNRTN | 700 |

| | | 710 | 720 | 730 | 740 | 750 | |
|---|---|---|---|---|---|---|---|
| HuB1.219_1 | 701 | FTFLWTEQAH | TVTVLAINSI | GASVANFNLT | FSWPMSKVNI | VQSLSAYPLN | 750 |
| HuB1.219_2 | 701 | FTFLWTEQAH | TVTVLAINSI | GASVANFNLT | FSWPMSKVNI | VQSLSAYPLN | 750 |
| HuB1.219_3 | 701 | FTFLWTEQAH | TVTVLAINSI | GASVANFNLT | FSWPMSKVNI | VQSLSAYPLN | 750 |
| HuOBR | 701 | FTFLWTEQAH | TVTVLAINSI | GASVANFNLT | FSWPMSKVNI | VQSLSAYPLN | 750 |
| MuOBR | 701 | LTFLWTEPAH | TVTVLAVNSI | GASVANFNLT | FSWPMSKVSA | VESLSAYPLS | 750 |

| | | 760 | 770 | 780 | 790 | 800 | |
|---|---|---|---|---|---|---|---|
| HuB1.219_1 | 751 | SSCVIVSWIL | SPSDYKLMYF | IIEWKNLNED | GEIKWLRISS | SVKKYYIHDH | 800 |
| HuB1.219_2 | 751 | SSCVIVSWIL | SPSDYKLMYF | IIEWKNLNED | GEIKWLRISS | SVKKYYIHDH | 800 |
| HuB1.219_3 | 751 | SSCVIVSWIL | SPSDYKLMYF | IIEWKNLNED | GEIKWLRISS | SVKKYYIHDH | 800 |
| HuOBR | 751 | SSCVIVSWIL | SPSDYKLMYF | IIEWKNLNED | GEIKWLRISS | SVKKYYIHDH | 800 |
| MuOBR | 751 | SSCVISWIL | SPDDYSLLM | VIEWKNLNED | DGMKWLRIPS | NVKKFYIHDN | 800 |

FIG. 3D

```
HuB1.219_1  801  FIPIEKYQFS LYPIFMEGVG KPKIINSFTQ DDIEKHQSDA GLYVIVPVII  850
HuB1.219_2  801  FIPIEKYQFS LYPIFMEGVG KPKIINSFTQ DDIEKHQSDA GLYVIVPVII  850
HuB1.219_3  801  FIPIEKYQFS LYPIFMEGVG KPKIINSFTQ DDIEKHQSDA GLYVIVPVII  850
HuOBR       801  FIPIEKYQFS LYPIFMEGVG KPKIINSFTQ DDIEKHQSDA GLYVIVPVII  850
MuOBR       801  FIPIEKYQFS LYPVMEGVG  KPKIINGFIK DAIDKQQNDA GLYVIVPILI  850

HuB1.219_1  851  SSSILLLGTL LISHQRMKKL FWEDVPNPKN CSWAQGLNFQ KMLEGSMFVK  900
HuB1.219_2  851  SSSILLLGTL LISHQRMKKL FWEDVPNPKN CSWAQGLNFQ KKMPGTKELL  900
HuB1.219_3  851  SSSILLLGTL LISHQRMKKL FWEDVPNPKN CSWAQGLNFQ KRTDIL...  900
HuOBR       851  SSSILLLGTL LISHQRMKKL FWEDVPNPKN CSWAQGLNFQ KPETFEHLFI  900
MuOBR       851  SSCVLLLGTL LISHQRMKKL FWDDVPNPKN CSWAQGLNFQ KRTDTL*...  900

HuB1.219_1  901  SHHSLISST  QGHKHCGRPQ GPLHRKTRDL CSLVYLLLP  PLLSYDPAKS  950
HuB1.219_2  901  GGGWLT...                                            950
HuB1.219_3  901  ..........                                           950
HuOBR       901  KHTASVTCGP LLLEPETISE DISVDTSWKN KDEMMPTIWV SLLSTTDLEK  950
MuOBR       901  ..........                                           950

HuB1.219_1  951  PSVRNTQE..                                           1000
HuB1.219_2  951  ..........                                           1000
HuB1.219_3  951  ..........                                           1000
HuOBR       951  GSVCISDQFN SVNFSEAEGT EVTYEAESQR QPFVKYATLI SNSKPSETGE  1000
MuOBR       951  ..........                                           1000
```

FIG.3E

```
HuB1.219_1   1001                                                                            1050
HuB1.219_2   1001  ........................................................................ 1050
HuB1.219_3   1001  ........................................................................ 1050
HuOBR        1001  EQGLINSSVT KCFSSKNSPL KDSFSNSSWE IEAQAFFILS DQHPNIISPH                    1050
MuOBR        1001  ........................................................................ 1050

1010       1020       1030       1040       1050

HuB1.219_1   1051                                                                            1100
HuB1.219_2   1051  ........................................................................ 1100
HuB1.219_3   1051  ........................................................................ 1100
HuOBR        1051  LTFSEGIDEL LKLEGNFPEE NNDKKSIYYL GVTSIKKRES GVLLTDKSRV                    1100
MuOBR        1051  ........................................................................ 1100

1060       1070       1080       1090       1100

HuB1.219_1   1101                                                                            1150
HuB1.219_1   1101  ........................................................................ 1150
HuB1.219_1   1101  ........................................................................ 1150
HuOBR        1101  SCPFPAPCLF TDIRVLQDSC SHFVENNINL GTSSKKTFAS YMPQFQTCST                    1150
MuOBR        1101  ........................................................................ 1150

1110       1120       1130       1140       1150

HuB1.219_1   1151                                                                            1200
HuB1.219_1   1151  ........................................................................ 1200
HuB1.219_1   1151  ........................................................................ 1200
HuOBR        1151  QTHKIMENKM CDLTV*.....                                                    1200
MuOBR        1151  ........................................................................ 1200

1160       1170       1180       1190       1200
```

FIG.3F

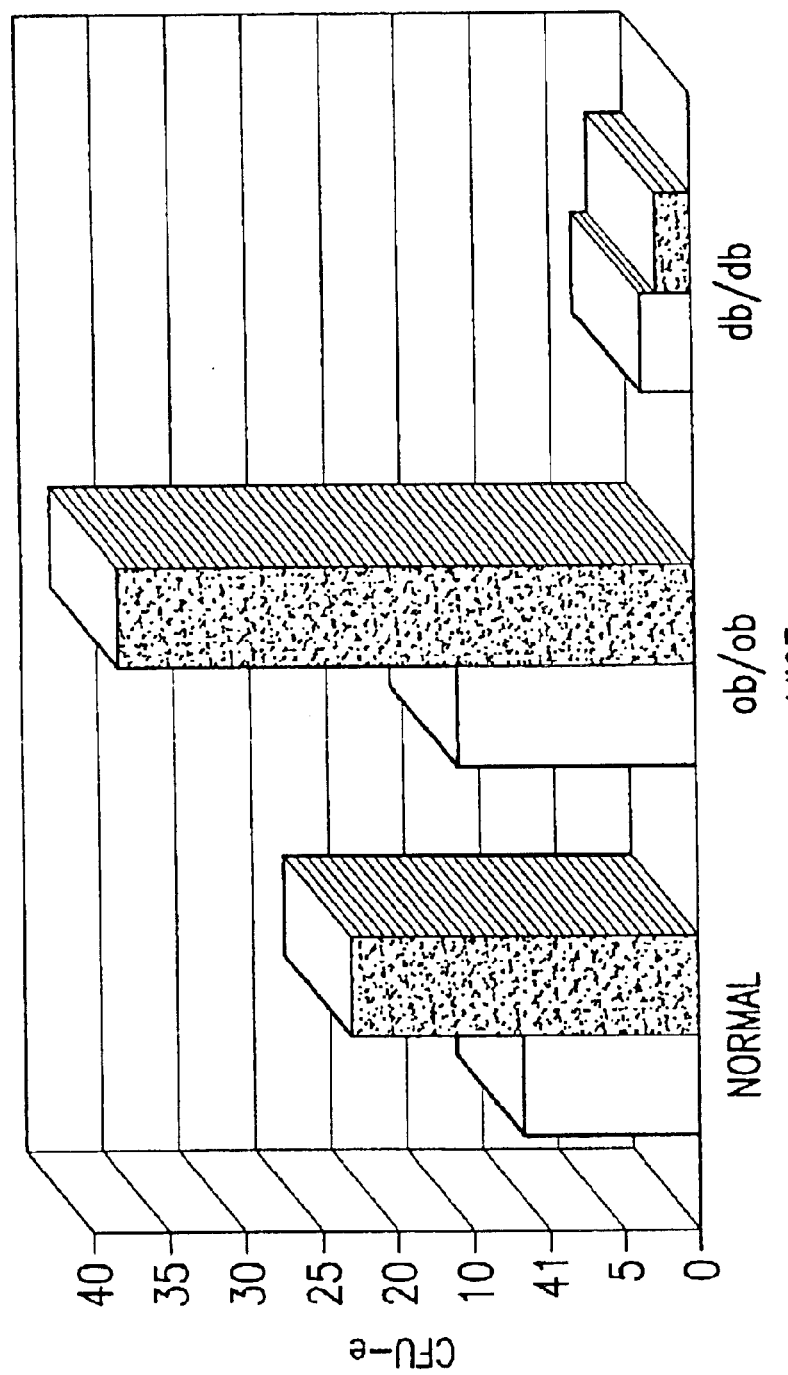

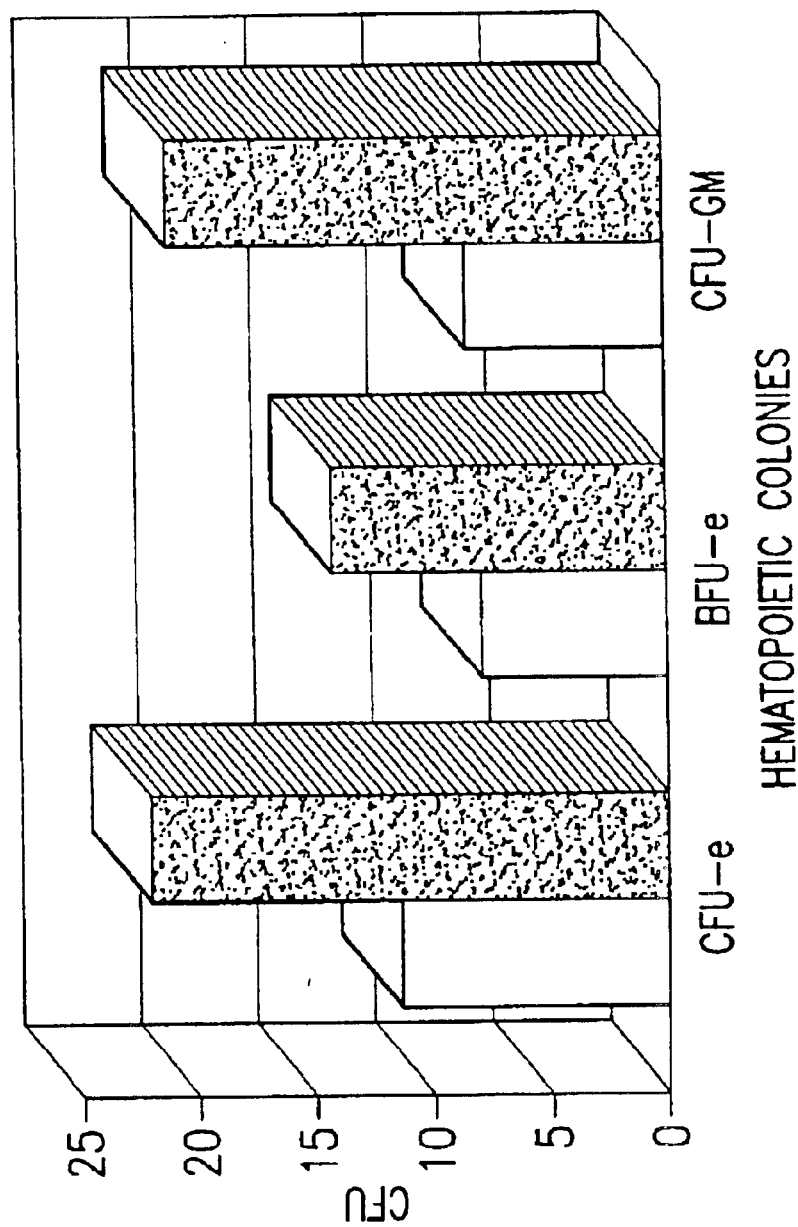

SEQUENCE LISTING (1) GENERAL INFORMATION:

(iii) NUMBER OF SEQUENCES: 28

(2) INFORMATION FOR SEQ ID NO: 1:

(i) SEQUENCE CHARACTERISTICS:
      (A) LENGTH: 2991 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 1..2991

(xi) SEQUENCE DESCRIPTION: SEQ ID NO: 1:

```
GCG CGC GCG ACG CAG GTG CCC GAG CCC CGG CCC GCG CCC ATC TCT GCC      48
Ala Arg Ala Thr Gln Val Pro Glu Pro Arg Pro Ala Pro Ile Ser Ala
 1               5                  10                  15

TTC GGT CGA GTT GGA CCC CCG GAT CAA GGT GTA CTT CTC TGA AGT AAG      96
Phe Gly Arg Val Gly Pro Pro Asp Gln Gly Val Leu Leu  *  Ser Lys
                20                  25                  30

ATG ATT TGT CAA AAA TTC TGT GTG GTT TTG TTA CAT TGG GAA TTT ATT     144
Met Ile Cys Gln Lys Phe Cys Val Val Leu Leu His Trp Glu Phe Ile
         35                  40                  45

TAT GTG ATA ACT GCG TTT AAC TTG TCA TAT CCA ATT ACT CCT TGG AGA     192
Tyr Val Ile Thr Ala Phe Asn Leu Ser Tyr Pro Ile Thr Pro Trp Arg
     50                  55                  60

TTT AAG TTG TCT TGC ATG CCA CCA AAT TCA ACC TAT GAC TAC TTC CTT     240
Phe Lys Leu Ser Cys Met Pro Pro Asn Ser Thr Tyr Asp Tyr Phe Leu
 65                  70                  75                  80

TTG CCT GCT GGA CTC TCA AAG AAT ACT TCA AAT TCG AAT GGA CAT TAT     288
Leu Pro Ala Gly Leu Ser Lys Asn Thr Ser Asn Ser Asn Gly His Tyr
                 85                  90                  95

GAG ACA GCT GTT GAA CCT AAG TTT AAT TCA AGT GGT ACT CAC TTT TCT     336
Glu Thr Ala Val Glu Pro Lys Phe Asn Ser Ser Gly Thr His Phe Ser
                100                 105                 110

AAC TTA TCC AAA GCA ACT TTC CAC TGT TGC TTT CGG AGT GAG CAA GAT     384
Asn Leu Ser Lys Ala Thr Phe His Cys Cys Phe Arg Ser Glu Gln Asp
            115                 120                 125

AGA AAC TGC TCC TTA TGT GCA GAC AAC ATT GAA GGA AGG ACA TTT GTT     432
Arg Asn Cys Ser Leu Cys Ala Asp Asn Ile Glu Gly Arg Thr Phe Val
        130                 135                 140

TCA ACA GTA AAT TCT TTA GTT TTT CAA CAA ATA GAT GCA AAC TGG AAC     480
Ser Thr Val Asn Ser Leu Val Phe Gln Gln Ile Asp Ala Asn Trp Asn
145                 150                 155                 160

ATA CAG TGC TGG CTA AAA GGA GAC TTA AAA TTA TTC ATC TGT TAT GTG     528
Ile Gln Cys Trp Leu Lys Gly Asp Leu Lys Leu Phe Ile Cys Tyr Val
                165                 170                 175

GAG TCA TTA TTT AAG AAT CTA TTC AGG AAT TAT AAC TAT AAG GTC CAT     576
Glu Ser Leu Phe Lys Asn Leu Phe Arg Asn Tyr Asn Tyr Lys Val His
                180                 185                 190

CTT TTA TAT GTT CTG CCT GAA GTG TTA GAA GAT TCA CCT CTG GTT CCC     624
Leu Leu Tyr Val Leu Pro Glu Val Leu Glu Asp Ser Pro Leu Val Pro
            195                 200                 205

CAA AAA GGC AGT TTT CAG ATG GTT CAC TGC AAT TGC AGT GTT CAT GAA     672
Gln Lys Gly Ser Phe Gln Met Val His Cys Asn Cys Ser Val His Glu
        210                 215                 220
```

```
TGT TGT GAA TGT CTT GTG CCT GTG CCA ACA GCC AAA CTC AAC GAC ACT      720
Cys Cys Glu Cys Leu Val Pro Val Pro Thr Ala Lys Leu Asn Asp Thr
225                 230                 235                 240

CTC CTT ATG TGT TTG AAA ATC ACA TCT GGT GGA GTA ATT TTC CGG TCA      768
Leu Leu Met Cys Leu Lys Ile Thr Ser Gly Gly Val Ile Phe Arg Ser
                245                 250                 255

CCT CTA ATG TCA GTT CAG CCC ATA AAT ATG GTG AAG CCT GAT CCA CCA      816
Pro Leu Met Ser Val Gln Pro Ile Asn Met Val Lys Pro Asp Pro Pro
            260                 265                 270

TTA GGT TTG CAT ATG GAA ATC ACA GAT GAT GGT AAT TTA AAG ATT TCT      864
Leu Gly Leu His Met Glu Ile Thr Asp Asp Gly Asn Leu Lys Ile Ser
        275                 280                 285

TGG TCC AGC CCA CCA TTG GTA CCA TTT CCA CTT CAA TAT CAA GTG AAA      912
Trp Ser Ser Pro Pro Leu Val Pro Phe Pro Leu Gln Tyr Gln Val Lys
290                 295                 300

TAT TCA GAG AAT TCT ACA ACA GTT ATC AGA GAA GCT GAC AAG ATT GTC      960
Tyr Ser Glu Asn Ser Thr Thr Val Ile Arg Glu Ala Asp Lys Ile Val
305                 310                 315                 320

TCA GCT ACA TCC CTG CTA GTA GAC AGT ATA CTT CCT GGG TCT TCG TAT     1008
Ser Ala Thr Ser Leu Leu Val Asp Ser Ile Leu Pro Gly Ser Ser Tyr
                325                 330                 335

GAG GTT CAG GTG AGG GGC AAG AGA CTG GAT GGC CCA GGA ATC TGG AGT     1056
Glu Val Gln Val Arg Gly Lys Arg Leu Asp Gly Pro Gly Ile Trp Ser
            340                 345                 350

GAC TGG AGT ACT CCT CGT GTC TTT ACC ACA CAA GAT GTC ATA TAC TTT     1104
Asp Trp Ser Thr Pro Arg Val Phe Thr Thr Gln Asp Val Ile Tyr Phe
        355                 360                 365

CCA CCT AAA ATT CTG ACA AGT GTT GGG TCT AAT GTT TCT TTT CAC TGC     1152
Pro Pro Lys Ile Leu Thr Ser Val Gly Ser Asn Val Ser Phe His Cys
370                 375                 380

ATC TAT AAG AAG GAA AAC AAG ATT GTT CCC TCA AAA GAG ATT GTT TGG     1200
Ile Tyr Lys Lys Glu Asn Lys Ile Val Pro Ser Lys Glu Ile Val Trp
385                 390                 395                 400

TGG ATG AAT TTA GCT GAG AAA ATT CCT CAA AGC CAG TAT GAT GTT GTG     1248
Trp Met Asn Leu Ala Glu Lys Ile Pro Gln Ser Gln Tyr Asp Val Val
                405                 410                 415

AGT GAT CAT GTT AGC AAA GTT ACT TTT TTC AAT CTG AAT GAA ACC AAA     1296
Ser Asp His Val Ser Lys Val Thr Phe Phe Asn Leu Asn Glu Thr Lys
            420                 425                 430

CCT CGA GGA AAG TTT ACC TAT GAT GCA GTG TAC TGC TGC AAT GAA CAT     1344
Pro Arg Gly Lys Phe Thr Tyr Asp Ala Val Tyr Cys Cys Asn Glu His
        435                 440                 445

GAA TGC CAT CAT CGC TAT GCT GAA TTA TAT GTG ATT GAT GTC AAT ATC     1392
Glu Cys His His Arg Tyr Ala Glu Leu Tyr Val Ile Asp Val Asn Ile
450                 455                 460

AAT ATC TCA TGT GAA ACT GAT GGG TAC TTA ACT AAA ATG ACT TGC AGA     1440
Asn Ile Ser Cys Glu Thr Asp Gly Tyr Leu Thr Lys Met Thr Cys Arg
465                 470                 475                 480

TGG TCA ACC AGT ACA ATC CAG TCA CTT GCG GAA AGC ACT TTG CAA TTG     1488
Trp Ser Thr Ser Thr Ile Gln Ser Leu Ala Glu Ser Thr Leu Gln Leu
                485                 490                 495

AGG TAT CAT AGG AGC AGC CTT TAC TGT TCT GAT ATT CCA TCT ATT CAT     1536
Arg Tyr His Arg Ser Ser Leu Tyr Cys Ser Asp Ile Pro Ser Ile His
            500                 505                 510

CCC ATA TCT GAG CCC AAA GAT TGC TAT TTG CAG AGT GAT GGT TTT TAT     1584
Pro Ile Ser Glu Pro Lys Asp Cys Tyr Leu Gln Ser Asp Gly Phe Tyr
        515                 520                 525

GAA TGC ATT TTC CAG CCA ATC TTC CTA TTA TCT GGC TAC ACA ATG TGG     1632
Glu Cys Ile Phe Gln Pro Ile Phe Leu Leu Ser Gly Tyr Thr Met Trp
```

-continued

```
            530                 535                 540
ATT AGG ATC AAT CAC TCT CTA GGT TCA CTT GAC TCT CCA CCA ACA TGT    1680
Ile Arg Ile Asn His Ser Leu Gly Ser Leu Asp Ser Pro Pro Thr Cys
545                 550                 555                 560

GTC CTT CCT GAT TCT GTG GTG AAG CCA CTG CCT CCA TCC AGT GTG AAA    1728
Val Leu Pro Asp Ser Val Val Lys Pro Leu Pro Pro Ser Ser Val Lys
                565                 570                 575

GCA GAA ATT ACT ATA AAC ATT GGA TTA TTG AAA ATA TCT TGG GAA AAG    1776
Ala Glu Ile Thr Ile Asn Ile Gly Leu Leu Lys Ile Ser Trp Glu Lys
            580                 585                 590

CCA GTC TTT CCA GAG AAT AAC CTT CAA TTC CAG ATT CGC TAT GGT TTA    1824
Pro Val Phe Pro Glu Asn Asn Leu Gln Phe Gln Ile Arg Tyr Gly Leu
        595                 600                 605

AGT GGA AAA GAA GTA CAA TGG AAG ATG TAT GAG GTT TAT GAT GCA AAA    1872
Ser Gly Lys Glu Val Gln Trp Lys Met Tyr Glu Val Tyr Asp Ala Lys
    610                 615                 620

TCA AAA TCT GTC AGT CTC CCA GTT CCA GAC TTG TGT GCA GTC TAT GCT    1920
Ser Lys Ser Val Ser Leu Pro Val Pro Asp Leu Cys Ala Val Tyr Ala
625                 630                 635                 640

GTT CAG GTG CGC TGT AAG AGG CTA GAT GGA CTG GGA TAT TGG AGT AAT    1968
Val Gln Val Arg Cys Lys Arg Leu Asp Gly Leu Gly Tyr Trp Ser Asn
                645                 650                 655

TGG AGC AAT CCA GCC TAC ACA GTT GTC ATG GAT ATA AAA GTT CCT ATG    2016
Trp Ser Asn Pro Ala Tyr Thr Val Val Met Asp Ile Lys Val Pro Met
            660                 665                 670

AGA GGA CCT GAA TTT TGG AGA ATA ATT AAT GGA GAT ACT ATG AAA AAG    2064
Arg Gly Pro Glu Phe Trp Arg Ile Ile Asn Gly Asp Thr Met Lys Lys
        675                 680                 685

GAG AAA AAT GTC ACT TTA CTT TGG AAG CCC CTG ATG AAA AAT GAC TCA    2112
Glu Lys Asn Val Thr Leu Leu Trp Lys Pro Leu Met Lys Asn Asp Ser
    690                 695                 700

TTG TGC AGT GTT CAG AGA TAT GTG ATA AAC CAT CAT ACT TCC TGC AAT    2160
Leu Cys Ser Val Gln Arg Tyr Val Ile Asn His His Thr Ser Cys Asn
705                 710                 715                 720

GGA ACA TGG TCA GAA GAT GTG GGA AAT CAC ACG AAA TTC ACT TTC CTG    2208
Gly Thr Trp Ser Glu Asp Val Gly Asn His Thr Lys Phe Thr Phe Leu
                725                 730                 735

TGG ACA GAG CAA GCA CAT ACT GTT ACG GTT CTG GCC ATC AAT TCA ATT    2256
Trp Thr Glu Gln Ala His Thr Val Thr Val Leu Ala Ile Asn Ser Ile
            740                 745                 750

GGT GCT TCT GTT GCA AAT TTT AAT TTA ACC TTT TCA TGG CCT ATG AGC    2304
Gly Ala Ser Val Ala Asn Phe Asn Leu Thr Phe Ser Trp Pro Met Ser
        755                 760                 765

AAA GTA AAT ATC GTG CAG TCA CTC AGT GCT TAT CCT TTA AAC AGC AGT    2352
Lys Val Asn Ile Val Gln Ser Leu Ser Ala Tyr Pro Leu Asn Ser Ser
    770                 775                 780

TGT GTG ATT GTT TCC TGG ATA CTA TCA CCC AGT GAT TAC AAG CTA ATG    2400
Cys Val Ile Val Ser Trp Ile Leu Ser Pro Ser Asp Tyr Lys Leu Met
785                 790                 795                 800

TAT TTT ATT ATT GAG TGG AAA AAT CTT AAT GAA GAT GGT GAA ATA AAA    2448
Tyr Phe Ile Ile Glu Trp Lys Asn Leu Asn Glu Asp Gly Glu Ile Lys
                805                 810                 815

TGG CTT AGA ATC TCT TCA TCT GTT AAG AAG TAT TAT ATC CAT GAT CAT    2496
Trp Leu Arg Ile Ser Ser Ser Val Lys Lys Tyr Tyr Ile His Asp His
            820                 825                 830

TTT ATC CCC ATT GAG AAG TAC CAG TTC AGT CTT TAC CCA ATA TTT ATG    2544
Phe Ile Pro Ile Glu Lys Tyr Gln Phe Ser Leu Tyr Pro Ile Phe Met
        835                 840                 845

GAA GGA GTG GGA AAA CCA AAG ATA ATT AAT AGT TTC ACT CAA GAT GAT    2592
```

```
Glu Gly Val Gly Lys Pro Lys Ile Ile Asn Ser Phe Thr Gln Asp Asp
    850                 855                 860

ATT GAA AAA CAC CAG AGT GAT GCA GGT TTA TAT GTA ATT GTG CCA GTA        2640
Ile Glu Lys His Gln Ser Asp Ala Gly Leu Tyr Val Ile Val Pro Val
865                 870                 875                 880

ATT ATT TCC TCT TCC ATC TTA TTG CTT GGA ACA TTA TTA ATA TCA CAC        2688
Ile Ile Ser Ser Ser Ile Leu Leu Leu Gly Thr Leu Leu Ile Ser His
                885                 890                 895

CAA AGA ATG AAA AAG CTA TTT TGG GAA GAT GTT CCG AAC CCC AAG AAT        2736
Gln Arg Met Lys Lys Leu Phe Trp Glu Asp Val Pro Asn Pro Lys Asn
            900                 905                 910

TGT TCC TGG GCA CAA GGA CTT AAT TTT CAG AAG ATG CTT GAA GGC AGC        2784
Cys Ser Trp Ala Gln Gly Leu Asn Phe Gln Lys Met Leu Glu Gly Ser
        915                 920                 925

ATG TTC GTT AAG AGT CAT CAC CAC TCC CTA ATC TCA AGT ACC CAG GGA        2832
Met Phe Val Lys Ser His His His Ser Leu Ile Ser Ser Thr Gln Gly
    930                 935                 940

CAC AAA CAC TGC GGA AGG CCA CAG GGT CCT CTG CAT AGG AAA ACC AGA        2880
His Lys His Cys Gly Arg Pro Gln Gly Pro Leu His Arg Lys Thr Arg
945                 950                 955                 960

GAC CTT TGT TCA CTT GTT TAT CTG CTG ACC CTC CCT CCA CTA TTG TCC        2928
Asp Leu Cys Ser Leu Val Tyr Leu Leu Thr Leu Pro Pro Leu Leu Ser
                965                 970                 975

TAT GAC CCT GCC AAA TCC CCC TCT GTG AGA AAC ACC CAA GAA TGA TCA        2976
Tyr Asp Pro Ala Lys Ser Pro Ser Val Arg Asn Thr Gln Glu  *  Ser
            980                 985                 990

ATA AAA AAA AAA AAA                                                    2991
Ile Lys Lys Lys Lys
        995

(2) INFORMATION FOR SEQ ID NO: 2:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 2:

Ala Arg Ala Thr Gln Val Pro Glu Pro Arg Pro Ala Pro Ile Ser Ala
1               5                   10                  15

Phe Gly Arg Val Gly Pro Pro Asp Gln Gly Val Leu Leu
            20                  25

(2) INFORMATION FOR SEQ ID NO: 3:

(i) SEQUENCE CHARACTERISTICS:
        (A) LENGTH: 960 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 3:

Ser Lys Met Ile Cys Gln Lys Phe Cys Val Val Leu Leu His Trp Glu
1               5                   10                  15

Phe Ile Tyr Val Ile Thr Ala Phe Asn Leu Ser Tyr Pro Ile Thr Pro
            20                  25                  30

Trp Arg Phe Lys Leu Ser Cys Met Pro Pro Asn Ser Thr Tyr Asp Tyr
        35                  40                  45
```

```
Phe Leu Leu Pro Ala Gly Leu Ser Lys Asn Thr Ser Asn Ser Asn Gly
 50                  55                  60

His Tyr Glu Thr Ala Val Glu Pro Lys Phe Asn Ser Ser Gly Thr His
 65                  70                  75                  80

Phe Ser Asn Leu Ser Lys Ala Thr Phe His Cys Cys Phe Arg Ser Glu
                 85                  90                  95

Gln Asp Arg Asn Cys Ser Leu Cys Ala Asp Asn Ile Glu Gly Arg Thr
            100                 105                 110

Phe Val Ser Thr Val Asn Ser Leu Val Phe Gln Gln Ile Asp Ala Asn
        115                 120                 125

Trp Asn Ile Gln Cys Trp Leu Lys Gly Asp Leu Lys Leu Phe Ile Cys
    130                 135                 140

Tyr Val Glu Ser Leu Phe Lys Asn Leu Phe Arg Asn Tyr Asn Tyr Lys
145                 150                 155                 160

Val His Leu Leu Tyr Val Leu Pro Glu Val Leu Glu Asp Ser Pro Leu
                165                 170                 175

Val Pro Gln Lys Gly Ser Phe Gln Met Val His Cys Asn Cys Ser Val
            180                 185                 190

His Glu Cys Cys Glu Cys Leu Val Pro Val Pro Thr Ala Lys Leu Asn
        195                 200                 205

Asp Thr Leu Leu Met Cys Leu Lys Ile Thr Ser Gly Gly Val Ile Phe
    210                 215                 220

Arg Ser Pro Leu Met Ser Val Gln Pro Ile Asn Met Val Lys Pro Asp
225                 230                 235                 240

Pro Pro Leu Gly Leu His Met Glu Ile Thr Asp Asp Gly Asn Leu Lys
                245                 250                 255

Ile Ser Trp Ser Ser Pro Pro Leu Val Pro Phe Pro Leu Gln Tyr Gln
            260                 265                 270

Val Lys Tyr Ser Glu Asn Ser Thr Thr Val Ile Arg Glu Ala Asp Lys
        275                 280                 285

Ile Val Ser Ala Thr Ser Leu Leu Val Asp Ser Ile Leu Pro Gly Ser
    290                 295                 300

Ser Tyr Glu Val Gln Val Arg Gly Lys Arg Leu Asp Gly Pro Gly Ile
305                 310                 315                 320

Trp Ser Asp Trp Ser Thr Pro Arg Val Phe Thr Thr Gln Asp Val Ile
                325                 330                 335

Tyr Phe Pro Pro Lys Ile Leu Thr Ser Val Gly Ser Asn Val Ser Phe
            340                 345                 350

His Cys Ile Tyr Lys Lys Glu Asn Lys Ile Val Pro Ser Lys Glu Ile
        355                 360                 365

Val Trp Trp Met Asn Leu Ala Glu Lys Ile Pro Gln Ser Gln Tyr Asp
    370                 375                 380

Val Val Ser Asp His Val Ser Lys Val Thr Phe Phe Asn Leu Asn Glu
385                 390                 395                 400

Thr Lys Pro Arg Gly Lys Phe Thr Tyr Asp Ala Val Tyr Cys Cys Asn
                405                 410                 415

Glu His Glu Cys His His Arg Tyr Ala Glu Leu Tyr Val Ile Asp Val
            420                 425                 430

Asn Ile Asn Ile Ser Cys Glu Thr Asp Gly Tyr Leu Thr Lys Met Thr
        435                 440                 445

Cys Arg Trp Ser Thr Ser Thr Ile Gln Ser Leu Ala Glu Ser Thr Leu
450                 455                 460
```

```
Gln Leu Arg Tyr His Arg Ser Ser Leu Tyr Cys Ser Asp Ile Pro Ser
465                 470                 475                 480

Ile His Pro Ile Ser Glu Pro Lys Asp Cys Tyr Leu Gln Ser Asp Gly
            485                 490                 495

Phe Tyr Glu Cys Ile Phe Gln Pro Ile Phe Leu Leu Ser Gly Tyr Thr
        500                 505                 510

Met Trp Ile Arg Ile Asn His Ser Leu Gly Ser Leu Asp Ser Pro Pro
    515                 520                 525

Thr Cys Val Leu Pro Asp Ser Val Val Lys Pro Leu Pro Pro Ser Ser
530                 535                 540

Val Lys Ala Glu Ile Thr Ile Asn Ile Gly Leu Leu Lys Ile Ser Trp
545                 550                 555                 560

Glu Lys Pro Val Phe Pro Glu Asn Asn Leu Gln Phe Gln Ile Arg Tyr
            565                 570                 575

Gly Leu Ser Gly Lys Glu Val Gln Trp Lys Met Tyr Glu Val Tyr Asp
        580                 585                 590

Ala Lys Ser Lys Ser Val Ser Leu Pro Val Pro Asp Leu Cys Ala Val
    595                 600                 605

Tyr Ala Tyr Gln Val Arg Cys Lys Arg Leu Asp Gly Leu Gly Tyr Trp
610                 615                 620

Ser Asn Trp Ser Asn Pro Ala Tyr Thr Val Val Met Asp Ile Lys Val
625                 630                 635                 640

Pro Met Arg Gly Pro Glu Phe Trp Arg Ile Ile Asn Gly Asp Thr Met
            645                 650                 655

Lys Lys Glu Lys Asn Val Thr Leu Leu Trp Lys Pro Leu Met Lys Asn
        660                 665                 670

Asp Ser Leu Cys Ser Val Gln Arg Tyr Val Ile Asn His His Thr Ser
    675                 680                 685

Cys Asn Gly Thr Trp Ser Glu Asp Val Gly Asn His Thr Lys Phe Thr
690                 695                 700

Phe Leu Trp Thr Glu Gln Ala His Thr Val Thr Val Leu Ala Ile Asn
705                 710                 715                 720

Ser Ile Gly Ala Ser Val Ala Asn Phe Asn Leu Thr Phe Ser Trp Pro
            725                 730                 735

Met Ser Lys Val Asn Ile Val Gln Ser Leu Ser Ala Tyr Pro Leu Asn
        740                 745                 750

Ser Ser Cys Val Ile Val Ser Trp Ile Leu Ser Pro Ser Asp Tyr Lys
    755                 760                 765

Leu Met Tyr Phe Ile Ile Glu Trp Lys Asn Leu Asn Glu Asp Gly Glu
770                 775                 780

Ile Lys Trp Leu Arg Ile Ser Ser Ser Val Lys Lys Tyr Tyr Ile His
785                 790                 795                 800

Asp His Phe Ile Pro Ile Glu Lys Tyr Gln Phe Ser Leu Tyr Pro Ile
            805                 810                 815

Phe Met Glu Gly Val Gly Lys Pro Lys Ile Ile Asn Ser Phe Thr Gln
        820                 825                 830

Asp Asp Ile Glu Lys His Gln Ser Asp Ala Gly Leu Tyr Val Ile Val
    835                 840                 845

Pro Val Ile Ile Ser Ser Ile Leu Leu Leu Gly Thr Leu Leu Ile
850                 855                 860

Ser His Gln Arg Met Lys Lys Leu Phe Trp Glu Asp Val Pro Asn Pro
865                 870                 875                 880

Lys Asn Cys Ser Trp Ala Gln Gly Leu Asn Phe Gln Lys Met Leu Glu
```

```
                    885              890                895
Gly Ser Met Phe Val Lys Ser His His His Ser Leu Ile Ser Ser Thr
            900                  905                910
Gln Gly His Lys His Cys Gly Arg Pro Gln Gly Pro Leu His Arg Lys
            915                  920              925
Thr Arg Asp Leu Cys Ser Leu Val Tyr Leu Leu Thr Leu Pro Pro Leu
        930              935              940
Leu Ser Tyr Asp Pro Ala Lys Ser Pro Ser Val Arg Asn Thr Gln Glu
945              950              955                  960
```

(2) INFORMATION FOR SEQ ID NO: 4:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 4:

```
Ser Ile Lys Lys Lys Lys
 1               5
```

(2) INFORMATION FOR SEQ ID NO: 5:

(i) SEQUENCE CHARACTERISTICS:
        (A) LENGTH: 241 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 5:

```
AGGACTTAAT TTTCAGAAGA TGCTTGAAGG CAGCATGTTC GTTAAGAGTC ATCACCACTC      60
CCTAATCTCA AGTACCCAGG GACACAAACA CTGCGGAAGG CCACAGGGTC CTCTGCATAG     120
GAAAACCAGA GACCTTTGTT CACTTGTTTA TCTGCTGACC CTCCCTCCAC TATTGTCCTA     180
TGACCCTGCC AAATCCCCCT CTGTGAGAAA CACCCAAGAA TGATCAATAA AAAAAAAAAA     240
A                                                                    241
```

(2) INFORMATION FOR SEQ ID NO: 6:

(i) SEQUENCE CHARACTERISTICS:
        (A) LENGTH: 130 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 6:

```
AGGACTTAAT TTTCAGAAGA AAATGCCTGG CACAAAGGAA CTACTGGGTG GAGGTTGGTT      60
GACTTAGGAA ATGCTTGTGA AGCTACGTCC TACCTCGTGC GCACCTGCTC TCCCTGAGGT     120
GTGCACAATG                                                            130
```

(2) INFORMATION FOR SEQ ID NO: 7:

(i) SEQUENCE CHARACTERISTICS:
        (A) LENGTH: 127 base pairs
        (B) TYPE: nucleic acid
        (C) STRANDEDNESS: single -continued (D) TOPOLOGY: linear (ii) MOLECULE TYPE: DNA (xi) SEQUENCE DESCRIPTION: SEQ ID NO: 7:

AGGACTTAAT TTTCAGAAGA GAACGGACAT TCTTTGAAGT CTAATCATGA TCACTACAGA        60

TGAACCCAAT GTGCCAACTT CCCAACAGTC TATAGAGTAT TAGAAGATTT TTACATTCTG       120

AAGAAGG                                                                 127

(2) INFORMATION FOR SEQ ID NO: 8:

(i) SEQUENCE CHARACTERISTICS:
        (A) LENGTH: 958 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 8:

Met Ile Cys Gln Lys Phe Cys Val Val Leu Leu His Trp Glu Phe Ile
 1               5                  10                  15

Tyr Val Ile Thr Ala Phe Asn Leu Ser Tyr Pro Ile Thr Pro Trp Arg
                20                  25                  30

Phe Lys Leu Ser Cys Met Pro Pro Asn Ser Thr Tyr Asp Tyr Phe Leu
            35                  40                  45

Leu Pro Ala Gly Leu Ser Lys Asn Thr Ser Asn Ser Asn Gly His Tyr
50                  55                  60

Glu Thr Ala Val Glu Pro Lys Phe Asn Ser Ser Gly Thr His Phe Ser
65                  70                  75                  80

Asn Leu Ser Lys Ala Thr Phe His Cys Cys Phe Arg Ser Glu Gln Asp
                85                  90                  95

Arg Asn Cys Ser Leu Cys Ala Asp Asn Ile Glu Gly Arg Thr Phe Val
            100                 105                 110

Ser Thr Val Asn Ser Leu Val Phe Gln Gln Ile Asp Ala Asn Trp Asn
        115                 120                 125

Ile Gln Cys Trp Leu Lys Gly Asp Leu Lys Leu Phe Ile Cys Tyr Val
130                 135                 140

Glu Ser Leu Phe Lys Asn Leu Phe Arg Asn Tyr Asn Tyr Lys Val His
145                 150                 155                 160

Leu Leu Tyr Val Leu Pro Glu Val Leu Glu Asp Ser Pro Leu Val Pro
                165                 170                 175

Gln Lys Gly Ser Phe Gln Met Val His Cys Asn Cys Ser Val His Glu
            180                 185                 190

Cys Cys Glu Cys Leu Val Pro Val Pro Thr Ala Lys Leu Asn Asp Thr
        195                 200                 205

Leu Leu Met Cys Leu Lys Ile Thr Ser Gly Val Ile Phe Arg Ser
210                 215                 220

Pro Leu Met Ser Val Gln Pro Ile Asn Met Val Lys Pro Asp Pro Pro
225                 230                 235                 240

Leu Gly Leu His Met Glu Ile Thr Asp Asp Gly Asn Leu Lys Ile Ser
                245                 250                 255

Trp Ser Ser Pro Pro Leu Val Pro Phe Pro Leu Gln Tyr Gln Val Lys
            260                 265                 270

Tyr Ser Glu Asn Ser Thr Thr Val Ile Arg Glu Ala Asp Lys Ile Val
        275                 280                 285

-continued

```
Ser Ala Thr Ser Leu Leu Val Asp Ser Ile Leu Pro Gly Ser Ser Tyr
    290                 295                 300
Glu Val Gln Val Arg Gly Lys Arg Leu Asp Gly Pro Gly Ile Trp Ser
305                 310                 315                 320
Asp Trp Ser Thr Pro Arg Val Phe Thr Thr Gln Asp Val Ile Tyr Phe
                325                 330                 335
Pro Pro Lys Ile Leu Thr Ser Val Gly Ser Asn Val Ser Phe His Cys
                340                 345                 350
Ile Tyr Lys Lys Glu Asn Lys Ile Val Pro Ser Lys Glu Ile Val Trp
                355                 360                 365
Trp Met Asn Leu Ala Glu Lys Ile Pro Gln Ser Gln Tyr Asp Val Val
    370                 375                 380
Ser Asp His Val Ser Lys Val Thr Phe Phe Asn Leu Asn Glu Thr Lys
385                 390                 395                 400
Pro Arg Gly Lys Phe Thr Tyr Asp Ala Val Tyr Cys Cys Asn Glu His
                405                 410                 415
Glu Cys His His Arg Tyr Ala Glu Leu Tyr Val Ile Asp Val Asn Ile
                420                 425                 430
Asn Ile Ser Cys Glu Thr Asp Gly Tyr Leu Thr Lys Met Thr Cys Arg
                435                 440                 445
Trp Ser Thr Ser Thr Ile Gln Ser Leu Ala Glu Ser Thr Leu Gln Leu
    450                 455                 460
Arg Tyr His Arg Ser Ser Leu Tyr Cys Ser Asp Ile Pro Ser Ile His
465                 470                 475                 480
Pro Ile Ser Glu Pro Lys Asp Cys Tyr Leu Gln Ser Asp Gly Phe Tyr
                485                 490                 495
Glu Cys Ile Phe Gln Pro Ile Phe Leu Leu Ser Gly Tyr Thr Met Trp
                500                 505                 510
Ile Arg Ile Asn His Ser Leu Gly Ser Leu Asp Ser Pro Pro Thr Cys
                515                 520                 525
Val Leu Pro Asp Ser Val Val Lys Pro Leu Pro Pro Ser Ser Val Lys
    530                 535                 540
Ala Glu Ile Thr Ile Asn Ile Gly Leu Leu Lys Ile Ser Trp Glu Lys
545                 550                 555                 560
Pro Val Phe Pro Glu Asn Asn Leu Gln Phe Gln Ile Arg Tyr Gly Leu
                565                 570                 575
Ser Gly Lys Glu Val Gln Trp Lys Met Tyr Glu Val Tyr Asp Ala Lys
                580                 585                 590
Ser Lys Ser Val Ser Leu Pro Val Pro Asp Leu Cys Ala Val Tyr Ala
                595                 600                 605
Val Gln Val Arg Cys Lys Arg Leu Asp Gly Leu Gly Tyr Trp Ser Asn
    610                 615                 620
Trp Ser Asn Pro Ala Tyr Thr Val Val Met Asp Ile Lys Val Pro Met
625                 630                 635                 640
Arg Gly Pro Glu Phe Trp Arg Ile Ile Asn Gly Asp Thr Met Lys Lys
                645                 650                 655
Glu Lys Asn Val Thr Leu Leu Trp Lys Pro Leu Met Lys Asn Asp Ser
                660                 665                 670
Leu Cys Ser Val Gln Arg Tyr Val Ile Asn His His Thr Ser Cys Asn
                675                 680                 685
Gly Thr Trp Ser Glu Asp Val Gly Asn His Thr Lys Phe Thr Phe Leu
    690                 695                 700
Trp Thr Glu Gln Ala His Thr Val Thr Val Leu Ala Ile Asn Ser Ile
```

-continued

```
            705                 710                 715                 720
    Gly Ala Ser Val Ala Asn Phe Asn Leu Thr Phe Ser Trp Pro Met Ser
                    725                 730                 735
    Lys Val Asn Ile Val Gln Ser Leu Ser Ala Tyr Pro Leu Asn Ser Ser
                    740                 745                 750
    Cys Val Ile Val Ser Trp Ile Leu Ser Pro Ser Asp Tyr Lys Leu Met
                    755                 760                 765
    Tyr Phe Ile Ile Glu Trp Lys Asn Leu Asn Glu Asp Gly Glu Ile Lys
                    770                 775                 780
    Trp Leu Arg Ile Ser Ser Val Lys Lys Tyr Tyr Ile His Asp His
    785                 790                 795                 800
    Phe Ile Pro Ile Glu Lys Tyr Gln Phe Ser Leu Tyr Pro Ile Phe Met
                    805                 810                 815
    Glu Gly Val Gly Lys Pro Lys Ile Ile Asn Ser Phe Thr Gln Asp Asp
                    820                 825                 830
    Ile Glu Lys His Gln Ser Asp Ala Gly Leu Tyr Val Ile Val Pro Val
                    835                 840                 845
    Ile Ile Ser Ser Ser Ile Leu Leu Leu Gly Thr Leu Leu Ile Ser His
                    850                 855                 860
    Gln Arg Met Lys Lys Leu Phe Trp Glu Asp Val Pro Asn Pro Lys Asn
    865                 870                 875                 880
    Cys Ser Trp Ala Gln Gly Leu Asn Phe Gln Lys Met Leu Glu Gly Ser
                    885                 890                 895
    Met Phe Val Lys Ser His His Ser Leu Ile Ser Ser Thr Gln Gly
                    900                 905                 910
    His Lys His Cys Gly Arg Pro Gln Gly Pro Leu His Arg Lys Thr Arg
                    915                 920                 925
    Asp Leu Cys Ser Leu Val Tyr Leu Leu Thr Leu Pro Pro Leu Leu Ser
                    930                 935                 940
    Tyr Asp Pro Ala Lys Ser Pro Ser Val Arg Asn Thr Gln Glu
    945                 950                 955
```

(2) INFORMATION FOR SEQ ID NO: 9:

(i) SEQUENCE CHARACTERISTICS:
        (A) LENGTH: 906 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 9:

```
Met Ile Cys Gln Lys Phe Cys Val Val Leu Leu His Trp Glu Phe Ile
1                   5                   10                  15
Tyr Val Ile Thr Ala Phe Asn Leu Ser Tyr Pro Ile Thr Pro Trp Arg
                20                  25                  30
Phe Lys Leu Ser Cys Met Pro Pro Asn Ser Thr Tyr Asp Tyr Phe Leu
            35                  40                  45
Leu Pro Ala Gly Leu Ser Lys Asn Thr Ser Asn Ser Asn Gly His Tyr
        50                  55                  60
Glu Thr Ala Val Glu Pro Lys Phe Asn Ser Ser Gly Thr His Phe Ser
65                  70                  75                  80
Asn Leu Ser Lys Ala Thr Phe His Cys Cys Phe Arg Ser Glu Gln Asp
                85                  90                  95
Arg Asn Cys Ser Leu Cys Ala Asp Asn Ile Glu Gly Arg Thr Phe Val
```

-continued

```
              100                 105                 110
Ser Thr Val Asn Ser Leu Val Phe Gln Gln Ile Asp Ala Asn Trp Asn
            115                 120                 125

Ile Gln Cys Trp Leu Lys Gly Asp Leu Lys Leu Phe Ile Cys Tyr Val
            130                 135                 140

Glu Ser Leu Phe Lys Asn Leu Phe Arg Asn Tyr Asn Tyr Lys Val His
145                 150                 155                 160

Leu Leu Tyr Val Leu Pro Glu Val Leu Glu Asp Ser Pro Leu Val Pro
                165                 170                 175

Gln Lys Gly Ser Phe Gln Met Val His Cys Asn Cys Ser Val His Glu
            180                 185                 190

Cys Cys Glu Cys Leu Val Pro Val Pro Thr Ala Lys Leu Asn Asp Thr
            195                 200                 205

Leu Leu Met Cys Leu Lys Ile Thr Ser Gly Gly Val Ile Phe Arg Ser
    210                 215                 220

Pro Leu Met Ser Val Gln Pro Ile Asn Met Val Lys Pro Asp Pro Pro
225                 230                 235                 240

Leu Gly Leu His Met Glu Ile Thr Asp Asp Gly Asn Leu Lys Ile Ser
                245                 250                 255

Trp Ser Ser Pro Pro Leu Val Pro Phe Pro Leu Gln Tyr Gln Val Lys
            260                 265                 270

Tyr Ser Glu Asn Ser Thr Thr Val Ile Arg Glu Ala Asp Lys Ile Val
            275                 280                 285

Ser Ala Thr Ser Leu Leu Val Asp Ser Ile Leu Pro Gly Ser Ser Tyr
    290                 295                 300

Glu Val Gln Val Arg Gly Lys Arg Leu Asp Gly Pro Gly Ile Trp Ser
305                 310                 315                 320

Asp Trp Ser Thr Pro Arg Val Phe Thr Thr Gln Asp Val Ile Tyr Phe
                325                 330                 335

Pro Pro Lys Ile Leu Thr Ser Val Gly Ser Asn Val Ser Phe His Cys
            340                 345                 350

Ile Tyr Lys Lys Glu Asn Lys Ile Val Pro Ser Lys Glu Ile Val Trp
            355                 360                 365

Trp Met Asn Leu Ala Glu Lys Ile Pro Gln Ser Gln Tyr Asp Val Val
    370                 375                 380

Ser Asp His Val Ser Lys Val Thr Phe Phe Asn Leu Asn Glu Thr Lys
385                 390                 395                 400

Pro Arg Gly Lys Phe Thr Tyr Asp Ala Val Tyr Cys Cys Asn Glu His
                405                 410                 415

Glu Cys His His Arg Tyr Ala Glu Leu Tyr Val Ile Asp Val Asn Ile
            420                 425                 430

Asn Ile Ser Cys Glu Thr Asp Gly Tyr Leu Thr Lys Met Thr Cys Arg
    435                 440                 445

Trp Ser Thr Ser Thr Ile Gln Ser Leu Ala Glu Ser Thr Leu Gln Leu
    450                 455                 460

Arg Tyr His Arg Ser Ser Leu Tyr Cys Ser Asp Ile Pro Ser Ile His
465                 470                 475                 480

Pro Ile Ser Glu Pro Lys Asp Cys Tyr Leu Gln Ser Asp Gly Phe Tyr
                485                 490                 495

Glu Cys Ile Phe Gln Pro Ile Phe Leu Leu Ser Gly Tyr Thr Met Trp
            500                 505                 510

Ile Arg Ile Asn His Ser Leu Gly Ser Leu Asp Ser Pro Pro Thr Cys
            515                 520                 525
```

```
Val Leu Pro Asp Ser Val Val Lys Pro Leu Pro Ser Ser Val Lys
    530                 535                 540

Ala Glu Ile Thr Ile Asn Ile Gly Leu Leu Lys Ile Ser Trp Glu Lys
545                 550                 555                 560

Pro Val Phe Pro Glu Asn Asn Leu Gln Phe Gln Ile Arg Tyr Gly Leu
                565                 570                 575

Ser Gly Lys Glu Val Gln Trp Lys Met Tyr Glu Val Tyr Asp Ala Lys
            580                 585                 590

Ser Lys Ser Val Ser Leu Pro Val Pro Asp Leu Cys Ala Val Tyr Ala
    595                 600                 605

Val Gln Val Arg Cys Lys Arg Leu Asp Gly Leu Gly Tyr Trp Ser Asn
610                 615                 620

Trp Ser Asn Pro Ala Tyr Thr Val Val Met Asp Ile Lys Val Pro Met
625                 630                 635                 640

Arg Gly Pro Glu Phe Trp Arg Ile Ile Asn Gly Asp Thr Met Lys Lys
                645                 650                 655

Glu Lys Asn Val Thr Leu Leu Trp Lys Pro Leu Met Lys Asn Asp Ser
            660                 665                 670

Leu Cys Ser Val Gln Arg Tyr Val Ile Asn His His Thr Ser Cys Asn
    675                 680                 685

Gly Thr Trp Ser Glu Asp Val Gly Asn His Thr Lys Phe Thr Phe Leu
690                 695                 700

Trp Thr Glu Gln Ala His Thr Val Thr Val Leu Ala Ile Asn Ser Ile
705                 710                 715                 720

Gly Ala Ser Val Ala Asn Phe Asn Leu Thr Phe Ser Trp Pro Met Ser
                725                 730                 735

Lys Val Asn Ile Val Gln Ser Leu Ser Ala Tyr Pro Leu Asn Ser Ser
            740                 745                 750

Cys Val Ile Val Ser Trp Ile Leu Ser Pro Ser Asp Tyr Lys Leu Met
    755                 760                 765

Tyr Phe Ile Ile Glu Trp Lys Asn Leu Asn Glu Asp Gly Glu Ile Lys
770                 775                 780

Trp Leu Arg Ile Ser Ser Ser Val Lys Lys Tyr Tyr Ile His Asp His
785                 790                 795                 800

Phe Ile Pro Ile Glu Lys Tyr Gln Phe Ser Leu Tyr Pro Ile Phe Met
                805                 810                 815

Glu Gly Val Gly Lys Pro Lys Ile Ile Asn Ser Phe Thr Gln Asp Asp
            820                 825                 830

Ile Glu Lys His Gln Ser Asp Ala Gly Leu Tyr Val Ile Val Pro Val
    835                 840                 845

Ile Ile Ser Ser Ser Ile Leu Leu Leu Gly Thr Leu Leu Ile Ser His
850                 855                 860

Gln Arg Met Lys Lys Leu Phe Trp Glu Asp Val Pro Asn Pro Lys Asn
865                 870                 875                 880

Cys Ser Trp Ala Gln Gly Leu Asn Phe Gln Lys Met Pro Gly Tyr
                885                 890                 895

Lys Glu Leu Leu Gly Gly Gly Trp Leu Thr
            900                 905

(2) INFORMATION FOR SEQ ID NO: 10:

(i) SEQUENCE CHARACTERISTICS:
        (A) LENGTH: 896 amino acids
        (B) TYPE: amino acid
```

-continued (C) STRANDEDNESS: single
(D) TOPOLOGY: linear (ii) MOLECULE TYPE: protein (xi) SEQUENCE DESCRIPTION: SEQ ID NO: 10:

```
Met Ile Cys Gln Lys Phe Cys Val Val Leu His Trp Glu Phe Ile
 1               5                  10                  15

Tyr Val Ile Thr Ala Phe Asn Leu Ser Tyr Pro Ile Thr Pro Trp Arg
                 20                  25                  30

Phe Lys Leu Ser Cys Met Pro Pro Asn Ser Thr Tyr Asp Tyr Phe Leu
                 35                  40                  45

Leu Pro Ala Gly Leu Ser Lys Asn Thr Ser Asn Ser Asn Gly His Tyr
 50                  55                  60

Glu Thr Ala Val Glu Pro Lys Phe Asn Ser Ser Gly Thr His Phe Ser
 65                  70                  75                  80

Asn Leu Ser Lys Ala Thr Phe His Cys Cys Phe Arg Ser Glu Gln Asp
                 85                  90                  95

Arg Asn Cys Ser Leu Cys Ala Asp Asn Ile Glu Gly Arg Thr Phe Val
                100                 105                 110

Ser Thr Val Asn Ser Leu Val Phe Gln Gln Ile Asp Ala Asn Trp Asn
                115                 120                 125

Ile Gln Cys Trp Leu Lys Gly Asp Leu Lys Leu Phe Ile Cys Tyr Val
130                 135                 140

Glu Ser Leu Phe Lys Asn Leu Phe Arg Asn Tyr Asn Tyr Lys Val His
145                 150                 155                 160

Leu Leu Tyr Val Leu Pro Glu Val Leu Glu Asp Ser Pro Leu Val Pro
                165                 170                 175

Gln Lys Gly Ser Phe Gln Met Val His Cys Asn Cys Ser Val His Glu
                180                 185                 190

Cys Cys Glu Cys Leu Val Pro Val Pro Thr Ala Lys Leu Asn Asp Thr
                195                 200                 205

Leu Leu Met Cys Leu Lys Ile Thr Ser Gly Gly Val Ile Phe Arg Ser
210                 215                 220

Pro Leu Met Ser Val Gln Pro Ile Asn Met Val Lys Pro Asp Pro Pro
225                 230                 235                 240

Leu Gly Leu His Met Glu Ile Thr Asp Asp Gly Asn Leu Lys Ile Ser
                245                 250                 255

Trp Ser Ser Pro Pro Leu Val Pro Phe Pro Leu Gln Tyr Gln Val Lys
                260                 265                 270

Tyr Ser Glu Asn Ser Thr Thr Val Ile Arg Glu Ala Asp Lys Ile Val
                275                 280                 285

Ser Ala Thr Ser Leu Leu Val Asp Ser Ile Leu Pro Gly Ser Ser Tyr
290                 295                 300

Glu Val Gln Val Arg Gly Lys Arg Leu Asp Gly Pro Gly Ile Trp Ser
305                 310                 315                 320

Asp Trp Ser Thr Pro Arg Val Phe Thr Thr Gln Asp Val Ile Tyr Phe
                325                 330                 335

Pro Pro Lys Ile Leu Thr Ser Val Gly Ser Asn Val Ser Phe His Cys
                340                 345                 350

Ile Tyr Lys Lys Glu Asn Lys Ile Val Pro Ser Lys Glu Ile Val Trp
                355                 360                 365

Trp Met Asn Leu Ala Glu Lys Ile Pro Gln Ser Gln Tyr Asp Val Val
370                 375                 380
```

```
Ser Asp His Val Ser Lys Val Thr Phe Phe Asn Leu Asn Glu Thr Lys
385                 390                 395                 400

Pro Arg Gly Lys Phe Thr Tyr Asp Ala Val Tyr Cys Cys Asn Glu His
            405                 410                 415

Glu Cys His His Arg Tyr Ala Glu Leu Tyr Val Ile Asp Val Asn Ile
            420                 425                 430

Asn Ile Ser Cys Glu Thr Asp Gly Tyr Leu Thr Lys Met Thr Cys Arg
            435                 440                 445

Trp Ser Thr Ser Thr Ile Gln Ser Leu Ala Glu Ser Thr Leu Gln Leu
450                 455                 460

Arg Tyr His Arg Ser Ser Leu Tyr Cys Ser Asp Ile Pro Ser Ile His
465                 470                 475                 480

Pro Ile Ser Glu Pro Lys Asp Cys Tyr Leu Gln Ser Asp Gly Phe Tyr
            485                 490                 495

Glu Cys Ile Phe Gln Pro Ile Phe Leu Leu Ser Gly Tyr Thr Met Trp
            500                 505                 510

Ile Arg Ile Asn His Ser Leu Gly Ser Leu Asp Ser Pro Pro Thr Cys
            515                 520                 525

Val Leu Pro Asp Ser Val Val Lys Pro Leu Pro Pro Ser Ser Val Lys
530                 535                 540

Ala Glu Ile Thr Ile Asn Ile Gly Leu Leu Lys Ile Ser Trp Glu Lys
545                 550                 555                 560

Pro Val Phe Pro Glu Asn Asn Leu Gln Phe Gln Ile Arg Tyr Gly Leu
            565                 570                 575

Ser Gly Lys Glu Val Gln Trp Lys Met Tyr Glu Val Tyr Asp Ala Lys
            580                 585                 590

Ser Lys Ser Val Ser Leu Pro Val Pro Asp Leu Cys Ala Val Tyr Ala
            595                 600                 605

Val Gln Val Arg Cys Lys Arg Leu Asp Gly Leu Gly Tyr Trp Ser Asn
610                 615                 620

Trp Ser Asn Pro Ala Tyr Thr Val Val Met Asp Ile Lys Val Pro Met
625                 630                 635                 640

Arg Gly Pro Glu Phe Trp Arg Ile Ile Asn Gly Asp Thr Met Lys Lys
            645                 650                 655

Glu Lys Asn Val Thr Leu Leu Trp Lys Pro Leu Met Lys Asn Asp Ser
            660                 665                 670

Leu Cys Ser Val Gln Arg Tyr Val Ile Asn His His Thr Ser Cys Asn
            675                 680                 685

Gly Thr Trp Ser Glu Asp Val Gly Asn His Thr Lys Phe Thr Phe Leu
690                 695                 700

Trp Thr Glu Gln Ala His Thr Val Thr Val Leu Ala Ile Asn Ser Ile
705                 710                 715                 720

Gly Ala Ser Val Ala Asn Phe Asn Leu Thr Phe Ser Trp Pro Met Ser
            725                 730                 735

Lys Val Asn Ile Val Gln Ser Leu Ser Ala Tyr Pro Leu Asn Ser Ser
            740                 745                 750

Cys Val Ile Val Ser Trp Ile Leu Ser Pro Ser Asp Tyr Lys Leu Met
            755                 760                 765

Tyr Phe Ile Ile Glu Trp Lys Asn Leu Asn Glu Asp Gly Glu Ile Lys
770                 775                 780

Trp Leu Arg Ile Ser Ser Ser Val Lys Lys Tyr Tyr Ile His Asp His
785                 790                 795                 800

Phe Ile Pro Ile Glu Lys Tyr Gln Phe Ser Leu Tyr Pro Ile Phe Met
```

```
                  805                 810                 815
Glu Gly Val Gly Lys Pro Lys Ile Ile Asn Ser Phe Thr Gln Asp Asp
            820                 825                 830
Ile Glu Lys His Gln Ser Asp Ala Gly Leu Tyr Val Ile Val Pro Val
            835                 840                 845
Ile Ile Ser Ser Ser Ile Leu Leu Leu Gly Thr Leu Leu Ile Ser His
            850                 855                 860
Gln Arg Met Lys Lys Leu Phe Trp Glu Asp Val Pro Asn Pro Lys Asn
865                 870                 875                 880
Cys Ser Trp Ala Gln Gly Leu Asn Phe Gln Lys Arg Thr Asp Ile Leu
            885                 890                 895

(2) INFORMATION FOR SEQ ID NO: 11:

(i) SEQUENCE CHARACTERISTICS:
        (A) LENGTH: 1165 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 11:

Met Ile Cys Gln Lys Phe Cys Val Val Leu Leu His Trp Glu Phe Ile
1               5                  10                  15
Tyr Val Ile Thr Ala Phe Asn Leu Ser Tyr Pro Ile Thr Pro Trp Arg
            20                  25                  30
Phe Lys Leu Ser Cys Met Pro Pro Asn Ser Thr Tyr Asp Tyr Phe Leu
            35                  40                  45
Leu Pro Ala Gly Leu Ser Lys Asn Thr Ser Asn Ser Asn Gly His Tyr
50                  55                  60
Glu Thr Ala Val Glu Pro Lys Phe Asn Ser Ser Gly Thr His Phe Ser
65                  70                  75                  80
Asn Leu Ser Lys Thr Thr Phe His Cys Cys Phe Arg Ser Glu Gln Asp
            85                  90                  95
Arg Asn Cys Ser Leu Cys Ala Asp Asn Ile Glu Gly Lys Thr Phe Val
            100                 105                 110
Ser Thr Val Asn Ser Leu Val Phe Gln Gln Ile Asp Ala Asn Trp Asn
            115                 120                 125
Ile Gln Cys Trp Leu Lys Gly Asp Leu Lys Leu Phe Ile Cys Tyr Val
130                 135                 140
Glu Ser Leu Phe Lys Asn Leu Phe Arg Asn Tyr Asn Tyr Lys Val His
145                 150                 155                 160
Leu Leu Tyr Val Leu Pro Glu Val Leu Glu Asp Ser Pro Leu Val Pro
                165                 170                 175
Gln Lys Gly Ser Phe Gln Met Val His Cys Asn Cys Ser Val His Glu
            180                 185                 190
Cys Cys Glu Cys Leu Val Pro Val Pro Thr Ala Lys Leu Asn Asp Thr
            195                 200                 205
Leu Leu Met Cys Leu Lys Ile Thr Ser Gly Gly Val Ile Phe Gln Ser
            210                 215                 220
Pro Leu Met Ser Val Gln Pro Ile Asn Met Val Lys Pro Asp Pro Pro
225                 230                 235                 240
Leu Gly Leu His Met Glu Ile Thr Asp Asp Gly Asn Leu Lys Ile Ser
                245                 250                 255
Trp Ser Ser Pro Pro Leu Val Pro Phe Pro Leu Gln Tyr Gln Val Lys
```

-continued

```
                    260                 265                 270
Tyr Ser Glu Asn Ser Thr Thr Val Ile Arg Glu Ala Asp Lys Ile Val
        275                 280                 285
Ser Ala Thr Ser Leu Leu Val Asp Ser Ile Leu Pro Gly Ser Ser Tyr
        290                 295                 300
Glu Val Gln Val Arg Gly Lys Arg Leu Asp Gly Pro Gly Ile Trp Ser
305                 310                 315                 320
Asp Trp Ser Thr Pro Arg Val Phe Thr Thr Gln Asp Val Ile Tyr Phe
                325                 330                 335
Pro Pro Lys Ile Leu Thr Ser Val Gly Ser Asn Val Ser Phe His Cys
                340                 345                 350
Ile Tyr Lys Lys Glu Asn Lys Ile Val Pro Ser Lys Glu Ile Val Trp
                355                 360                 365
Trp Met Asn Leu Ala Glu Lys Ile Pro Gln Ser Gln Tyr Asp Val Val
                370                 375                 380
Ser Asp His Val Ser Lys Val Thr Phe Phe Asn Leu Asn Glu Thr Lys
385                 390                 395                 400
Pro Arg Gly Lys Phe Thr Tyr Asp Ala Val Tyr Cys Cys Asn Glu His
                405                 410                 415
Glu Cys His His Arg Tyr Ala Glu Leu Tyr Val Ile Asp Val Asn Ile
                420                 425                 430
Asn Ile Ser Cys Glu Thr Asp Gly Tyr Leu Thr Lys Met Thr Cys Arg
                435                 440                 445
Trp Ser Thr Ser Thr Ile Gln Ser Leu Ala Glu Ser Thr Leu Gln Leu
        450                 455                 460
Arg Tyr His Arg Ser Ser Leu Tyr Cys Ser Asp Ile Pro Ser Ile His
465                 470                 475                 480
Pro Ile Ser Glu Pro Lys Asp Cys Tyr Leu Gln Ser Asp Gly Phe Tyr
                485                 490                 495
Glu Cys Ile Phe Gln Pro Ile Phe Leu Leu Ser Gly Tyr Thr Met Trp
                500                 505                 510
Ile Arg Ile Asn His Ser Leu Gly Ser Leu Asp Ser Pro Pro Thr Cys
                515                 520                 525
Val Leu Pro Asp Ser Val Val Lys Pro Leu Pro Pro Ser Ser Val Lys
        530                 535                 540
Ala Glu Ile Thr Ile Asn Ile Gly Leu Leu Lys Ile Ser Trp Glu Lys
545                 550                 555                 560
Pro Val Phe Pro Glu Asn Asn Leu Gln Phe Gln Ile Arg Tyr Gly Leu
                565                 570                 575
Ser Gly Lys Glu Val Gln Trp Lys Met Tyr Glu Val Tyr Asp Ala Lys
                580                 585                 590
Ser Lys Ser Val Ser Leu Pro Val Pro Asp Leu Cys Ala Val Tyr Ala
        595                 600                 605
Val Gln Val Arg Cys Lys Arg Leu Asp Gly Leu Gly Tyr Trp Ser Asn
        610                 615                 620
Trp Ser Asn Pro Ala Tyr Thr Val Val Met Asp Ile Lys Val Pro Met
625                 630                 635                 640
Arg Gly Pro Glu Phe Trp Arg Ile Ile Asn Gly Asp Thr Met Lys Lys
                645                 650                 655
Glu Lys Asn Val Thr Leu Leu Trp Lys Pro Leu Met Lys Asn Asp Ser
                660                 665                 670
Leu Cys Ser Val Gln Arg Tyr Val Ile Asn His His Thr Ser Cys Asn
                675                 680                 685
```

```
Gly Thr Trp Ser Glu Asp Val Gly Asn His Thr Lys Phe Thr Phe Leu
    690                 695                 700

Trp Thr Glu Gln Ala His Thr Val Thr Val Leu Ala Ile Asn Ser Ile
705                 710                 715                 720

Gly Ala Ser Val Ala Asn Phe Asn Leu Thr Phe Ser Trp Pro Met Ser
                725                 730                 735

Lys Val Asn Ile Val Gln Ser Leu Ser Ala Tyr Pro Leu Asn Ser Ser
            740                 745                 750

Cys Val Ile Val Ser Trp Ile Leu Ser Pro Ser Asp Tyr Lys Leu Met
            755                 760                 765

Tyr Phe Ile Ile Glu Trp Lys Asn Leu Asn Glu Asp Gly Glu Ile Lys
770                 775                 780

Trp Leu Arg Ile Ser Ser Val Lys Lys Tyr Tyr Ile His Asp His
785                 790                 795                 800

Phe Ile Pro Ile Glu Lys Tyr Gln Phe Ser Leu Tyr Pro Ile Phe Met
                805                 810                 815

Glu Gly Val Gly Lys Pro Lys Ile Ile Asn Ser Phe Thr Gln Asp Asp
                820                 825                 830

Ile Glu Lys His Gln Ser Asp Ala Gly Leu Tyr Val Ile Val Pro Val
            835                 840                 845

Ile Ile Ser Ser Ser Ile Leu Leu Leu Gly Thr Leu Leu Ile Ser His
            850                 855                 860

Gln Arg Met Lys Lys Leu Phe Trp Glu Asp Val Pro Asn Pro Lys Asn
865                 870                 875                 880

Cys Ser Trp Ala Gln Gly Leu Asn Phe Gln Lys Pro Glu Thr Phe Glu
                885                 890                 895

His Leu Phe Ile Lys His Thr Ala Ser Val Thr Cys Gly Pro Leu Leu
                900                 905                 910

Leu Glu Pro Glu Thr Ile Ser Glu Asp Ile Ser Val Asp Thr Ser Trp
            915                 920                 925

Lys Asn Lys Asp Glu Met Met Pro Thr Thr Val Val Ser Leu Leu Ser
930                 935                 940

Thr Thr Asp Leu Glu Lys Gly Ser Val Cys Ile Ser Asp Gln Phe Asn
945                 950                 955                 960

Ser Val Asn Phe Ser Glu Ala Glu Gly Thr Glu Val Thr Tyr Glu Ala
                965                 970                 975

Glu Ser Gln Arg Gln Pro Phe Val Lys Tyr Ala Thr Leu Ile Ser Asn
            980                 985                 990

Ser Lys Pro Ser Glu Thr Gly Glu Glu Gln Gly Leu Ile Asn Ser Ser
            995                 1000                1005

Val Thr Lys Cys Phe Ser Ser Lys Asn Ser Pro Leu Lys Asp Ser Phe
    1010                1015                1020

Ser Asn Ser Ser Trp Glu Ile Glu Ala Gln Ala Phe Phe Ile Leu Ser
1025                1030                1035                1040

Asp Gln His Pro Asn Ile Ile Ser Pro His Leu Thr Phe Ser Glu Gly
                1045                1050                1055

Leu Asp Glu Leu Leu Lys Leu Glu Gly Asn Phe Pro Glu Glu Asn Asn
            1060                1065                1070

Asp Lys Lys Ser Ile Tyr Tyr Leu Gly Val Thr Ser Ile Lys Lys Arg
            1075                1080                1085

Glu Ser Gly Val Leu Leu Thr Asp Lys Ser Arg Val Ser Cys Pro Phe
            1090                1095                1100
```

```
Pro Ala Pro Cys Leu Phe Thr Asp Ile Arg Val Leu Gln Asp Ser Cys
1105                1110                1115                1120

Ser His Phe Val Glu Asn Asn Ile Asn Leu Gly Thr Ser Ser Lys Lys
            1125                1130                1135

Thr Phe Ala Ser Tyr Met Pro Gln Phe Gln Thr Cys Ser Thr Gln Thr
            1140                1145                1150

His Lys Ile Met Glu Asn Lys Met Cys Asp Leu Thr Val
        1155                1160                1165

(2) INFORMATION FOR SEQ ID NO: 12:

(i) SEQUENCE CHARACTERISTICS:
        (A) LENGTH: 894 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 12:

Met Met Cys Gln Lys Phe Tyr Val Val Leu Leu His Trp Glu Phe Leu
1                   5                   10                  15

Tyr Val Ile Ala Ala Leu Asn Leu Ala Tyr Pro Ile Ser Pro Trp Lys
            20                  25                  30

Phe Lys Leu Phe Cys Gly Pro Pro Asn Thr Thr Asp Asp Ser Phe Leu
        35                  40                  45

Ser Pro Ala Gly Ala Pro Asn Asn Ala Ser Ala Leu Lys Gly Ala Ser
50                  55                  60

Glu Ala Ile Val Glu Ala Lys Phe Asn Ser Ser Gly Ile Tyr Val Pro
65                  70                  75                  80

Glu Leu Ser Lys Thr Val Phe His Cys Cys Phe Gly Asn Glu Gln Gly
                85                  90                  95

Gln Asn Cys Ser Ala Leu Thr Asp Asn Thr Glu Gly Lys Thr Leu Ala
            100                 105                 110

Ser Val Val Lys Ala Ser Val Phe Arg Gln Leu Gly Val Asn Trp Asp
            115                 120                 125

Ile Glu Cys Trp Met Lys Gly Asp Leu Thr Leu Phe Ile Cys His Met
130                 135                 140

Glu Pro Leu Pro Lys Asn Pro Phe Lys Asn Tyr Asp Ser Lys Val His
145                 150                 155                 160

Leu Leu Tyr Asp Leu Pro Glu Val Ile Asp Asp Ser Pro Leu Pro Pro
            165                 170                 175

Leu Lys Asp Ser Phe Gln Thr Val Gln Cys Asn Cys Ser Leu Arg Gly
            180                 185                 190

Cys Glu Cys His Val Pro Val Pro Arg Ala Lys Leu Asn Tyr Ala Leu
            195                 200                 205

Leu Met Tyr Leu Glu Ile Thr Ser Ala Gly Val Ser Phe Gln Ser Pro
        210                 215                 220

Leu Met Ser Leu Gln Pro Met Leu Val Val Lys Pro Asp Pro Pro Leu
225                 230                 235                 240

Gly Leu His Met Glu Val Thr Asp Asp Gly Asn Leu Lys Ile Ser Trp
            245                 250                 255

Asp Ser Gln Thr Met Ala Pro Phe Pro Leu Gln Tyr Gln Val Lys Tyr
            260                 265                 270

Leu Glu Asn Ser Thr Ile Val Arg Glu Ala Ala Glu Ile Val Ser Ala
        275                 280                 285
```

-continued

```
Thr Ser Leu Leu Val Asp Ser Val Leu Pro Gly Ser Ser Tyr Glu Val
    290                 295                 300

Gln Val Arg Ser Lys Arg Leu Asp Gly Ser Gly Val Trp Ser Asp Trp
305                 310                 315                 320

Ser Ser Pro Gln Val Phe Thr Thr Gln Asp Val Val Tyr Phe Pro Pro
                    325                 330                 335

Lys Ile Leu Thr Ser Val Gly Ser Asn Ala Ser Phe His Cys Ile Tyr
                340                 345                 350

Lys Asn Glu Asn Gln Ile Ile Ser Ser Lys Gln Ile Val Trp Trp Arg
            355                 360                 365

Asn Leu Ala Glu Lys Ile Pro Glu Ile Gln Tyr Ser Ile Val Ser Asp
    370                 375                 380

Arg Val Ser Lys Val Thr Phe Ser Asn Leu Lys Ala Thr Arg Pro Arg
385                 390                 395                 400

Gly Lys Phe Thr Tyr Asp Ala Val Tyr Cys Cys Asn Glu Gln Ala Cys
                    405                 410                 415

His His Arg Tyr Ala Glu Leu Tyr Val Ile Asp Val Asn Ile Asn Ile
                420                 425                 430

Ser Cys Glu Thr Asp Gly Tyr Leu Thr Lys Met Thr Cys Arg Trp Ser
            435                 440                 445

Pro Ser Thr Ile Gln Ser Leu Val Gly Ser Thr Val Gln Leu Arg Tyr
    450                 455                 460

His Arg Arg Ser Leu Tyr Cys Pro Asp Ser Pro Ser Ile His Pro Thr
465                 470                 475                 480

Ser Glu Pro Lys Asn Cys Val Leu Gln Arg Asp Gly Phe Tyr Glu Cys
                    485                 490                 495

Val Phe Gln Pro Ile Phe Leu Leu Ser Gly Tyr Thr Met Trp Ile Arg
                500                 505                 510

Ile Asn His Ser Leu Gly Ser Leu Asp Ser Pro Pro Thr Cys Val Leu
            515                 520                 525

Pro Asp Ser Val Val Lys Pro Leu Pro Pro Ser Asn Val Lys Ala Glu
    530                 535                 540

Ile Thr Val Asn Thr Gly Leu Leu Lys Val Ser Trp Glu Lys Pro Val
545                 550                 555                 560

Phe Pro Glu Asn Asn Leu Gln Phe Gln Ile Arg Tyr Gly Leu Ser Gly
                    565                 570                 575

Lys Glu Ile Gln Trp Lys Thr His Glu Val Phe Asp Ala Lys Ser Lys
                580                 585                 590

Ser Ala Ser Leu Leu Val Ser Asp Leu Cys Ala Val Tyr Val Val Gln
            595                 600                 605

Val Arg Cys Arg Arg Leu Asp Gly Leu Gly Tyr Trp Ser Asn Trp Ser
    610                 615                 620

Ser Pro Ala Tyr Thr Leu Val Met Asp Val Lys Val Pro Met Arg Gly
625                 630                 635                 640

Pro Glu Phe Trp Arg Lys Met Asp Gly Asp Val Thr Lys Lys Glu Arg
                    645                 650                 655

Asn Val Thr Leu Leu Trp Lys Pro Leu Thr Lys Asn Asp Ser Leu Cys
                660                 665                 670

Ser Val Arg Arg Tyr Val Lys His Arg Thr Ala His Asn Gly Thr
            675                 680                 685

Trp Ser Glu Asp Val Gly Asn Arg Thr Asn Leu Thr Phe Leu Trp Thr
    690                 695                 700

Glu Pro Ala His Thr Val Thr Val Leu Ala Val Asn Ser Leu Gly Ala
```

```
705                 710                 715                 720
Ser Leu Val Asn Phe Asn Leu Thr Phe Ser Trp Pro Met Ser Lys Val
                725                 730                 735
Ser Ala Val Glu Ser Leu Ser Ala Tyr Pro Leu Ser Ser Ser Cys Val
            740                 745                 750
Ile Leu Ser Trp Thr Leu Ser Pro Asp Asp Tyr Ser Leu Leu Tyr Leu
                755                 760                 765
Val Ile Glu Trp Lys Ile Leu Asn Glu Asp Asp Gly Met Lys Trp Leu
        770                 775                 780
Arg Ile Pro Ser Asn Val Lys Lys Phe Tyr Ile His Asp His Phe Ile
785                 790                 795                 800
Pro Ile Glu Lys Tyr Gln Phe Ser Leu Tyr Pro Val Phe Met Glu Gly
                805                 810                 815
Val Gly Lys Pro Lys Ile Ile Asn Gly Phe Thr Lys Asp Ala Ile Asp
                820                 825                 830
Lys Gln Gln Asn Asp Ala Gly Leu Tyr Val Ile Val Pro Ile Ile Ile
                835                 840                 845
Ser Ser Cys Val Leu Leu Leu Gly Thr Leu Leu Ile Ser His Gln Arg
850                 855                 860
Met Lys Lys Leu Phe Trp Asp Asp Val Pro Asn Pro Lys Asn Cys Ser
865                 870                 875                 880
Trp Ala Gln Gly Leu Asn Phe Gln Lys Arg Thr Asp Thr Leu
                885                 890

(2) INFORMATION FOR SEQ ID NO: 13:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 13:

GGTTTGCATA TGGAAGTC                                                     18

(2) INFORMATION FOR SEQ ID NO: 14:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 14:

CCTGAACCAT CCAGTCTCT                                                    19

(2) INFORMATION FOR SEQ ID NO: 15:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 15:

GACTCATTGT GCAGTGTTCA G                                                 21
```

(2) INFORMATION FOR SEQ ID NO: 16:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 16:

TAGTGGAGGG AGGGTCAGCA G                                          21

(2) INFORMATION FOR SEQ ID NO: 17:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 17:

ACATCTTCCC AAAATAGC                                            18

(2) INFORMATION FOR SEQ ID NO: 18:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 18:

TGCCTGGGCC TCTATCTC                                            18

(2) INFORMATION FOR SEQ ID NO: 19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 19:

GTGACGGCCC AGAGCAAGAG                                        20

(2) INFORMATION FOR SEQ ID NO: 20:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 20:

AGGGGCCGGA CTCATCGTAC TC                                     22

(2) INFORMATION FOR SEQ ID NO: 21:

(i) SEQUENCE CHARACTERISTICS:
    (A) LENGTH: 19 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO: 21:

GGTCAGAAGA TGTGGGAAA                                            19

(2) INFORMATION FOR SEQ ID NO: 22:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 22:

GTGCCCAGGA ACAATTCTT                                            19

(2) INFORMATION FOR SEQ ID NO: 23:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 23:

CTCTTCTGTC CAGTCACAGA CC                                        22

(2) INFORMATION FOR SEQ ID NO: 24:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 24:

GAATAGCTCT GGTGGCTTGC                                           20

(2) INFORMATION FOR SEQ ID NO: 25:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 25:

CTACCACGGA GACTTCTACA C                                         21

(2) INFORMATION FOR SEQ ID NO: 26:

(i) SEQUENCE CHARACTERISTICS:
        (A) LENGTH: 20 base pairs
        (B) TYPE: nucleic acid
        (C) STRANDEDNESS: single -continued

```
        (D) TOPOLOGY: linear (ii) MOLECULE TYPE: DNA (xi) SEQUENCE DESCRIPTION: SEQ ID NO: 26:

TGGATCCCCA GCTTTCTCAA                                                    20

(2) INFORMATION FOR SEQ ID NO: 27:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 27:

GGAATTCCAT ATGGTGCCTA TCCAGAA                                            27

(2) INFORMATION FOR SEQ ID NO: 28:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 28:

GCGGATCCTC AGCATTCAGG GCTAA                                              25
```

METHODS FOR USING THE OBESE PRODUCT TO STIMULATE HEMATOPOIETIC DEVELOPMENT

The present application is a continuation of U.S. patent application Ser. No. 08/618,957, filed Mar. 20, 1996, (now U.S. Pat. No. 6,355,237) which is a continuation-in-part of U.S. patent application Ser. No. 08/589,915, filed Jan. 23, 1996, (now abandoned) which is a continuation-in-part of U.S. patent application Ser. No. 08/355,888, filed Dec. 14, 1994 (now U.S. Pat. No. 5,763,211), which is a continuation-in-part of U.S. patent application Ser. No. 08/306,231 filed Sep. 14, 1994 (now U.S. Pat. No. 5,643,748), each of which is incorporated by reference herein in its entirety.

1. INTRODUCTION

The present invention relates to methods for using various forms of a novel receptor expressed by hematopoietic and endothelial cells. An additional variant form of this receptor has been detected in brain cells and shown to bind to the obese gene product, leptin. Therefore, leptin may be used to stimulate the growth and development of receptor-positive hematopoietic and endothelial cells in vitro and in vivo. In addition, this receptor is selectively expressed in hematopoietic progenitor cells with long-term repopulating potential. Thus, agents that specifically bind to this receptor may be used to identify and isolate progenitor cells for a variety of clinical applications.

2. BACKGROUND OF THE INVENTION

2.1. Hematopoietin Receptor Gene Family

A variety of diseases, including malignancy and immunodeficiency, are related to malfunction within the lympho-hematopoietic system. Some of these conditions could be alleviated and/or cured by repopulating the hematopoietic system with progenitor cells, which when triggered to differentiate would overcome the patient's deficiency. Therefore, the ability to initiate and regulate hematopoiesis is of great importance (McCune et al., 1988, Science 241:1632).

The process of blood cell formation, by which a small number of self-renewing stem cells give rise to lineage specific progenitor cells that subsequently undergo proliferation and differentiation to produce the mature circulating blood cells has been shown to be at least in part regulated by specific hormones. These hormones are collectively known as hematopoietic growth factors or cytokines (Metcalf, 1985, Science 229:16; Dexter, 1987, J. Cell Sci. 88:1; Golde and Gasson, 1988, Scientific American, July:62; Tabbara and Robinson, 1991, Anti-Cancer Res. 11:81; Ogawa, 1989, Environ. Health Presp. 80:199; Dexter, 1989, Br. Med. Bull. 45:337).

With the advent of recombinant DNA technology, the genes encoding a number of these molecules have now been molecularly cloned and expressed in recombinant form (Souza et al., 1986, Science 232:61; Gough et al., 1984, Nature 309:763; Yokota et al., 1984, Proc. Natl. Acad. Sci. U.S.A. 81:1070; Kawasaki et al., 1985, Science 230:291). These cytokines have been studied in their structure, biology and even therapeutic potential. Some of the most well characterized factors include erythropoietin (EPO), stem cell factor (SCF), granulocyte macrophage colony stimulating factor (GM-CSF), macrophage colony stimulating factor (M-CSF), granulocyte colony stimulating factor (G-CSF), the interleukins (IL-1 to IL-15) and thrombopoietin (TPO).

These cytokines act on different cell types at different stages during blood cell development, and their potential uses in medicine are far-reaching which include blood transfusions, bone marrow transplantation, correcting immunosuppressive disorders, cancer therapy, wound healing, and activation of the immune response (Golde and Gasson, 1988, Scientific American, July:62).

Apart from inducing proliferation and differentiation of hematopoietic progenitor cells, such cytokines have also been shown to activate a number of functions of mature blood cells (Stanley et al., 1976, J. Exp. Med. 143:631; Schrader et al., 1981, Proc. Natl. Acad. Sci. U.S.A. 78:323; Moore et al., 1980, J. Immunol. 125:1302; Kurland et al., 1979, Proc. Natl. Acad. Sci. U.S.A. 76:2326; Handman and Burgess, 1979, J. Immunol. 122:1134; Vadas et al., 1983, Blood 61:1232; Vadas et al., 1983, J. Immunol. 130:795), including influencing the migration of mature hematopoietic cells (Weibart et al., 1986, J. Immunol. 137:3584).

Cytokines exert their effects on target cells by binding to specific cell surface receptors. A number of cytokine receptors have been identified and the genes encoding them molecularly cloned. Several cytokine receptors have recently been classified into a hematopoietin receptor (HR) superfamily. The grouping of these receptors was based on the conservation of key amino acid motifs in the extracellular domains (Bazan, 1990, Immunology Today 11:350). The HR family is defined by three conserved motifs in the extracellular domain of its members. The first is a Trp-Ser-X-Trp-Ser (WSXWS box) motif which is highly conserved and located amino-terminal to the transmembrane domain. Most members of the HR family contain this motif. The second consists of four conserved cysteine residues located in the amino-terminal half of the extracellular region. The third is that both the conserved cysteines and the WSXWS box are found within two separate conserved fibronectin Type III (FN III) domains. The members of the HR family include receptors for ligands such as EPO, G-CSF (Fukunaga, 1990, Cell 61:341), GM-CSF, IL-3, IL-4, IL-5, IL-6, IL-7, IL-2 (β-subunit), IL-12, IL-13, IL-15 and LIF (Cosman, 1990, TIBS 15:265).

Ligands for the HR are critically involved in the proliferation, maturation and differentiation of blood cells. For example, IL-3 promotes the proliferation of early multilineage pluripotent stem cells, and synergizes with EPO to produce red cells. IL-6 and IL-3 synergize to induce proliferation of early hematopoietic precursors. GM-CSF has been shown to induce the proliferation of granulocytes as well as increase macrophage function. IL-7 is a bone marrow-derived cytokine that plays a role in producing immature T and B lymphocytes. IL-4 induces proliferation of antigen-primed B cells and antigen-specific T cells. Thus, members of this receptor superfamily are involved in the regulation of the hematopoietic system.

2.2. The Obese Gene, Gene Product and Its Receptor

In order to study the molecular mechanism of weight regulation, Zhang et al. (1994, Nature 372:425–432) cloned the mouse obese (ob) gene from ob/ob mice, which contain a single nucleotide mutation resulting in an obese phenotype. When an isolated gene fragment was used as a probe, it was shown to hybridize with RNA only in white adipose tissue by northern blot analysis, but not with RNA in any other tissue. In addition, the coding sequence of the ob gene hybridized to all vertebrate genomic DNAs tested, indicating a high level of conservation of this molecule among vertebrates. The deduced amino acid sequences are 84% identical between human and mouse, and both molecules contain features of secreted proteins.

In an effort to understand the physiologic function of the ob gene, several independent research groups produced recombinant ob gene product in bacteria for in vivo testing (Pelleymounter et al., 1995, *Science* 269:540–543; Halaas et al., 1995, *Science* 269:543–546; Campfield et al., 1995, *Science* 269:546–549). When the OB protein (also known as leptin) was injected into grossly obese mice, which possessed two mutant copies of the ob gene, the mice exhibited a reduced appetite and began to lose weight. More importantly, Campfield et al. (1995, *Science* 269:546–549) injected leptin directly into lateral ventricle, and observed that the animals reduced their food intake, suggesting that leptin acts on central neuronal networks to regulate feeding behavior and energy expenditure. This result also provided evidence that leptin-responsive cells might reside in the brain.

Recently, a leptin fusion protein was generated and used to screen for a leptin receptor (OB-R) in a cDNA expression library prepared from mouse choroid plexus, a tissue that lines brain cavities termed ventricles (Tartaglia et al., 1995, *Cell* 83:1263–1271). This approach led to the cloning of one form of the OB-R coding sequence, which reveals a single membrane-spanning receptor, sharing structural similarities with several Class I cytokine receptors, such as the gp130 signal-transducing component of the IL-6 receptor (Taga et al., 1989, *Cell* 58:573–581), the G-CSF receptor (Fukunaga et al., 1990, *Cell* 61:341–350), and the leukemia inhibitory factor receptor (Gearing et al., 1991, *EMBO J.* 10:2839–2848). Northern blot analysis and reverse transcription-polymerase chain reaction (RT-PCR) demonstrate that OB-R mRNA is expressed in several tissues, including lung, kidney, total brain and hypothalamus, but there was no report on the expression of OB-R in hematopoietic tissues.

The mouse OB-R isolated by Tartaglia, et al., contains a relatively short intracellular cytoplasmic domain as compared with other Class I cytokine receptors. Subsequently, when its human homolog was isolated from a human infant brain library, its predicted protein sequence contains a much longer intracellular domain. In view of this finding, it was speculated that different forms of the receptor might exist (Barinaga, 1996, *Science* 271:29). However, prior to the present invention, no alternative forms of the OB-R had been identified.

3. SUMMARY OF THE INVENTION

The present invention relates to methods for using Hu-B1.219 (or OB-R) variants as markers for the identification and isolation of progenitor cells in the hematopoietic and endothelial lineages, and methods for using the ob gene and its gene product, leptin, to stimulate hematopoietic and endothelial development.

The invention is bas ed, in part, on the Applicants' discovery of three forms of a novel member of the HR family, designated Hu-B1.219, which have been isolated from a human fetal liver cDNA library. Sequence comparison of these molecules with a human OB-R sequence (Tartaglia et al., 1995, *Cell* 83:1263–1271) shows that they are nearly identical in their extracellular domains. Therefore, these four molecules represent variant forms of the receptor that respond to leptin as a ligand. While the three isoforms described herein differ from the reported OB-R protein at only three amino acid positions in the extracellular domain, all four variants contain extensive differences in their intracellular domains at their 3' ends. Thus, although these receptors bind to leptin, they may transduce different signals upon ligand binding. In addition, Hu-B1.219 is expressed in several cell lines of hematopoietic and endothelial origin. Tissue expression analysis demonstrates that fetal lung and liver also contain high levels of its mRNA. Moreover, human CD34$^+$ bone marrow cells express Hu-B1.219. When mouse fetal liver cells are separated into several fractions based on their expression of AA4.1 and FcR, the expression of the mouse homolog of Hu-B1.219 is detected exclusively in the AA4.1$^+$/FcR$^-$ population, which has been shown to contain most if not all of the long-term repopulating hematopoietic progenitor cells at this stage of fetal liver development. Furthermore, mouse bone marrow cells proliferate and differentiate in response to leptin stimulation by producing erythroid colony-forming units (CFU-e), erythroid burst-forming units (BFU-e) and granulocyte-macrophage (CFU-GM) colonies. Freshly isolated murine yolk sac cells also produce erythroid growth following leptin stimulation. Additionally, Hu-B1.219 is expressed in some endothelial cells and their precursors as they are derived from the embryonic yolk sac. Therefore, Hu-B1.219 is a marker for hematopoietic and endothelial progenitor cells.

A wide variety of uses are encompassed in the present invention, including but not limited to, the use of Hu-B1.219-specific binding agents to identify and isolate hematopoietic and endothelial progenitor cells, the use of leptin to activate such progenitor cells for in vitro or ex vivo expansion, the use of leptin for in vivo stimulation of the same cell population in patients with immunodeficiency and anemia, and the use of leptin to promote angiogenesis and vasculogenesis, as well as augmentation of donor cell engraftment following bone marrow transplantation.

4. BRIEF DESCRIPTION OF THE DRAWINGS

FIGS. 1A-1G Nucleotide sequence (SEQ ID NO:1) and deduced amino acid sequences (SEQ ID NOs: 2, 3, & 4) of Form 1 of Hu-B1.219. The 3' end of this molecule is 98% identical to a human retrotransposon sequence.

FIG. 2. Nucleotide Sequence comparison between Hu-B1.219 Form 1 (SEQ ID NO: 5), Form 2 (SEQ ID NO: 6) and Form 3 (SEQ ID NO: 7) at the 3' end.

FIGS. 3A-3F Amino acid comparison between Hu-B1.219 Forms 1 (HuB1.219-1) (SEQ ID NO: 8), 2 (HuB1.219-2) (SEQ ID NO: 9), 3 (HuB1.219-3) (SEQ ID NO: 10), human OB-R (HuOBR) (SEQ ID NO: 11) and murine OB-R (MuOBR) (SEQ ID NO: 12).

FIG. 4. Human adult multiple tissue northern blots are carried out with a probe derived from the extracellular domain of Hu-B1.219 according to the manufacturer's instructions (Clontech, Palo Alto, Calif.).

Figure 5A:
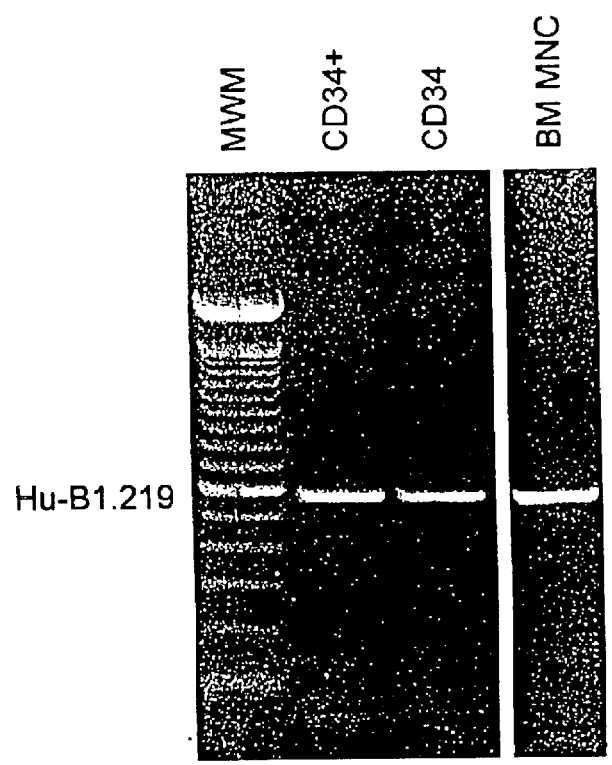
Figure 5B:
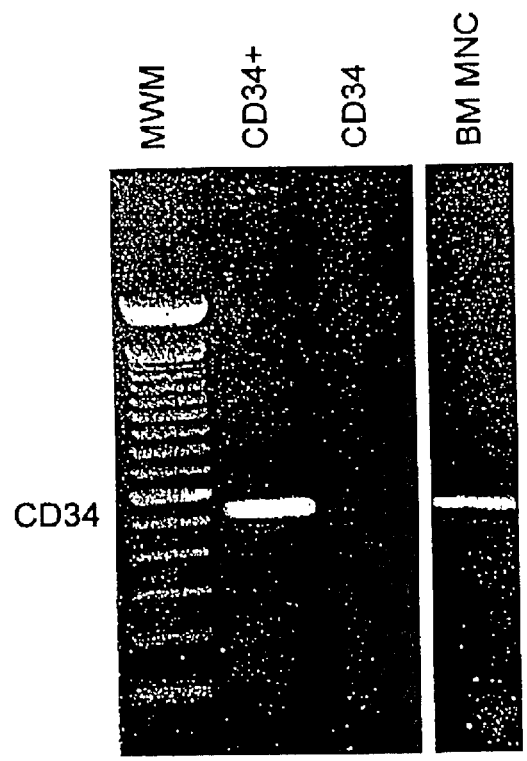

FIGS. 5A and 5B PCR analysis of Hu-B1.219 expression in human CD34$^+$ and CD34$^-$ cells. FIG. 5A is detected with Hu-B1.219 primers, whereas FIG. 5B is detected with CD34 primers. BMMNC represents bone marrow mononuclear cells as positive controls.

Figure 6A:
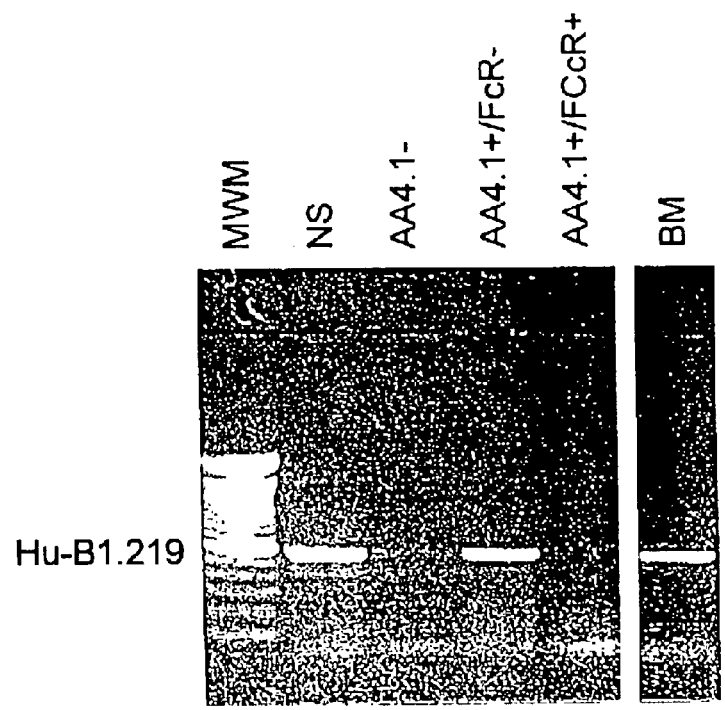
Figure 6B:
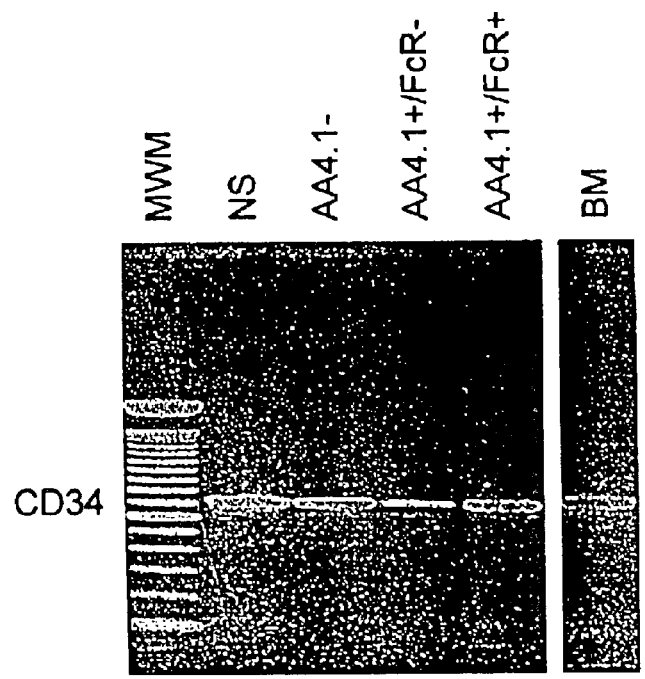

FIGS. 6A and 6B PCR analysis of murine Hu-B1.219 expression in mouse fetal liver subpopulations separated by antibodies to AA4.1 and FcR. FIG. 6A is detected with Hu-B1.219 primers, whereas FIG. 6B is detected with CD$_{34}$ primers. NS represents non-sorted cells and BM represents bone marrow cells as controls.

FIG. 7. Age matched female mice from normal, ob/ob and db/db strains were used as marrow donors for erythroid colony forming assays containing low serum concentration. □=medium containing IL-3, GM-CSF and EPO; ■=medium containing IL-3, GM-CSF, EPO and recombinant murine leptin.

FIG. 8. Three types of bone marrow colonies are stimulated by leptin: CFU-e, BFU-e and CFU-GM. □=medium containing IL-3, GM-CSF and EPO; ■=medium containing IL-3, GM-CSF, EPO and recombinant murine leptin.

5. DETAILED DESCRIPTION OF THE INVENTION

5.1. Expression of the OB-R in Hematopoietic Cells

The present invention relates to a novel hematopoietic progenitor cell marker and its use for cell identification and isolation, as well as the use of leptin to stimulate hematopoietic and endothelial development via this receptor known as Hu-B1.219. In a specific embodiment by way of example in Section 6, infra, several forms of this receptor were cloned and characterized. Amino acid sequence comparison of these related molecules with a published human OB-R sequence (Tartaglia et al., 1995, *Cell* 83:1263–1271) reveals only three amino acid differences in their extracellular domains but extensive diversity in their intracellular cytoplasmic domains. More specifically, FIG. 1A-1G shows that in the Hu-B1.219 molecules described herein, nucleotide residues #349–351 of SEQ ID NO:1 encode alanine, nucleotide residues #421–423 of SEQ ID NO:1 encode arginine and nucleotide residues #763–765 of SEQ ID NO:1 encode arginine. Additionally, the four forms diverge both in length and sequence composition from nucleotide residue #2771 of SEQ ID NO:1 and beyond. In this regard, the intracellular domain of Form 1 of Hu-B1.219 described herein is highly homologous to a retrotransposon sequence (Ono et at., 1987, *Nucl. Acid. Res.* 15:8725–8737).

Analysis of the Hu-B1.219 variants reveals significant homology to the FN III domain of the HR family indicating that they belong to the HR family of receptors. Northern blot hybridization and RT-PCR analyses indicates that Hu-B1.219 mRNA is highly expressed in cells of hematopoietic and endothelial origin. In addition, the Hu-B1.219 sequence is expressed in certain fetal tissues and tumor cell lines. Hence, in addition to its expression in the brain for weight regulation by leptin, Hu-B1.219 (or OB-R) is expressed by hematopoietic and endothelial cells, thereby rendering these cells responsive to the action of leptin.

Since additional variant forms of the molecule may exist, they can be identified by labeled DNA probes made from nucleic acid fragments corresponding to any portion of the cDNA disclosed herein in a cDNA library prepared from human fetal liver, human lung, human kidney, human choroid plexus, human hypothalamus, human prostate and human ovary. More specifically, oligonucleotides corresponding to either the 5' or 3' terminus of the cDNA sequence may be used to obtain longer nucleotide sequences. Briefly, the library may be plated out to yield a maximum of 30,000 pfu for each 150 mm plate. Approximately 40 plates may be screened. The plates are incubated at 37° C. until the plaques reach a diameter of 0.25 mm or are just beginning to make contact with one another (3–8 hours). Nylon filters are placed onto the soft top agarose and after 60 seconds, the filters are peeled off and floated on a DNA denaturing solution consisting of 0.4N sodium hydroxide. The filters are then immersed in neutralizing solution consisting of 1M Tris HCL, pH 7.5, before being allowed to air dry. The filters are prehybridized in casein hybridization buffer containing 10% dextran sulfate, 0.5M NaCl, 50 mM Tris HCL, pH 7.5, 0.1% sodium pyrophosphate, 1% casein, 1% SDS, and denatured salmon sperm DNA at 0.5 mg/ml for 6 hours at 60° C. The radiolabelled probe is then denatured by heating to 95° C. for 2 minutes and then added to the prehybridization solution containing the filters. The filters are hybridized at 60° C. for 16 hours. The filters are then washed in 1× wash mix (10× wash mix contains 3M NaCl, 0.6M Tris base, and 0.02M EDTA) twice for 5 minutes each at room temperature, then in 1× wash mix containing 1% SDS at 60° C. for 30 minutes, and finally in 0.3× wash mix containing 0.1% SDS at 60° C. for 30 minutes. The filters are then air dried and exposed to x-ray film for autoradiography. After developing, the film is aligned with the filters to select a positive plaque. If a single, isolated positive plaque cannot be obtained, the agar plug containing the plaques will be removed and placed in lambda dilution buffer containing 0.1M NaCl, 0.01M magnesium sulfate, 0.035M Tris HCl, pH 7.5, 0.01% gelatin. The phage may then be replated and rescreened to obtain single, well isolated positive plaques. Positive plaques may be isolated and the cDNA clones sequenced using primers based on the known cDNA sequence. This step may be repeated until a full length cDNA is obtained.

One method for identifying all 3' isoforms is to PCR amplify the 3' ends of the variant cDNA from a variety of tissues including but not limiting to, choroid plexus, hypothalamus, fetal liver, bone marrow, ovary, or prostate. To obtain the 3' end of the cDNA, an oligo-dT primer is used to synthesize the cDNA first strand. Hu-B1.219 specific primers from the conserved region of the gene (e.g. up stream of nucleotide 2770) and oligo-dT are then used to amplify the 3' end. The PCR fragments are cloned and sequenced by standard techniques. Once obtained, these sequences may be translated into amino acid sequence and examined for certain landmarks such as continuous open reading frame, regulatory regions that associate with tyrosine kinase activation, and finally overall structural similarity to known variants.

5.2. Hu-B1.219 as a Progenitor Cell Marker

Hu-B1.219 is expressed in cells of hematopoietic and endothelial origin. In a specific embodiment by way of example in Section 7, infra, Hu-B1.219 is expressed in early progenitor cells, and in a small percentage of progenitors with long-term repopulating potential. In order to utilize Hu-B1.219 receptor as a marker for cell identification and isolation, specific binding agents such as antibodies may be generated to the protein.

5.2.1. Generation of Antibodies

Various procedures known in the art may be used for the production of antibodies to epitopes of natural or recombinant Hu-B1.219 receptor. Such antibodies include but are not limited to polyclonal, monoclonal, chimeric, single chain, Fab fragments and fragments produced by an Fab expression library. Neutralizing antibodies i.e., those which compete for the ligand binding site of the receptor are especially preferred for diagnostics and therapeutics.

Monoclonal antibodies that bind Hu-B1.219 may be radioactively labeled allowing one to follow their location and distribution in the body after injection. Radioisotope tagged antibodies may be used as a non-invasive diagnostic tool for imaging de novo cells of tumors and metastases as well as fetal tissues.

Immunotoxins may also be designed which target cytotoxic agents to specific sites in the body. For example, high affinity Hu-B1.219 specific monoclonal antibodies may be covalently complexed to bacterial or plant toxins, such as diphtheria toxin, or ricin. A general method of preparation of antibody/hybrid molecules may involve use of thiol-crosslinking reagents such as SPDP, which attack the primary amino groups on the antibody and by disulfide exchange, attach the toxin to the antibody. The hybrid antibodies may be used to specifically eliminate Hu-B1.219 expressing tumor cells.

For the production of antibodies, various host animals may be immunized by injection with the Hu-B1.219 protein, fragments thereof or synthetic peptides, including but not limited to rabbits, mice, rats, hamsters etc. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacilli Calmette-Guerin) and Corynebacterium parvum.

Monoclonal antibodies to Hu-B1.219 may be prepared by using any technique which provides for the production of antibody molecules by continuous cell lines in culture. These include but are not limited to the hybridoma technique originally described by Kohler and Milstein, (Nature, 1975, 256:495–497), the human B-cell hybridoma technique (Kosbor et al., 1983, Immunology Today, 4;72; Cote et al., 1983, Proc. Natl. Acad. Sci., 80:2026–2030) and the EBV-hybridoma technique (Cole et al., 1985, Monoclonal Antibodies and Cancer Therapy, Alan R. Liss, Inc., pp. 77–96). In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. Alternatively, techniques described for the production of single chain antibodies (U.S. Pat. No. 4,946,778) can be adapted to produce Hu-B1.219-specific single chain antibodies.

Antibody fragments which contain specific binding sites of Hu-B1.219 may be generated by known techniques. For example, such fragments include but are not limited to, the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity to Hu-B1.219.

5.2.2. Progenitor Cell Separation

Human hematopoietic progenitor cells may be isolated using an antibody to Hu-B1.219 protein, a leptin ligand, a leptin peptide containing the receptor-binding domain or a leptin fusion protein using conventional cell separation methods well known in the art. Such Hu-B1.219-specific binding agents may be used in combination with other agents such as anti-CD34 antibodies.

Although bone marrow is the preferred cell source, other physiologic sources of hematopoietic cells may be utilized, for example, the spleen, thymus, peripheral blood, cytokine-mobilized blood, umbilical cord blood, embryonic yolk sac, or fetal liver. Bone marrow is preferably removed from the iliac crest, but may also be removed from other bone cavity. Bone marrow may be removed from bone cavity by various methods well known to those skilled in the art, including flushing the bone with a mixture of physiological media, balanced salt solution, physiological buffer, and other naturally occurring factors. Typically, the bone marrow is filtered, centrifuged and resuspended.

Once a source of hematopoietic cells is obtained, hematopoietic progenitor cells may be separated from the cell mixture by various methods which utilize an agent such as a specific antibody or a leptin ligand which specifically binds to cell surface Hu-B1.219-encoded receptor protein. These techniques may include, for example, flow cytometry using a fluorescence activated cell sorter (FACS) and specific fluorochromes, biotin-avidin or biotin-streptavidin separations using biotin conjugated to cell surface marker-specific antibodies and avidin or streptavidin bound to a solid support such as affinity column matrix or plastic surfaces, magnetic separations using antibody-coated magnetic beads, destructive separations such as antibody and complement or antibody bound to cytotoxins or radioactive isotopes.

Separation of a cell mixture via antibodies may be performed by negative or positive selection procedures. In negative separation, antibodies are used which are specific for markers present on undesired hematopoietic cells. Cells bound by an antibody may be removed or lysed and the remaining desired mixture retained. In positive separation, antibodies specific for Hu-B1.219 or leptin ligand may be used. Cells bound by the antibody or leptin are separated and retained. It will be understood that positive and negative separations may be used substantially simultaneously or in a sequential manner. It will also be understood that the present invention encompasses any separation technique which can isolate cells based on the expression of Hu-B1.219 as disclosed herein. For example, a cell mixture may be separated into $CD34^+$ and $CD34^-$ fractions first followed by Hu-B1.219-specific separation.

At present, the most common technique for antibody-based separation has been the use of flow cytometry such as by a FACS. Typically, separation by flow cytometry is performed as follows. The suspended mixture of hematopoietic cells are centrifuged and resuspended in media. Antibodies which are conjugated to fluorochrome are added to allow the binding of the antibodies to specific cell surface markers. The cell mixture is then washed by one or more centrifugation and resuspension steps. The mixture is run through FACS which separates the cells based on different fluorescence characteristics. FACS systems are available in varying levels of performance and ability, including multi-color analysis. The cells can be identified by a characteristic profile of forward and side scatter which is influenced by size and granularity, as well as by positive and/or negative expression of certain cell surface markers.

Other separation techniques besides flow cytometry may provide for faster separations. One such method is biotin-avidin based separation by affinity chromatography. Typically, such a technique is performed by incubating the washed hematopoietic cells with biotin-coupled leptin or antibodies to specific markers followed by passage through an avidin column. Biotin-antibody-cell or biotin-leptin-cell complexes bind to the column via the biotin-avidin interaction, while other cells pass through the column. Finally, the column-bound cells may be released by perturbation or other methods. The specificity of the biotin-avidin system is well suited for rapid positive separation.

Flow cytometry and biotin-avidin techniques provide highly specific means of cell separation. If desired, a separation may be initiated by less specific techniques which, however, can remove a large proportion of mature blood cells from the hematopoietic cell source. For example, magnetic bead separations may be used to initially remove differentiated hematopoietic cell populations, including T-cells, B-cells, natural killer (NK) cells, and macrophages, as well as minor cell populations including megakaryocytes, mast cells, eosinophils, and basophils. Desirably, at least about 70% and usually at least about 80% of the total hematopoietic cells present can be removed.

A preferred initial separation technique is density-gradient separation. Here, the bone marrow or other hematopoietic cell mixture preparation is centrifuged and the supernatant removed. The cells are resuspended in, for example, RPMI 1640 medium (Gibco) with 10% FCS and placed in a density gradient prepared with, for example, "FICOLL" or "PERCOLL" or "EUROCOLLINS" media. The separation may then be performed by centrifugation or automatically with a Cobel & Cell Separator '2991 (Cobev, Lakewood, Colo.). Additional separation procedures may be desirable depending on the source of the hematopoietic cell mixture and its content. For example, if blood is used as a source of hematopoietic cells, it may be desirable to lyse red blood cells prior to the separation of any fraction. Furthermore, elutriation may also be used alone or in combination with all of other purification procedures described herein (Noga et al., 1990, Prog. Clin. Biol. Res. 333:345; Noga et al., 1992, Prog. Clin. Biol. Res. 377:411).

5.3. The Obese Gene Product, Leptin

The nucleotide and amino acid sequences of both human and mouse leptin have been published recently by Zhang et al. (1994, Nature 372:425–432). Thereafter, the mouse coding sequence was used to express functional leptin in *E. coli* (Pelleymounter et al., 1995, Science 269:540–543; Halaas et al., 1995, Science 269:543–546; Campfield et al., 1995, Science 269:546–549). Furthermore, human leptin was also expressed and shown to be biologically active in murine experiments (Halaas et al., 1995, Science 269:543–546). Hence, human, murine and homologous coding sequences from other species may be expressed, and the recombinant protein purified by conventional techniques such as affinity chromatography with an antibody. Alternatively, natural protein may be directly purified from cells that secrete leptin, such as adipose cell lines.

5.3.1. Expression of Leptin Protein

For the practice of the present invention, human and mouse leptin polynucleotide sequences which encode the proteins, peptide fragments, fusion proteins or functional equivalents thereof, may be used to generate recombinant DNA molecules that direct their expression in appropriate host cells.

Due to the inherent degeneracy of the genetic code, other DNA sequences which encode substantially the same or a functionally equivalent amino acid sequence, may be used in the practice of the invention for the cloning and expression of the leptin protein. In particular, such DNA sequences include those which are capable of hybridizing to the human leptin sequences under stringent conditions.

Altered DNA sequences which may be used in accordance with the invention include deletions, additions or substitutions of different nucleotide residues resulting in a sequence that encodes the same or a functionally equivalent gene product. The gene product itself may contain deletions, additions or substitutions of amino acid residues within a coding sequence, which result in a silent change thus producing a functionally equivalent leptin protein. Such amino acid substitutions may be made on the basis of similarity in polarity, charge, solubility, hydrophobicity, hydrophilicity, and/or the amphipathic nature of the residues involved. For example, negatively charged amino acids include aspartic acid and glutamic acid; positively charged amino acids include lysine, histidine and arginine; amino acids with uncharged polar head groups having similar hydrophilicity values include the following: glycine, asparagine, glutamine, serine, threonine, tyrosine; and amino acids with nonpolar head groups include alanine, valine, isoleucine, leucine, phenylalanine, proline, methionine, tryptophan.

The DNA sequences of leptin may be engineered in order to alter the coding sequence for a variety of ends including but not limited to alterations which modify processing and expression of the gene product. For example, mutations may be introduced using techniques which are well known in the art, e.g., site-directed mutagenesis, to insert new restriction sites, to alter glycosylation patterns, phosphorylation, etc.

In another embodiment of the invention, a leptin or a modified leptin sequence may be ligated to a heterologous sequence to encode a fusion protein. It may also be useful to encode a chimeric leptin protein expressing a heterologous epitope that is recognized by a commercially available antibody. A fusion protein may also be engineered to contain a cleavage site located between a leptin sequence and the heterologous protein sequence, so that the leptin protein may be cleaved away from the heterologous moiety.

In an alternate embodiment of the invention, the coding sequence of leptin could be synthesized in whole or in part, using chemical methods well known in the art. See, for example, Caruthers et al., 1980, *Nuc. Acids Res. Symp. Ser.* 7:215–233; Crea and Horn, 180, *Nuc. Acids Res.* 9(10): 2331; Matteucci and Caruthers, 1980, *Tetrahedron Letters* 21:719; and Chow and Kempe, 1981, *Nuc. Acids Res.* 9(12):2807–2817. Alternatively, the protein itself could be produced using chemical methods to synthesize leptin amino acid sequence in whole or in part. For example, peptides can be synthesized by solid phase techniques, cleaved from the resin, and purified by preparative high performance liquid chromatography. (e.g., see Creighton, 1983, *Proteins Structures And Molecular Principles*, W.H. Freeman and Co., N.Y. pp. 50–60). The composition of the synthetic peptides may be confirmed by amino acid analysis or sequencing (e.g., the Edman degradation procedure; see Creighton, 1983, *Proteins, Structures and Molecular Principles*, W.H. Freeman and Co., N.Y., pp. 34–49).

In order to express a biologically active leptin protein, the nucleotide sequence coding for leptin, or a functional equivalent, is inserted into an appropriate expression vector, i.e., a vector which contains the necessary elements for the transcription and translation of the inserted coding sequence. The leptin gene products as well as host cells or cell lines transfected or transformed with recombinant leptin expression vectors can be used for a variety of purposes.

5.3.2. Expression Systems for Leptin

Methods which are well known to those skilled in the art can be used to construct expression vectors containing the leptin coding sequence and appropriate transcriptional/translational control signals. These methods include in vitro recombinant DNA techniques, synthetic techniques and in vivo recombination/genetic recombination. See, for example, the techniques described in Sambrook et al., 1989, Molecular Cloning A Laboratory Manual, Cold Spring Harbor Laboratory, N.Y. and Ausubel et al., 1989, Current Protocols in Molecular Biology, Greene Publishing Associates and Wiley Interscience, N.Y.

A variety of host-expression vector systems may be utilized to express the leptin coding sequence. These include but are not limited to microorganisms such as bacteria transformed with recombinant bacteriophage DNA, plasmid DNA or cosmid DNA expression vectors containing the leptin coding sequence; yeast transformed with recombinant yeast expression vectors containing the leptin coding sequence; insect cell systems infected with recombinant virus expression vectors (e.g., baculovirus) containing the leptin coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the leptin coding sequence; or animal cell systems.

The expression elements of these systems vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage λ, plac, ptrp, ptac (ptrp-lac hybrid promoter) and the like may be used; when cloning in insect cell systems, promoters such as the baculovirus polyhedrin promoter may be used; when cloning in plant cell systems, promoters derived from the genome of plant cells (e.g., heat shock promoters; the promoter for the small subunit of RUBISCO; the promoter for the chlorophyll α/β binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5K promoter) may be used; when generating cell lines that contain multiple copies of the leptin DNA, SV40-, BPV- and EBV-based vectors may be used with an appropriate selectable marker.

In bacterial systems a number of expression vectors may be advantageously selected depending upon the use intended for the leptin expressed. For example, when large quantities of leptin are to be produced for the generation of antibodies or to screen peptide libraries, vectors which direct the expression of high levels of fusion protein products that are readily purified may be desirable. Such vectors include but are not limited to the *E. coli* expression vector pUR278 (Ruther et al., 1983, EMBO J. 2:1791), in which the leptin coding sequence may be ligated into the vector in frame with the lac Z coding region so that a hybrid AS-lac Z protein is produced; pIN vectors (Inouye & Inouye, 1985, *Nucleic acids Res.* 13:3101–3109; Van Heeke & Schuster, 1989, *J. Biol. Chem.* 264:5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned polypeptide of interest can be released from the GST moiety.

In yeast, a number of vectors containing constitutive or inducible promoters may be used. For a review see, *Current Protocols in Molecular Biology*, Vol. 2, 1988, Ed. Ausubel et al., Greene Publish. Assoc. & Wiley Interscience, Ch. 13; Grant et al., 1987, Expression and Secretion Vectors for Yeast, Methods in Enzymology, Eds. Wu & Grossman, 1987, Acad. Press, N.Y., Vol. 153, pp. 516–544; Glover, 1986, *DNA Cloning*, Vol. II, IRL Press, Wash., D.C., Ch. 3; and Bitter, 1987, Heterologous Gene Expression in Yeast, *Methods in Enzymology*, Eds. Berger & Kimmel, Acad. Press, N.Y., Vol. 152, pp. 673–684; and The Molecular Biology of the Yeast *Saccharomyces*, 1982, Eds. Strathern et al., Cold Spring Harbor Press, Vols. I and II.

In cases where plant expression vectors are used, the expression of the leptin coding sequence may be driven by any of a number of promoters. For example, viral promoters such as the 35S RNA and 19S RNA promoters of CaMV (Brisson et al., 1984, Nature 310:511–514), or the coat protein promoter of TMV (Takamatsu et al., 1987, EMBO J. 6:307–311) may be used; alternatively, plant promoters such as the small subunit of RUBISCO (Coruzzi et al., 1984, EMBO J. 3:1671–1680; Broglie et al., 1984, Science 224:838–843); or heat shock promoters, e.g., soybean hsp17.5-E or hsp17.3-B (Gurley et al., 1986, Mol. Cell. Biol. 6:559–565) may be used. These constructs can be introduced into plant cells using Ti plasmids, Ri plasmids, plant virus vectors, direct DNA transformation, microinjection, electroporation, etc. For reviews of such techniques see, for example, Weissbach & Weissbach, 1988, Methods for Plant Molecular Biology, Academic Press, NY, Section VIII, pp. 421–463; and Grierson & Corey, 1988, Plant Molecular Biology, 2d Ed., Blackie, London, Ch. 7–9.

An alternative expression system which could be used to express leptin is an insect system. In one such system, *Autographa californica* nuclear polyhidrosis virus (AcNPV) is used as a vector to express foreign genes. The virus grows in *Spodoptera frugiperda* cells. The leptin coding sequence may be cloned into non-essential regions (for example the polyhedrin gene) of the virus and placed under control of an AcNPV promoter (for example the polyhedrin promoter). Successful insertion of the leptin coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (e.g., see Smith et al., 1983, J. Virol. 46:584; Smith, U.S. Pat. No. 4,215,051).

In mammalian host cells, a number of viral based expression systems may be utilized. In cases where an adenovirus is used as an expression vector, the leptin coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing leptin in infected hosts (e.g., See Logan & Shenk, 1984, *Proc. Natl. Acad. Sci. USA* 81:3655–3659). Alternatively, the vaccinia 7.5K promoter may be used. (See, e.g., Mackett et al., 1982, Proc. Natl. Acad. Sci. USA 79:7415–7419; Mackett et al., 1984, J. Virol. 49:857–864; Panicali et al., 1982, Proc. Natl. Acad. Sci. USA 79:4927–4931).

Specific initiation signals may also be required for efficient translation of inserted leptin coding sequences. These signals include the ATG initiation codon and adjacent sequences. In cases where the entire leptin gene, including its own initiation codon and adjacent sequences, is inserted into the appropriate expression vector, no additional translational control signals may be needed. However, in cases where only a portion of the leptin coding sequence is inserted, exogenous translational control signals, including the ATG initiation codon, must be provided. Furthermore, the initiation codon must be in phase with the reading frame of the leptin coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153:516–544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. The presence of several consensus N-glycosylation sites in leptin support the possibility that proper modification may be important for leptin function. Different host cells have characteristic and specific mechanisms for the post-translational processing and modification of proteins. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, WI38, etc.

For long-term, high-yield production of recombinant proteins, stable expression is preferred. For example, cell lines which stably express the leptin sequence may be engineered. Rather than using expression vectors which contain viral origins of replication, host cells can be transformed with the leptin DNA controlled by appropriate expression control elements (e.g., promoter, enhancer, sequences, transcription terminators, polyadenylation sites, etc.), and a selectable marker. Following the introduction of foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk⁻, hgprt⁻ or aprt⁻ cells, respectively. Also, antimetabolite resistance can be used as the basis of selection for dhfr, which confers resistance to methotrexate (Wigler, et al., 1980, Proc. Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin et al., 1981, J. Mol. Biol. 150:1); and hygro, which confers resistance to hygromycin (Santerre, et al., 1984, Gene 30:147) genes. Additional selectable genes have been described, namely trpB, which allows cells to utilize indole in place of tryptophan; hisD, which allows cells to utilize histinol in place of histidine (Hartman & Mulligan, 1988, Proc. Natl. Acad. Sci. USA 85:8047); and ODC (ornithine decarboxylase) which confers resistance to the ornithine decarboxylase inhibitor, 2-(difluoromethyl)-DL-ornithine, DFMO (McConlogue L., 1987, In: Current Communications in Molecular Biology, Cold Spring Harbor Laboratory ed.).

Once the leptin protein is expressed by any of the aforementioned systems, supernatants of the cultured cells or cell lysates may be subjected to various standard methods of protein purification. For example, an anti-leptin antibody or Hu-B1.219 protein can be used to purify it by affinity chromatography. Alternatively, leptin may be purified by ion exchange chromatography or HPLC. Thereafter, the purity of the protein can be confirmed by various methods, including SDS-PAGE, and the protein used immediately or stored frozen for future use. For cell cultures and in vivo administration, purified leptin must be sterilized prior to use.

5.4. Activation of HU-B1.219-Expressing Cells by Leptin

Since various forms of Hu-B1.219, including OB-R, are essentially identical in the extracellular domain, these receptors can bind leptin as a ligand. In order to compare the binding affinity of Hu-B1.219 isoforms to leptin, the variant forms are cloned into standard expression vectors, e.g. CMV promoter expression vectors, and transfected into COS and BaF3 cells. Surface expression of the receptor is then evaluated by direct binding to an anti-Hu-B1.219 antibody. In addition, leptin binding assays can also be performed as described by Tartaglia et al. (1995, Cell 83:1263) using a leptin fusion protein or soluble leptin conjugated to a radiolabel, a fluorescent dye or an enzyme. The results are compared with mock transfected cells as negative controls.

Since the four variants of Hu-B1.219 contain different intracellular domains, these isoforms can be compared with respect to their signal transduction capabilities to determine the most active form. Stimulation of most if not all hematopoietic receptors with ligands results in the rapid phosphorylation of tyrosines, both on the receptors and on a cascade of cellular protein kinases (Heidin, 1995, Cell 80:213–233; Ihle, 1995, Nature 377:591–594). Phosphorylation of these molecules results in an activation signal being propagated ultimately to the nucleus leading to gene activation. Upon ligand binding to an hematopoietin receptor, some of the first molecules to be activated in this fashion are the JAK (Janus) family of protein kinases (Ziemiecki et al., 1994, Trends Cell Biol. 4:207–212). These activated kinases, in turn, phosphorylate members of the STAT family of molecules which eventually translocate to the nucleus and form active transcription complexes (Darnell et al., 1994, Science 264:1415–1421; Zhong et al., 1994, Proc. Natl. Acad. Sci. USA 91:4806–4810; Hou et al., 1994, Science 265:1701–1706).

Therefore, cell activation by leptin can be evaluated by studying the pattern of phosphorylation of JAK1-3 following Hu-B1.219 binding. This can be carried out by culturing hematopoietic cells or Hu-B1.219 transfectants (1–100× $10^3$), in RPMI 1640 (GIBCO) with gentamicin (100 μg/ml), 2 mM glutamine (GIBCO), 10% FCS, and leptin (from 0 to 500 nM) for 10–60 minutes at 37° C. Following the incubation, the cells are washed in ice-cold PBS and resuspended in lysing buffer (1% Triton X-100, 200 mM NaCl, 10 mM Tris pH 7.5, 2.5 mM p-nitrophenyl guanidinobenzoate, 100 μM $Na_3VO_4$, 1 μM pepstatin, 50 μM 3,4-dichloroisocoumarin, 1 mM PMSF, 10 μg/ml leupeptin, 10 μg/ml aprotinin) for 30 minutes at 4° C. followed by removal of nuclei and insoluble material by centrifugation. To the cell lysate is added polyclonal antibodies to JAK1 and JAK2 (Upstate Biotechnology, Lake Placid, N.Y.) or human Tyk2, a human kinase related to the JAK family (Santa Cruz, Calif.) according to manufacturer's recommendation. This mixture is rotated for 30–60 minutes at 4° C. and then 100 μl of a 10% protein A-sepharose solution (Sigma) is added and rotated for an additional 30 minutes at 4° C. The precipitate is washed with lysis buffer and eluted in standard SDS reducing sample buffer and resolved by SDS-PAGE. The proteins are analyzed by Western blots by transferring to Immobilon membranes (Millipore). The membranes are blocked with gelatin (1%) and incubated with antiphosphotyrosine (4G10, Upstate Biotechnology, Lake Placid, N.Y.) according to the manufacturer's recommendations. Phosphorylated proteins are detected with $^{125}$I-labeled protein A (Amersham).

For the aforementioned experiment, hematopoietic cells can be obtained from human CD34$^+$ bone marrow and cord blood. For the murine experiments, three primitive populations can be evaluated, e.g. Ly-6$^+$ lineage negative bone marrow, or the equivalent in fetal liver, or AA4.1$^+$ fetal liver.

While tyrosine phosphorylation is an indication of cell activation resulting from ligand-receptor interactions, additional manifestations of activation at the cellular level can be assayed by using leptin to induce the proliferation and/or differentiation of hematopoietic precursors. Cell proliferation can be easily assessed by $^3$H-thymidine uptake or by visual enumeration of cell numbers. Differentiation of hematopoietic cells can be assayed by testing the ability of leptin to stimulate the in vitro growth and differentiation of various hematopoietic colonies. For example, a cell mixture can be isolated from the yolk sac, fetal liver or bone marrow, and cultured in standard methylcellulose colony assays with and without serum supplements, in the presence of leptin (0.1–500 nM) with or without various other cytokines (Metcalf, 1984, in *Clonal Culture of Hematopoietic Cells: Techniques and Applications*, Elsevier, N.Y.).

A standard protocol for such an assay involves density gradient centrifugation of a cell mixture by Ficoll-Hypaque (1.077 gm/cm$^3$) and resuspending about 1×10$^6$ viable cells in Iscove's Modified Dulbecco's Medium (IMDM) with 0.5–15% fetal calf serum (FCS). The cells (1–100×10$^3$/ml) are then mixed with IMDM that contains methylcellulose (1.3%), FCS (0.5–15%), BSA (1%), monothioglycerol (100 $\mu$M), gentamicin (50 $\mu$g/ml), and leptin (0.1–500 nM). In parallel cultures, additional cytokines may include: IL-3 (100 pg/ml), steel factor or c-Kit ligand or SCF (10 ng/ml), and EPO (2 U/ml). After mixing, 1 ml of the mixture is dispensed into a 25 mm bacterial grade culture dishes at 37° C. in a humidified incubator for 5 to 18 days. Using an inverted microscope the number and type of hematopoietic colonies are determined. The colony morphology is used to categorize the various colony types, e.g. BFU-e, CFU-e, CFU-G, CFU-GM, CFU-M, CFU-blast, or CFU-fibroblast (Metcalf, 1984, *Clonal Culture of Hematopoietic Cells: Techniques and Applications*, Elsevier, N.Y.; Freshney, 1994, in *Culture of Hematopoietic Cells*, Wiley-Liss, Inc., pp. 265–68). Optimal concentrations of leptin in this assay may increase both the size and the frequency of these primitive pluripotent colonies.

While leptin may be used alone, it can also be used synergistically with several cytokines to promote hematopoietic cell growth including but not limited to, IL-1, IL-3, IL-6, EPO, steel factor (SCF) and GM-CSF (1 ng/ml). In addition, since biologically active leptin is present in fetal calf serum (FCS), cultures with 0.5–15% of FCS can be tested. The specific activity of leptin in FCS can be inhibited by an anti-leptin antibody or a soluble variant of Hu-B1.219 as a control.

In particular, the effects of leptin may be tested on the primitive precursors that form high proliferative potential cells (HPPC) (McNiece and Briddell, 1994, in *Culture of Hematopoietic Cells*, Wiley-Liss, Inc., pp. 23–40) and blast colonies (Leary and Ogawa, 1994, in *Culture of Hematopoietic Cells*, Wiley-Liss Inc., pp. 41–54). In order to evaluate the effects of leptin on even more primitive cells in these assays, CD34$^+$ bone marrow, cord blood, and fetal liver cells can be first sorted by an antibody and tested in the above assays. Since recent evidence has suggested the existence of a CD34$^-$ stem cell, the CD34$^-$ Lin$^-$ population may also be stimulated by leptin.

Furthermore, the effect of leptin on the primitive long term culture initiating cells (LTCIC) and on hematopoietic stem cells can be evaluated. LTCIC are precursors that can initiate a long-term hematopoietic culture and are believed to be a function of hematopoietic stem cells (Sutherland and Eaves, 1994, in Culture of Hematopoietic Cells, Wiley-Liss, Inc., pp. 139–162; Van der Sluijs et al., 1990, Exp. Hematol. 18:893–896; Traycoff et al., 1994, Exp. Hematol. 22:215–222). The ability of these culture conditions to expand the hematopoietic stem cell can be confirmed by the competitive repopulation assay (Harrison, 1980, Blood 55:77–81). This assay allows for the quantification of hematopoietic stem cells.

Additionally, since endothelial cells also express Hu-B1.219, leptin may be used to stimulate the growth of primary endothelial cells at 0.1–500 nM in standard cultures for maintaining primary endothelial cells (Masek and Sweetenham, 1994, Br. J. Haematol. 88:855–865; Visner et al., 1994, Am. J. Physiol. 267:L406–413; Moyer et al., 1988, In Vitro Cell Dev. Biol. 24:359–368). Alternatively, leptin may be used to induce endothelial cells to produce cytokines (Broudy et al., 1987, J. Immunol. 139:464–468; Seelentag et al., 1987, EMBO J. 6:2261–2265). Supernatants of 2–5 day primary endothelial cell cultures or endothelial cell lines cultured in the presence of leptin with or without other cytokines, such as vascular endothelial growth factor (VEGF), platelet-derived growth factor (PDGF), fibroblast growth factor (FGF), transforming growth factor (TGF) and epidermal growth factor (EGF), are harvested and tested as a supplement in the hematopoietic colony assays above.

In another aspect of the invention, since receptors often form dimers on the cell surface, the combination of different Hu-B1.219 isoforms that give optimal signal transduction can be measured by growth stimulation and phosphorylation patterns. A Hu-B1.219$^-$ growth factor-dependent indicator cell line (e.g. BaF3) can be transfected with various combinations of the isoforms using standard CMV expression vectors. Following the demonstration of cell surface expression, leptin (0.1–500 nM) is added to the cultures followed by the measurement of growth rates and phosphorylation patterns by established techniques. Other cell lines such as TF-1, FD5 and TS1 may also be used.

Because of the expression of isoforms with truncated cytoplasmic tails, it is possible that another protein chain is used in some tissues as the signaling molecule in association with Hu-B1.219. Such a molecule can be screened and selected by transfecting pools of cDNA from expression libraries of a variety of tissues e.g. fetal liver, CD34$^+$ bone marrow, lung, ovary, etc. together with constructs expressing one of the truncated Hu-B1.219 isoforms into a growth factor-dependent cell line (e.g. BaF3). The ability to grow in the presence of leptin is used as a readout. In particular, the insulin receptor-related receptor (Zhang and Roth, 1992, *J. Biol. Chem.* 267:18320), the LIFRα, IL-2Rγ, IL-4Rα (Mosely et al., 1989, *Cell* 89:335) and IL-13Rα chains (Hilton et al., 1996, *Proc. Natl. Acad. Sci. USA* 93:497) may function as complementary chains for Hu-B1.219 activity. The techniques to identify the unique cDNA responsible for this complementation are well established in the art.

Additionally, agents that activate Hu-B1.219 in a manner similar to leptin may also be used in place of leptin. These agents include small molecules and peptides, and they may be selected in the following screening assay. Ten thousand BaF3 and BaF3/Hu-B1.219 (transfectant cells that express the full length Hu-B1.219 isoform) cells will be screened in microtiter plates for proliferative effects after incubation with a test agent. Without stimulation these cells die. Any growth promoting effect seen on the transfected cell line and not with the BaF3 host would indicate that the test agent specifically activates the Hu-B1.219 receptor or its signaling pathway. This assay is used to screen small molecules, including peptides, oligonucleotides, and chemical libraries.

5.5. In Vitro Uses of Leptin

In view of the expression of Hu-B1.219 in diverse cell types, leptin may be used to activate these cells in culture. The activated cells expand in number due to increased proliferation and/or differentiate to become more mature cells. In this connection, the optimal effective concentration of leptin for each cell type may be determined by conventional titration experiments in which different amounts of leptin are incubated with the specific cells and their activation levels measured by tyrosine phosphorylation, proliferation or differentiation.

In particular, hematopoietic progenitor cells express Hu-B1.219. Hematopoietic cells may be activated by exposure to leptin in vitro which results in their expansion in number prior to their use in vitro and in vivo. Such hematopoietic cells may be obtained from the bone marrow, the peripheral blood (Demuynck et al., 1995, Ann. Hematol. 71:29–33; Scheding et al., 1994, Stem Cells 12:Suppl. 1:203–210) and cord blood. In order to selectively enhance the growth of hematopoietic stem cells, the donor cell mixture may be first separated into CD34$^+$ cells, followed by leptin stimulation. The expanded cells may be used as donor cells in bone marrow transplantation or as long-term bone marrow cultures (Ponchio et al., 1995, Blood 86:3314–3321; Testa and Dexter, 1991, Curr. Opin. 3:272–278; Naughton and Naughton, 1991, U.S. Pat. No. 5,032,508) for in vitro cytotoxicity testing and the discovery of novel cytokines.

Since Hu-B1.219 is also expressed in some endothelial cells and their progenitors, leptin may be used to induce blood vessel formation in vitro. In that regard, leptin may be used alone or in combination with VEGF, PDGF, FGF or TGF-α. Blood vessels form by a combination of two primary processes. Some blood vessel growth depends on angiogenesis, in a process similar to that associated with pathological conditions. For instance, the CNS depends solely on angiogenesis for development of its vascular supply (Nodew, 1989, Am. Rev. Respir. Dis. 140:1097–1103; Risau et al., 1988, EMBO J. 7:959–962). A second process, vasculogenesis, depends on the incorporation of migratory individual endothelial cells (angioblasts) into the developing blood vessel. Leptin may be used to promote both angiogenesis and vasculogenesis.

In addition, the coding sequence of leptin may be inserted in an expression vector in accordance with Section 5.3, supra, and transferred into leptin-nonproducing cell types to result in endogenous expression of leptin. For example, hematopoietic stem cells are isolated and transfected with the leptin coding sequence. Thereafter, the cells are transferred into a bone marrow transplant recipient to cause endogenous production of leptin in stimulating hematopoiesis (U.S. Pat. No. 5,399,346).

5.6. In Vivo Uses of Leptin

The appropriate dosage and formulation of leptin on human hematopoietic and endothelial development in vivo can be first determined in animal models. For example, normal mice may be lethally irradiated or chemically ablated and reconstituted with syngeneic or allogeneic bone marrow. Since recombinant human leptin has been shown to be active on mouse cells, the rate of donor cell engraftment can be compared between leptin-treated and non-treated groups. Because of the Hu-B1.219 expression on primitive hematopoietic cells, leptin facilitates the growth and recovery of these cells in the recipient. The effect of leptin on in vivo hematopoietic proliferation and differentiation in these situations can be evaluated by reconstituting lethally irradiating mice (900R) with normal bone marrow cells (1–5×10$^6$ per mouse). Groups of animals are given PBS injections as controls and other groups receive leptin (0.1–10 mg/kg) at varying intervals. The activity of leptin is assayed by the rapidity of re-normalization and stability of blood profiles (e.g. hematocrit, WBC count, differential, etc.).

In addition, neonatal, sublethally irradiated adult normal or SCID mice can be reconstituted with human hematopoietic stem cell isolated from bone marrow, cord blood, or fractions thereof. In these mice, the human hematopoietic cells engraft and differentiate (McCune et al., 1988, Science 241:1632–1639; Sandhu et al., 1994, J. Immunol. 152:3806–3813). The effects of leptin can be evaluated by measuring the growth rate and extent of differentiation of human cells in these animals.

An effective amount of leptin may be administered into a patient who is in need of increased hematopoietic cell function. Such a need may arise from various forms of immunodeficiencies (B cell deficiencies, T cell deficiencies and combined deficiencies), myelosuppression, anemias and cancer. In these cases, leptin may be used alone or in combination with other cytokines. Additionally, since certain tumor cells such as leukemic cells express Hu-B1.219, leptin may be used therapeutically to suppress tumor growth by inducing terminal differentiation of these cells. Alternatively, leptin may be conjugated to a growth inhibitory agent such as ricin, diphtheria toxin or a chemotherapeutic drug to specifically target and destroy tumor cells. Furthermore, antagonists of leptin, e.g., a modified leptin molecule or a fragment thereof that binds to its receptor but does not trigger signal transduction may be used to block the stimulatory effects of leptin in cases where naturally occurring leptin stimulates tumor growth in vivo.

Additionally, the leptin coding sequence may be inserted in a viral vector for use in gene therapy (Jolly, 1994, Cancer Gene Therapy, 1:51). In particular, retrovirus, adenovirus, vaccinia virus and adeno-associated viruses are preferred. The leptin coding sequence-carrying virus is injected into a patient to directly supply leptin by secretion into the bloodstream or to a specific target tissue.

5.6.1. Dosage Determination

The leptin protein, and nucleic acid sequences described herein can be administered to a patient at therapeutically effective doses to treat or ameliorate various hematologic disorders and deficiencies. A therapeutically effective dose refers to that amount of the protein sufficient to result in amelioration of symptoms of the disorder, or alternatively, to that amount of a nucleic acid sequence sufficient to express a concentration of gene product which results in the amelioration of the disorder.

Toxicity and therapeutic efficacy of leptin can be determined by standard pharmaceutical procedures in cell cultures or experimental animals, e.g., for determining the LD$_{50}$ (the dose lethal to 50% of the population) and the ED$_{50}$ (the dose therapeutically effective in 50% of the population). The dose ratio between toxic and therapeutic effects is the therapeutic index and it can be expressed as the ratio LD$_{50}$/ED$_{50}$. Purified leptin which exhibits large therapeutic indices is preferred. While leptin preparations that exhibit toxic side effects may be used, care should be taken to design a delivery system that targets such preparations to the site of affected tissue in order to minimize potential damage to normal cells and, thereby, reduce side effects.

The data obtained from the cell culture assays and animal studies can be used in formulating a range of dosage for use in humans. The dosage of leptin lies preferably within a range of circulating concentrations that include the ED50 with little or no toxicity. The dosage may vary within this range depending upon the dosage form employed and the route of administration utilized. A dose may be formulated in animal models to achieve a circulating plasma concentration range that includes the IC50 (i.e., the concentration of leptin which achieves a half-maximal inhibition of symptoms) as determined in cell culture. Such information can be used to more accurately determine useful doses in humans. Levels in plasma may be measured, for example, by high performance liquid chromatography.

5.6.2. Formulation and Administration

Pharmaceutical compositions for use in accordance with the present invention may be formulated in conventional manner using one or more physiologically acceptable carriers or excipients. The compositions may be formulated for parenteral administration i.e., intravenous, subcutaneous, intradermal or intramuscular, via, for example, bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use. It is preferred that leptin be introduced into patients via intravenous administration to directly stimulate blood progenitors.

Leptin may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycollate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compositions for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the protein and a suitable powder base such as lactose or starch.

The compositions may also be formulated in rectal compositions such as suppositories or retention enemas, e.g., containing conventional suppository bases such as cocoa butter or other glycerides.

In addition to the formulations described above, the compositions may also be formulated as a depot preparation. Such long acting formulations may be administered by implantation (for example subcutaneously or intramuscularly) or by intramuscular injection. Thus, for example, the compositions may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may comprise metal or plastic foil, such as a blister pack. The pack or dispenser device may be accompanied by instructions for administration.

6. EXAMPLE

The OB-R is a Variant Form of the Hematopoietin Receptor Designated Hu-B1.219

6.1. Materials and Methods 6.1.1. Northern Blot Analysis

In order to study the expression of the Hu-B 1.219 gene, Northern blots containing RNA obtained from a variety of human tissues (Clontech, Palo Alto, Calif.) were hybridized with a radiolabelled 530 base pair (bp) DNA probe corresponding to nucleotides #578 through 1107 of SEQ ID NO:1 (see FIG. 1A-1G). Briefly, the blots were prehybridized at 42° C. for 3–6 hours in a solution containing 5×SSPE, 10× Denhardt's solution, 100 μg/ml freshly denatured, sheared salmon sperm DNA, 50% formamide (freshly deionized), and 2% SDS. The radiolabelled probe was heat denatured and added to the prehybridization mix and allowed to hybridize at 42° C. for 18–24 hours with constant shaking. The blots were rinsed in 2×SSC, 0.05% SDS several times at room temperature before being transferred to a wash solution containing 0.1×SSC, 0.1% SDS and agitated at 50° C. for 40 minutes. The blots were then covered with plastic wrap, mounted on Whatman paper and exposed to x-ray film at −70° C. using an intensifying screen.

6.1.2. Reverse Transcription/Polymerase Chain Reaction (RT/PCR)

Total RNA was isolated using standard laboratory procedures (Sambrook et al., 1989, Molecular Cloning, A Laboratory Manual, Cold Spring Harbor Laboratory, NY).

Approximately 1 μg of total RNA was reverse transcribed and the cDNA was amplified by PCR (Perkin Elmer, Norwalk, Conn.). The PCR amplification conditions were the same for Hu-B1.219 and Form 1 expression analysis. They were: 94° C. for 30 sec, 60° C. for 30 sec, 72° C. for 30 sec for a total of 40 cycles. The amplified products (224 bp for Hu-B1.219 and 816 bp for Form 1) were resolved by agarose gel electrophoresis and visualized by ethidium bromide staining. The Hu-B1.219 amplimers were GGTTTG-CATATGGAAGTC (upper)(SEQ ID NO: 13) and CCT-GAACCATCCAGTCTCT (lower)(SEQ ID NO: 14). The Form 1 specific amplimers were GACTCATTGTGCAGT-GTTCAG (upper)(SEQ ID NO: 15) and TAGTGGAGG-GAGGGTCAGCAG (lower)(SEQ ID NO: 16). The upper amplimer was commonly shared by all 3 forms, whereas the lower amplimer was Form 1-specific. The OB-R-specific (Form 4) amplimers were ACATCTTCCCAAAATAGC (upper)(SEQ ID NO: 17) and TGCCTGGGCCTCTATCTC (lower)(SEQ ID NO: 18).

6.2. Results

A number of cDNA clones were isolated from a human fetal liver cDNA library (Clontech, Palo Alto, Calif.), and the DNA sequences of several of these clones were determined. These clones (designated Hu-B1.219 #4, #33, #34, #1, #36, #8, #55, #60, #3, #51, #62) contained overlapping sequences, which were then compiled into a contiguous nucleotide sequence. Both the nucleotide sequence (SEQ ID NO:1) and the predicted protein sequence (SEQ ID NOs:2, 3, and 4) from one such cDNA are shown in FIG. 1A-1G. This cDNA sequence contains two FN III domains, each containing a "WS box", which are characteristic of genes of the HR family. Thus, this cDNA represents a novel member of the HR gene family, herein referred to as Hu-B1.219 (Table 1). Based on the sequence of Hu-B1.219 presented in FIG. 1A-1G, the translation initiation site appears at position #97 of SEQ ID NO:1. The sequence encodes an open reading frame up to and including nucleotide #2970 of SEQ ID NO:1. It is believed that the sequence from about nucleotide #2629 to about #2682 of SEQ ID NO:1 encodes a transmembrane domain. The complete sequence encodes a protein of 958 amino acids.

Subsequent amino acid sequence comparison of this molecule with other published protein sequences revealed that it was highly homologous to a recently published human OB-R protein (Tartaglia, 1995, Cell 83:1263–1271). In this connection, the sequence of Hu-B1.219 shown in FIG. 1A-1G differs from the published human OB-R sequence only at three nucleotide positions in the extracellular domain, i.e. nucleotide residues #349, #422 and #764 of SEQ ID NO:1, resulting in amino acids alanine, arginine and arginine, respectively, in Hu-B1.219 protein. The two molecules are identical in the transmembrane region and a portion of the intracellular domain up to and including nucleotide #2769 of SEQ ID NO:1, then they diverge at nucleotide #2770 of SEQ ID NO:1 and beyond.

TABLE 1

CYTOKINE RECEPTOR GENE FN III DOMAIN SIZES (BP)

| Gene | Human | Mouse | Rat |
| --- | --- | --- | --- |
| Hu-B1.219(5') | 273 | | |
| Hu-B1.219(3') | 282 | | |
| IL-2Rβ | 291 | 288 | 291 |
| IL-2Rγ | 273 | | |
| IL-3Rα | 246 | 252 | |

TABLE 1-continued

CYTOKINE RECEPTOR GENE FN III DOMAIN SIZES (BP)

| Gene | Human | Mouse | Rat |
| --- | --- | --- | --- |
| IL-3RβAic2a | | 306 and 273 | |
| IL-3RβAic2b | 306 and 282 | 303 and 276 | |
| IL-4R | 294 | | 291 |
| IL-5Rα | 276 | 273 | |
| IL-6R | 288 | 285 | |
| gp130 | 288 | 291 | 288 |
| IL-7R | | 294 | |
| IL-9R | 321 | 321 | |
| mpl | | 270 | |
| G-CSFR | 300 | 297 | |
| GM-CSFR | 288 | | |
| CNTFR | 282 | | 285 |
| PRLR | | | 288 |
| EPOR | 288 | 285 | 288 |
| LIFR-1 | 321 and 297 | | |

In addition to the sequence in FIG. 1A-1G (SEQ ID NO:1) referred to as Form 1 of Hu-B1.219 and the variant form reported to be OB-R, other lambda clones were discovered that contained different sequences from Form 1 near the 3' end known as Form 2 (SEQ ID NO:6) and Form 3 (SEQ ID NO:7). All three forms contain the identical sequence up to and including nucleotide #2770 of SEQ ID NO:1, then they diverge at nucleotide #2771 of SEQ ID NO:1 and beyond (FIG. 2). An alignment of the deduced amino acid sequences of all three forms (SEQ ID NOs:8, 9, and 10) and the OB-R (SEQ ID NOs:11 and 12) is shown in FIG. 3A-3F. Two of the originally isolated lambda clones, #36 and #8, contain the 3' end sequences of Form 1 and Form 2, respectively. The different forms of Hu-B1.219 may derive from a common precursor mRNA by an alternative splicing mechanism. The sequence in this region is consistent with well known splice junctions. It is noteworthy that the DNA sequence of Form 1 (SEQ ID NO:1) from nucleotide #2768 to the end is 98% identical to a human retrotransposon sequence that is thought to be derived from a human endogenous retroviral DNA sequence (Singer, 1982, Cell 28:433; Weiner et al., 1986, Ann. Rev. Biochem. 55:631; Lower et al., 1993, Proc. Natl. Acad. Sci. USA 90:4480; Ono et al., 1987, Nucl. Acid Res. 15:8725–8735).

In view of the foregoing, the recently published human OB-R by Tartaglia (1995, Cell 83:1263) represents a fourth form of Hu-B1.219 because of its structural similarities to the aforementioned three forms (FIG. 3A-3F) (SEQ ID NOs:8, 9, 10, 11, and 12). Although there are three amino acid substitutions in the OB-R, such differences may have resulted from allelic disparities between genetically diverse individuals. It is also possible that the three forms of the receptor described herein are specific isoforms in fetal and hematopoietic cells, while the OB-R is expressed in the brain. The differences in their intracellular domains may be involved in the different signaling pathways used by these receptor variants in different cells.

In order to examine the expression of the variant forms of cDNA, RT/PCR was performed using several human cell lines. The results in Table 2 show that Form 1 was expressed as RNA in K-562 cells and in a human fetal liver cDNA preparation. Since Hu-B1.219 was cloned from human fetal liver cDNA library, this served as a positive control. However, with respect to several other human cell lines, Form 1 was not detected, whereas Hu-B1.219 expression was positive. For example, Form 1 was not expressed in KGla cells, but Form 3 was expressed. Thus, it is possible that different forms of Hu-B1.219 are not expressed simultaneously in the same cells. There may be selective expression of certain forms in particular cell populations. Additionally, Table 3 shows expression of Hu-B1.219 in cell lines of diverse origins, including hematopoietic, endothelial, central nervous system (CNS), breast and muscle. It is interesting to note that the variant (Hu-B1.219.4) reported to be OB-R is also detected in these cells, particularly in hematopoietic cell lines, HEL and K562 (Table 3).

TABLE 2

RT/PCR ANALYSIS OF
COMPARATIVE EXPRESSION OF TWO HU-B1.219 FORMS

| Cell Lines | Hu-B1.219* | Form 1Δ | Form 3Δ |
|---|---|---|---|
| MRC5 (Lung fibroblast) | ++ | +/− | + |
| KG1a (lymphoblast) | + | − | ++ |
| Raji (B cell lymphoma) | + | − | + |
| Kit 225/K6 (T cell) | +++ | − | + |
| K562 (myelogenous leukemia) | ++++ | +++ | ++++ |
| Human Fetal Liver (positive control) | +++ | +++ | +++ |

*Analysis by Northern blots
ΔAnalysis by RT/PCR

Various human tissue RNA were probed with a radiolabelled Hu-B1.219 fragment corresponding to nucleotide numbers from #578 to #1107 of SEQ ID NO:1 as disclosed in FIG. 1A-1G for Northern blot analyses. Two different size mRNAs were detected. This result suggests that there may be another homologous gene or there is alternative splicing of a single RNA transcript. Hu-B1.219 expression was by far the strongest in human fetal issues, particularly the liver and lung. Trace levels were found in several adult tissues. Interestingly, a chronic myelogenous leukemia cell line, K562 (Table 2), was strongly positive for its expression, while some expression was also detected in A549 cells, a lung carcinoma cell line (Table 4). A representative northern blot showing the expression of Hu-B1.219 in several human tissues is presented in FIG. 4. Using more sensitive PCR, Hu-B1.219 was also detected in bone marrow.

TABLE 3

EXPRESSION OF Hu-B1.219 IN CELL LINES BY PCR

| Tissue Type | Cell Lines | Hu-B1.219 | Hu-B1.219.1 | Hu-B1.219.4 |
|---|---|---|---|---|
| Hematopoietic | K562 | ++++ | +++ | ++ |
|  | HEL | ++++ | ++ | ++++ |
|  | Mo7e | + | +/− | − |
| Endothelial | HYSE | ++++ | ++ | ++ |
|  | HYS-VS1 | + | − | + |
|  | HuVEC | ++ | + | − |
|  | ECV304 | ++ | + | − |
| CNS | U188MG | ++ | + | − |
|  | SF295 | + | + | − |
|  | U251 | ++ | + | +/− |
|  | SNB75 | + | + | + |
|  | U87MG | +++ | ++ | ++ |
|  | SNB19 | ++ | + | + |
|  | SF539 | ++ | + | + |
| Breast | DU4475 | ++ | ++ | ++ |
|  | MCF-7 | + | + | +/− |
| Muscle | 143B | ++ | + | + |
|  | fetal myoblast | +++ | ++ | +++ |

Hu-B1.219 refers to all isoforms detected.
Hu-B1.219.1 refers to Form 1 only.
Hu-B1.219.4 refers to the isoform reported to be human OB-R.

TABLE 4

SUMMARY OF NORTHERN BLOT ANALYSIS OF
Hu-B1.219 EXPRESSION IN HUMAN TISSUES AND CELL LINES

| Developmental Stage | Tissue Type | Expression |
|---|---|---|
| fetal | brain | − |
|  | lung | +++ |
|  | liver | +++++ |
|  | kidney | + |
| adult | heart | ++ |
|  | brain | +/− |
|  | placenta | + |
|  | lung | + |
|  | liver | +++ |
|  | skeletal muscle | + |
|  | kidney | +/− |
|  | pancreas | + |
|  | spleen | +/− |
|  | thymus | +/− |
|  | prostate | ++ |
|  | testis | +/− |
|  | ovary | +++ |
|  | small intestine | ++ |
|  | colon | − |
|  | peripheral blood leukocytes | − |
| cancer | HL-60 | − |
|  | HeLa | − |
|  | K-562 | +++ |
|  | MOLT-4 | − |
|  | Raji | − |
|  | SW480 | − |
|  | A549 | + |
|  | G361 | − |

Taken together, the data indicates that the Hu-B1.219 represents a new member of the human hematopoietin receptor family. It was originally cloned from a hematopoietic tissue, fetal liver. It is expressed by certain fetal tissues, and shares structural homology with several receptors which interact with ligands capable of influencing hematopoietic development. In this regard, it shares certain sequence homology with the IL-6R, IL-4R, G-CSFR, IL-3R beta chain, gp130, IL-12R, and LIFR. It contains two "WS box" motifs with the correct spacing of conserved amino acids in the FN III domains, an amphipathic sequence in block 3 of the FN III domains, and alternating hydrophobic and basic amino acids in block 6 of the FN III domains. It also contains conserved cysteines in the cysteine rich regions upstream of the FN III domains.

Despite its structural similarities with receptors expressed by hematopoietic cells, the extracellular domain of Hu-B1.219 is nearly identical to that of the human OB-R expressed in the brain. In fact, since three variant forms of Hu-B1.219 have been isolated, which show extensive sequence diversity primarily in their intracellular cytoplasmic domains, OB-R may be considered an additional isoform of the same receptor. The data presented in Table 3 further confirm that the OB-R is expressed not only in cells of the brain, but also in hematopoietic and endothelial cells. Therefore, since leptin binds to OB-R, it is also a ligand that can trigger Hu-B1.219 activation in hematopoietic and endothelial cells that express these receptor variants.

7. EXAMPLE

Hu-B1.219 is Expressed by Long-Term Repopulating Hematopoietic Progenitor Cells

7.1. Materials and Methods

7.1.1. RNA Extraction and cDNA Synthesis

Total RNA was extracted using the recommended procedure for RNAzol reagent (Biotecx). RNA was added at 1 μg/20 μof a random hexamer primed RT cDNA synthesis reaction. Mock RT reactions were also performed for each of the experimental samples. RT reactions were incubated at room temperature for 10 minutes, 42° C. for 15 minutes, 99° C. for 5 minutes and a 4° C. hold. All PCR reagents were obtained from Perkin Elmer.

7.1.2. PCR Conditions

The quality of each cDNA and mock cDNA was determined by the relative level of amplification of the β-actin gene. The conditions for actin amplification were 94° C. for 30 seconds; 55° C. for 30 seconds; 72° C. for 30 seconds for 27 to 30 cycles followed by a 72° C. extension for 5 minutes and a 4° C. hold. The DNA sequence of the β-actin primers were (forward) 5'GTGACGGCCCAGAGCAAGAG-3' (SEQ ID NO: 19) and (reverse) 5'-AGGGGCCGGACTCATCGTACTC-3' (SEQ ID NO: 20).

PCR amplification conditions for murine homolog of Hu-B1.219 and CD34 were 94° C. for 30 seconds; 60° C. for 30 seconds; 72° C. for 30 seconds for 40 to 45 cycles followed by a 72° C. extension for 5 minutes and a 4° C. hold. The primer sequences for Hu-B1.219 were (forward) 5'-GGTCAGAAGATGTGGGAAA-3' (SEQ ID NO: 21) and (reverse) 5'-GTGCCCAGGAACAATTCTT-3' (SEQ ID NO: 22). These PCR primers amplified both human and murine sequences. The CD34 primer sequences for human were (forward) 5'-CTCTTCTGTCCAGTCACAGACC-3' (SEQ ID NO: 23), and (reverse) 5'-GAATAGCTCTGGTGGCTTGC-3' (SEQ ID NO: 24). The CD34 primer sequences for murine were (forward) 5'-CTACCACGGAGACTTCTACAC-3' (SEQ ID NO: 25) and (reverse) 5'-TGGATCCCCAGCTTTCTCAA-3' (SEQ ID NO: 26). The PCR products were analyzed on a 1.5% TAE agarose gel containing 0.5 μg ethidium bromide/ml of buffer.

7.2. Results

Section 6.2, supra, demonstrates that Hu-B1.219 is expressed in hematopoietic and endothelial cells. In this connection, its expression in fetal liver is consistent with the high hematopoietic activities in the fetal liver, and its expression in fetal lung is consistent with the high level of endothelial development in fetal lung. To more precisely determine the expression of Hu-B1.219 in different populations of hematopoietic cells, human bone marrow cells were highly enriched for hematopoietic stem cells by cell sorting based on their CD34 expression (Collins et al., 1994, Stem Cells 12:577–585; Berenson, 1993, J. Hematother. 2:347–349; Civin and Gore, 1993, J. Hematother. 2:137–144). When RNA extracted from human CD34$^+$ and CD34$^-$ one marrow fractions were reacted with Hu-B1.219 primers in PCR, Hu-B1.219 message was detected in both fractions (FIG. 5A). The fact that only the CD34$^+$ fraction expressed CD34 message in PCR demonstrates the purity of the sorted population (FIG. 5B). Since the CD34$^-$ fraction contained several cell types, the detected Hu-B1.219 message might have been produced by endothelial cells. Alternatively, Hu-B1.219 may be expressed by a CD34$^-$ hematopoietic stem cell.

The expression of Fc receptors (FcR) and AA4.1 antigen in murine fetal liver cells has been used to define distinct fetal liver precursor cell subpopulations (Carlsson et al., 1995, Eur. J. Immunol. 25:2308–2317; Jordan et al., 1995, Exp. Hematol. 23:1011–1015; Trevisan and Iscove, 1995, J. Exp. Med. 181:93–103). Sorting murine fetal liver cells (day 12) based on the expression of these two markers has resulted in the isolation of a small (2–4%) subpopulation of AA4.1$^+$ and FcR$^-$ cells that are highly enriched for primitive hematopoietic stem cells. Animal repopulating experiments have shown that fetal liver cells with this phenotype contain long-term repopulating potential upon adoptive transfer into recipients with destroyed lympho-hematopoietic system. Therefore, fetal liver cells were sorted into various fractions based on expression of AA4.1 and FcR, and primers designed from Hu-B1.219 that would amplify murine Hu-B1.219 message were used to detect its expression. FIGS. 6A and 6B shows that the highly enriched AA4.1$^+$/FCR$^-$ subpopulation was the only population at this stage that expressed Hu-B1.219, whereas CD34 mRNA was detected in all fractions tested. This result indicates that while CD34 has been used as a marker of hematopoietic progenitor cells, Hu-B1.219 marks with greater specificity the long-term repopulating cells within the CD34$^+$ fraction. In addition, Hu-B1.219 expression was also observed in the subpopulation of murine adult bone marrow sorted for Ly-6 expression but negative for mature lineage markers. This fractionation procedure is a well established technique for isolating a highly purified population of hematopoietic stem cells from bone marrow (Li et al., 1992, J. Exp. Med. 175:1443–1447; Spangrude and Brooks, 1993, Blood 82:3327–3332; Szilvassy and Cory, 1993, Blood 81:2310–2320). Furthermore, murine fetal liver cells enriched for long-term repopulating cells by a recently developed method utilizing expression of the Mac-1 marker also expressed Hu-B1.219 (Morrison et al., 1995, Proc. Natl. Acad. Sci. USA 92:10302–10306).

Taken collectively, the aforementioned mouse and human studies indicate that Hu-B1.219 is a marker of a subpopulation of early progenitor cells within the CD34$^-$ fraction. In particular, Hu-B1.219 expression in long-term repopulating cells allows its use as a marker for their isolation. In this regard, an antibody specific for Hu-B1.219 or leptin may be used alone or in combination with a progenitor cell-specific antibody such as anti-CD34. For example, human bone marrow cells can be separated first into CD34$^+$ cells followed by Hu-B1.219 sorting to obtain such progenitor cells. In addition, since Hu-B1.219 expression is detected in a CD34$^-$ subpopulation, it can also be used as a marker to isolate a CD34$^-$ stem cell.

Additionally, early embryonic yolk sac cells have been described to possess the potential of giving rise to both hematopoietic and endothelial cells (Wagner and Antczak, 1995, WO95/02038). In the yolk sac, endothelial cells also produce the microenvironment for hematopoietic differentiation and proliferation. It is important to note that yolk sac cells with endothelial potential (Wei et al., 1995, Stem Cells 13:541–547) have also been shown to express Hu-B1.219. Therefore, Hu-B1.219 may also be used as a marker for endothelial progenitor cells.

8. EXAMPLE

Recombinant Leptin Stimulates Bone Marrow Colony Formation

8.1. Materials and Methods

8.1.1. Production of Recombinant Leptin

Total RNA was isolated, using RNAzol method, from brown adipose tissue from C57B mice. RT-PCR was performed using the Boehringer Mannheim "High Fidelity PCR System." PCR primers: murine leptin U462 GGAATTC-CATATGGTGCCTATCCAGAA (SEQ ID NO: 27) and L462 GCGGATCCTCAGCATTCAGGGCTAA (SEQ ID NO: 28) were designed based on Genbank sequence U18812 (Zhang et al., 1995, *NATURE* 372:425–432). The PCR product was purified using the Promega Wizard column. The PCR fragment was cut with NdeI and BamHI and cloned into NdeI-BamHI cleaved pET15b vector (Novagen). Clones were obtained first in *E. coli* strain DH10B (GibcoBRL), then transferred to the BL21 (DE3) (Novagen) host for production. Two splicing variants of mOB were identified. One that was missing a single glutamine amino acid at residue #49 from the iniator Met and one that had a glutamine at that position. Proteins were made from both clones. Murine leptin was made in *E. coli* as a fusion protein with poly histidine on the amino terminus. Recombinant murine leptin was produced as insoluble inclusion bodies and purified as described in Sambrook et al., supra. The insoluble material was denatured and "refolded" to reconstitute biologically active leptin. Inclusion bodies were dissolved in 8M Urea plus 100 mM DTT, diluted 1/100 into a "refolding reaction buffer" (100 mM Tris pH8.3, 100 mM $(NH_4)_2SO_4$, 100 $\mu$M Triton X100, 2 mM reduced glutathione, 0.4 mM oxidized glutathione) and incubated at 4° C. for 3 to 5 days. The refolded leptin was recovered by adding the histidine binding resin (Novagen) for 1 hr. The resin was recovered by centrifugation, rinsed with Novagen "binding buffer", and the Novagen "wash buffer". The leptin was eluted from the resin with Novagen "elution buffer" plus 1M imidazole. The final step was dialysis in PBS.

8.1.2. Methylcellulose Colony Forming Assays

Adult bone marrow cells were isolated from normal C5-7BL/6 female mice, ob/ob mice and db/db mice. About $1\times10^6$ viable cells were suspended in Iscove's Modified Dulbecco's Medium (IMDM) with either 0.5 to 15% fetal calf serum (FCS). The cells ($1-100\times10^3$/ml) were then mixed with IMDM that contained methylcellulose (1.3%) (Sawyer-Biddle, NY, N.Y.), FCS (4%), BSA (1%), monothioglycerol (100 $\mu$M), gentamicin (50 $\mu$g/ml), purified recombinant leptin (1 ng/ml), IL-3 (100 pg/ml), GM-CSF (1 ng/ml) and EPO (2 U/ml). After mixing, 1 ml of the mixture was dispensed into a 25 mm bacterial grade culture dishes at 37° C. in a humidified incubator for 3 days. Using an inverted microscope, CFU-e, BFU-e and GEMM$\geq$4 cells were counted (Metcalf, 1984, *Clonal Culture of Hematopoietic Cells: Techniques and Applications,* Elsevier, N.Y.; Freshney, 1994, in *Culture of Hematopoietic Cells*, Wiley-Liss, Inc., pp. 265–68).

8.2. Results

Recombinant leptin was tested for its ability to stimulate bone marrow cells to form hematopoietic colonies in methylcellulose assays. When normal mouse bone marrow cells were incubated with leptin in the presence of IL-3, GM-CSF and EPO, a two-fold increase in the number of CFU-e was observed as compared to the cells stimulated with medium containing the cytokines except leptin (FIG. 7). Similarly, leptin caused an increased number of CFU-e from ob/ob mouse bone marrow. In contrast, leptin did not stimulate CFU-e from db/db mouse bone marrow, an observation consistent with the belief of an aberrant OB-R expressed by such animals (Chen et al., 1996 Cell 84:491–495).

Additionally, leptin also stimulated other types of colonies from normal mouse bone marrow. For example, BFU-e was induced by leptin incubation, indicating that leptin acts on early progenitor cells of the erythroid lineage (FIG. 8). Furthermore, leptin also stimulated the formation of early CFU-GM colonies, indicating its effects on granulocyte, erythroid, macrophage and megakaryocyte lineages. When freshly isolated murine yolk sac cells were incubated with leptin alone, cellular proliferation and erythroid development were also induced. In conclusion, the Hu-B1.219/OB-R is not only expressed in early hematopoietic progenitor cells, it renders these cells responsive to leptin stimulation resulting in cellular proliferation and differentiation into cell types of diverse hematopoietic lineages. Thus, leptin is a growth and differentiation factor of hematopoietic progenitor cells.

9. Deposit of Microorganisms

The following organisms were deposited with the American Type Culture Collection (ATCC), 12301 Parklawn Drive, Rockville, Md. 20852.

| Strain Designation | Accession No. |
|---|---|
| Hu-B1.219, #1 | 75885 |
| Hu-B1.219, #4 | 75886 |
| Hu-B1.219, #8 | 75887 |
| Hu-B1.219, #33 | 75888 |
| Hu-B1.219, #34 | 75889 |
| Hu-B1.219, #36 | 75890 |
| Hu-B1.219, #55 | 75971 |
| Hu-B1.219, #60 | 75973 |
| Hu-B1.219, #3 | 75970 |
| Hu-B1.219, #57 | 75972 |
| Hu-B1.219, #62 | 75974 |

The use in the present application of the computer readable Sequence Listing submitted Mar. 27, 1998 in U.S. patent application Ser. No. 08/618,957 is hereby requested. The computer readable Sequence Listing on file for U.S. patent application Ser. No. 08/618,957 is identical to the paper copy (29 pages) submitted with the present application.

The present invention is not to be limited in scope by the exemplified embodiments, which are intended as illustrations of individual aspects of the invention. Indeed, various modifications for the invention in addition to those shown and described herein will become apparent to those skilled in the art from the foregoing description and accompanying drawings. Such modifications are intended to fall within the scope of the appended claims.

All publications cited herein are incorporated by reference in their entirety.

What is claimed is:

1. A method for promoting angiogenesis or vasculogenesis comprising administering to a subject in need thereof a therapeutic amount of leptin.

2. The method of claim 1 wherein angiogenesis is promoted in the subject.

3. The method of claim 2 in which leptin is administered with one or more cytokine.

4. The method of claim 3 in which the cytokine is FGF, VEGF, EGF, PDGF or TGF.

5. The method of claim 1 wherein vasculogenesis is promoted in the subject.

6. The method of claim 5 in which leptin is administered with one or more cytokine.

7. The method of claim 6 in which the cytokine is FGF, VEGF, EGF, PDGF or TGF.

8. A method for treating a subject in need of increased hematopoietic cell function or for enhancing donor bone marrow cell engraftment in bone marrow transplantation, comprising administering to a subject in need thereof a therapeutic amount of leptin and at least IL-3, EPO, and GM-CSF.

9. The method of claim 8 in which further comprises administering one or more of IL-1, IL-6, steel factor, or LIF.

10. The method of claim 8 wherein hematopoietic cell function is increased and the subject suffers from immunodeficiency.

11. The method of claim 8 wherein hematopoietic cell function is increased and the subject suffers from anemia.

* * * * *